(12) United States Patent
Minami

(10) Patent No.: US 10,703,778 B2
(45) Date of Patent: Jul. 7, 2020

(54) CYCLIC PEPTIDE, AFFINITY CHROMATOGRAPHY SUPPORT, LABELED ANTIBODY, ANTIBODY DRUG CONJUGATE, AND PHARMACEUTICAL PREPARATION

(71) Applicant: FUJIFILM Corporation, Tokyo (JP)

(72) Inventor: Koichi Minami, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/949,769

(22) Filed: Apr. 10, 2018

(65) Prior Publication Data

US 2018/0230184 A1 Aug. 16, 2018

Related U.S. Application Data

(63) Continuation of application No. PCT/JP2016/081353, filed on Oct. 21, 2016.

(30) Foreign Application Priority Data

Oct. 23, 2015 (JP) .................. 2015-209030
Oct. 21, 2016 (JP) .................. 2016-206753

(51) Int. Cl.

| C07K 7/64 | (2006.01) |
| C07K 7/54 | (2006.01) |
| C07K 1/13 | (2006.01) |
| C07K 1/14 | (2006.01) |
| C07K 17/00 | (2006.01) |
| C07K 7/08 | (2006.01) |

(Continued)

(52) U.S. Cl.

CPC .............. C07K 7/54 (2013.01); A61K 47/65 (2017.08); C07K 1/13 (2013.01); C07K 1/14 (2013.01); C07K 1/22 (2013.01); C07K 7/06 (2013.01); C07K 7/08 (2013.01); C07K 16/00 (2013.01); C07K 17/00 (2013.01); C07K 19/00 (2013.01); A61K 39/39525 (2013.01)

(58) Field of Classification Search
None
See application file for complete search history.

(56) References Cited

U.S. PATENT DOCUMENTS

| 6,677,116 B1 | 1/2004 | Blaschuk et al. |
| 2004/0087765 A1 | 5/2004 | Ronspeck et al. |
| 2004/0253247 A1 | 12/2004 | Dennis et al. |
| 2004/0254338 A1 | 12/2004 | Bednarek |

(Continued)

FOREIGN PATENT DOCUMENTS

| CA | 2251536 A1 | 12/1997 |
| EP | 2180054 A1 | 4/2010 |

(Continued)

OTHER PUBLICATIONS

Brunel, Florence M. and Dawson, Philip E.; "Synthesis of constrained helical peptides by thioether ligation: application to analogs of gp41." Chem. Comm. (2005) p. 2552-2554.*
Dubowchick, Gene M. et al, "Cathepsin b-labile dipeptide linkers for lysosomal release of doxorubicin from internalizing immunoconjugates: model studies of enzymatic drug release and antigen specific in vitro anticancer activity." Bioconjugate Chem. (2002) 13 p. 855-569.*
Australian Office Action dated Nov. 6, 2018, for corresponding Australian Patent Application No. 2016340472.
Singapore Written Opinion dated Mar. 6, 2019, for corresponding Singapore Application No. 11201803001W.
Russian Office Action and Search Report dated Dec. 27, 2018, for corresponding Russian Patent Application No. 2018114690, with an English translation.
Japanese Office Action dated Jan. 29, 2019, for corresponding Japanese Patent Application No. 2016-206753, with machine translation.
Extended European Search Report for Application No, 16857582.7, dated Oct. 30, 2018.

(Continued)

*Primary Examiner* — Fred H Reynolds
(74) *Attorney, Agent, or Firm* — Birch, Stewart, Kolasch & Birch, LLP

(57) ABSTRACT

Provided is a cyclic peptide, which is represented by Formula (I) or Formula (I') and has excellent antibody binding properties and improved chemical resistance, an affinity chromatography support, a labeled antibody, an antibody drug conjugate, and a pharmaceutical preparation.

$$R^N\text{-}X_g\text{-}[X_i\text{-}X^a\text{-}X_m\text{-}X^1\text{-}X^2\text{-}X^3\text{-}X_n\text{-}X^b\text{-}X_j]_k\text{-}X_h\text{-}R^C \quad (I)$$

In Formula (I), $X^a$ and $X^b$ each independently represent an amino acid residue derived from an amino acid, other than L-cysteine and D-cysteine, having a thiol group on a side chain and are bonded to each other through a disulfide bond, or, one of $X^a$ and $X^b$ represents an amino acid residue derived from an amino acid, other than L-cysteine and D-cysteine, having a thiol group on a side chain and the other represents an amino acid residue derived from an amino acid having a haloacetyl group on a side chain, and $X^a$ and $X^b$ are bonded to each other through a thioether bond.

$$R^N\text{-}X_g\text{-}[X_i\text{-}X^a\text{-}X_m\text{-}X^1\text{-}X^2\text{-}X^3\text{-}X_n\text{-}X^b\text{-}X_j]_k\text{-}X_h\text{-}R^C \quad (I')$$

In Formula (I'), one of $X^a$ and $X^b$ represents an amino acid residue derived from L-cysteine or D-cysteine and the other represents an amino acid residue derived from an amino acid having a haloacetyl group on a side chain, and $X^a$ and $X^b$ are bonded to each other through a thioether bond, or, one of $X^a$ and $X^b$ represents an amino acid residue derived from L-penicillamine or D-penicillamine and the other represents an amino acid residue derived from an amino acid having a haloacetyl group on a side chain, and $X^a$ and $X^b$ are bonded to each other through a thioether bond.

21 Claims, No Drawings

Specification includes a Sequence Listing.

(51) Int. Cl.
   *C07K 7/06*    (2006.01)
   *A61K 47/65*   (2017.01)
   *C07K 16/00*   (2006.01)
   *C07K 19/00*   (2006.01)
   *C07K 1/22*    (2006.01)
   *A61K 39/395*  (2006.01)

(56) References Cited

U.S. PATENT DOCUMENTS

| | | | |
|---|---|---|---|
| 2010/0121039 A1* | 5/2010 | Dennis | C07K 14/001 530/402 |
| 2014/0113874 A1 | 4/2014 | Lambris et al. | |
| 2014/0274790 A1 | 9/2014 | Ito | |

FOREIGN PATENT DOCUMENTS

| | | |
|---|---|---|
| JP | 2004-537581 A | 12/2004 |
| JP | 2007-289200 A | 11/2007 |
| WO | WO 02/086070 A2 | 10/2002 |
| WO | WO 03/013574 A1 | 2/2003 |
| WO | WO 2013/027796 A1 | 2/2013 |
| WO | WO 2015/013167 A1 | 1/2015 |

OTHER PUBLICATIONS

Lau et al., "Peptide stapling techniques based on different macrocyclisation chemistries," Chemical Society Reviews, vol. 44, No. 1, 2015, pp. 91-102.

Canadian Examination Report, dated Feb. 11, 2019, for Canadian Application No. 3,000,979.

Korean Office Action, dated Apr. 5, 2019, for Korean Application No. 10-2018-7009948, with an English translation.

International Preliminary Report on Patentability and Written Opinion of the International Searching Authority (forms PCT/IB/373, PCT/ISA/237 and PCT/IB/326), dated May 3, 2018, for corresponding International Application No. PCT/JP2016/081353, with an English translation of the Written Opinion.

International Search Report (form PCT/ISA/210), dated Jan. 24, 2017, for corresponding International Application No. PCT/JP2016/081353, with an English translation.

Korean Office Action dated Oct. 22, 2019, for corresponding Korean Patent Application No. 10-2018-7009948, with English translation.

Canadian Office Action issued in Application No. 3,000,979 dated Apr. 30, 2020.

* cited by examiner

CYCLIC PEPTIDE, AFFINITY CHROMATOGRAPHY SUPPORT, LABELED ANTIBODY, ANTIBODY DRUG CONJUGATE, AND PHARMACEUTICAL PREPARATION

CROSS-REFERENCE TO RELATED APPLICATIONS

This application is a Continuation of PCT International Application No. PCT/JP2016/081353 filed on Oct. 21, 2016, which claims priority under 35 U.S.C. § 119(a) to Japanese Patent Application No. 2015-209030 filed on Oct. 23, 2015 and Japanese Patent Application No. 2016-206753 filed on Oct. 21, 2016. Each of the above applications is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2019-02-04_1110-0613PUS1_ST25.txt" created on Feb. 4, 2019 and is 57,430 bytes in size. The sequence listing contained in this .txt file is part of the specification and is hereby incorporated by reference herein in its entirety.

BACKGROUND OF THE INVENTION

1. Field of the Invention

The present invention relates to a cyclic peptide, an affinity chromatography support, a labeled antibody, an antibody drug conjugate, and a pharmaceutical preparation.

2. Description of the Related Art

Currently, antibody drugs are drawing attention as the most reliable molecular-targeted drugs and are rapidly broadening the field of new pharmaceutical products. In most of the antibody drugs that are being developed or used currently, antibodies belonging to the class of immunoglobulin G (IgG) are used.

In the related art, for the purification of IgG antibodies, proteins such as protein A or protein G derived from *Staphylococcus aureus* are used. Because these proteins also bind to IgG of a mouse and a rabbit, the proteins have been frequently used for IgG purification at the level of reagents for research. In recent years, the antibody drugs mainly exploiting human IgG1 have been used in the pharmaceutical field, and accordingly, the importance of the antibody drugs in the industrial and pharmaceutical use has increased further. Particularly, a protein A column plays a key role in the antibody drug purification, and many of the antibody drug manufacturers adopt a purification system mainly using this column.

However, some problems have been pointed out for the protein A column. One of the problems is that protein A is mixed into purified antibodies. Protein A is a protein derived from bacteria and exhibits high immunogenicity after being administered into the human body, and there is a concern over the mixing of endotoxin into this protein. For the affinity ligand, such as protein A as a ligand, used for the purification of pharmaceutical products, in order to avoid the intermixing of undesirable substances, a high degree of purification is required. Therefore, the cost of the protein A column used for the purification of pharmaceutical products increases.

In order to solve the problem, a new IgG antibody purification system is being developed.

For example, US Patent App. No. 2004/0087765 describes an immunoglobulin-binding polypeptide which has an amino acid sequence of $R^1$-X01-X02-X03-X04-X05-X06-X07-X08-X09-X10-X11-X12-X13-$R^2$ and includes about 11 to 13 residues. US Patent App. No. 2004/0087765 describes that the polypeptide may be a cyclic peptide cyclized by forming a disulfide bond (in a case where X02=X12=C) or an amide bond (in a case where one of X02 and X12 is Dpr, Dab, K, or Orn and the other is D or E; here, Dab represents diaminobutanoic acid, Dpr represents diaminopropionic acid, and Orn represents ornithine) between X02 and X12 ([0017] to [0034]).

Furthermore, for example, WO2013/027796A describes an IgG-binding polypeptide which is represented by $(X_{1-3})$-C-$(X_2)$-H-R-G-(Xaa1)-L-V-W-C-$(X_{1-3})$ (SEQ ID NO: 92) and includes 13 to 17 amino acid residues. WO2013/027796A describes that the polypeptide may be a cyclic peptide in which a disulfide bond is formed between two cysteine (C) residues ([0042] to [0044]).

Moreover, for example, JP2007-289200A describes an IgG-Fc-binding peptide which has Formula $Xaa_1$-$Xaa_2$-$Xaa_3$-$Xaa_4$-Cys-$Xaa_5$-$Xaa_6$-$Xaa_7$-$Xaa_8$-Gly-Glu-Leu-Val-Trp-Cys-$Xaa_9$-$Xaa_{10}$-$Xaa_{11}$-$Xaa_{12}$-$Xaa_{13}$ (SEQ ID NO: 93) and has 11 to 20 amino acids (claim 39). JP2007-289200A describes that the peptide can be cyclized by the formation of a disulfide bond or a lactam bond, the residues which can form a disulfide bond include Cys, Pen, Mpr, Mpp, and the like, and the residues which can form a lactam bond include Asp, Glu, Lys, Orn, αβ-diaminobutyric acid, diaminoacetic acid, aminobenzoic acid, mercaptobenzoic acid, and the like ([0039]).

SUMMARY OF THE INVENTION

Focusing on improving the antibody binding properties by controlling the steric structure, the inventor of the present invention examined the binding activity and the chemical resistance of the antibody binding cyclic peptides described in US Patent App. No. 2004/0087765, WO2013/027796A, and JP2007-289200A. As a result, the inventor found that the binding activity and the chemical resistance of the peptides need to be further improved.

An object of the present invention is to provide a cyclic peptide having excellent antibody binding properties and improved chemical resistance, an affinity chromatography support, a labeled antibody, an antibody drug conjugate, and a pharmaceutical preparation.

In order to achieve the aforementioned object, the inventor of the present invention repeated intensive examinations. As a result, the inventor found that the amino acid residues in cross-linked portions play important roles for the chemical resistance, and accomplished the present invention.

That is, the present invention provides [1] to [50] described below.

[1] A cyclic peptide represented by Formula (I).

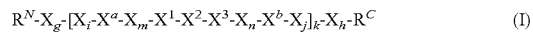

In Formula (I), $R^N$ represents an N-terminal group; $R^C$ represents a C-terminal group; $X^1$ represents an L-leucine residue, an L-isoleucine residue, an L-methionine residue, an L-lysine residue, or an L-arginine residue; $X^2$ represents an L-valine residue or an L-isoleucine residue; $X^3$ represents an L-tryptophan residue; $X^a$ and $X^b$ each independently represent an amino acid residue derived from an amino acid, other than L-cysteine and D-cysteine, having a thiol group on a side chain, and are bonded to each other through a disulfide bond, or, one of $X^a$ and $X^b$ represents an amino acid residue derived from an amino acid, other than L-cysteine and D-cysteine, having a thiol group on a side chain, and the other represents an amino acid residue derived from an amino acid having a haloacetyl group on a side chain, and $X^a$ and $X^b$ are bonded to each other through a thioether bond; $X_g$, $X_h$, $X_i$, $X_j$, $X_m$, and $X_n$ each represent g consecutive X's, h consecutive X's, i consecutive X's, j consecutive X's, m consecutive X's, and n consecutive X's; X represents an amino acid residue, and in a case where there is a plurality of X's, the plurality of X's may be the same as or different from each other; g, h, i, and j each independently represent an integer equal to or greater than 0; m and n are integers satisfying $0 \leq m \leq 9$, $0 \leq n \leq 9$, and $3 \leq m+n \leq 9$ simultaneously; and k is an integer equal to or greater than 1, and in a case where $k \geq 2$, $X^1$, $X^2$, $X^3$, $X^a$, $X^b$, $X_i$, $X_j$, $X_m$, and $X_n$ in a repeating unit $[X_i-X^a-X_m-X^1-X^2-X^3-X_n-X^b-X_j]$ each may be the same or different between the repeating units.

[2] The cyclic peptide described in [1] that is represented by Formula (IA).

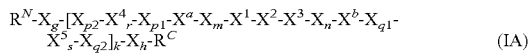

In Formula (IA), $R^N$, $R^C$, $X^1$, $X^2$, $X^3$, $X^a$, $X^b$, $X_g$, $X_h$, $X_m$, $X_n$, X, g, h, m, n, and k have the same definitions as those in Formula (I); $X^4_r$, $X^5_s$, $X_{p1}$, $X_{p2}$, $X_{q1}$, and $X_{q2}$ each represent r consecutive $X^4$'s, S consecutive $X^5$'s, p1 consecutive X's, p2 consecutive X's, q1 consecutive X's, and q2 consecutive X's; $X^4$ and $X^5$ each independently represent an amino acid residue derived from an amino acid having a carboxy group on a side chain or an amino acid residue derived from an amino acid having a hydroxy group on a side chain, and in a case where there is a plurality of $X^4$'s or $X^5$'s, the plurality of $X^4$'s or $X^5$'s may be the same as or different from each other; p1, p2, q1, and q2 each independently represent an integer equal to or greater than 0; r and s each represent an integer satisfying $0 \leq r \leq 5$, $0 \leq s \leq 5$, and $1 \leq \text{Max}(r,s) \leq 5$, where Max (r,s) represents a larger one between two numbers represented by r and s in a case where $r \neq s$ and represents r or s in a case where $r=s$; and in a case where $k \geq 2$, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}-X^4_r-X_p-X^a-X_m-X^1-X^2-X^3-X_n-X^b-X_{q1}-X^5_s-X_{q2}]$ each may be the same or different between the repeating units.

[3] The cyclic peptide described in [1] that is represented by Formula (IB).

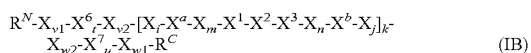

In Formula (IB), $R^N$, $R^C$, $X^1$, $X^2$, $X^3$, $X^a$, $X^b$, $X_i$, $X_j$, $X_m$, $X_n$, X, i, j, m, n, and k have the same definitions as those in Formula (I); $X^6_t$, $X^7_u$, $X_{v1}$, $X_{v2}$, $X_{w1}$, and $X_{w2}$ each represent t consecutive $X^6$'s, u consecutive $X^7$'s, v1 consecutive X's, v2 consecutive X's, w1 consecutive X's, and w2 consecutive X's; $X^6$ and $X^7$ each independently represent an amino acid residue derived from an amino acid having an immobilizing functional group on a side chain, and in a case where there is a plurality of $X^6$'s or $X^7$'s, the plurality of $X^6$'s or $X^7$'s may be the same as or different from each other; t and u each represent an integer satisfying $0 \leq t \leq 5$, $0 \leq u \leq 5$, and $1 \leq \text{Max}(t,u) \leq 5$, where Max (t,u) represents a larger one between two numbers represented by t and u in a case where $t \neq u$ and represents t or u in a case where $t=u$; v1, v2, w1, and w2 each independently represent an integer equal to or greater than 0; and in a case where $k \geq 2$, $X^1$, $X^2$, $X^3$, $X^a$, $X^b$, $X_i$, $X_j$, $X_m$, and $X_n$ in a repeating unit $[X_i-X^a-X_m-X^1-X^2-X^3-X_n-X^b-X_j]$ each may be the same or different between the repeating units.

[4] The cyclic peptide described in any one of [1] to [3] that is represented by Formula (IC).

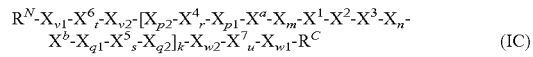

In Formula (IC), $R^N$, $R^C$, $X^1$, $X^2$, $X^3$, $X^a$, $X^b$, $X_m$, $X_n$, X, m, n, and k have the same definitions as those in Formula (I); $X_p$, $X_{p2}$, $X_{q1}$, $X_{q2}$, $X^4_r$, $X^5_s$, $X^6_t$, $X^7_u$, $X_{v1}$, $X_{v2}$, $X_{w1}$, and $X_{w2}$ each represent p1 consecutive X's, p2 consecutive X's, q1 consecutive X's, q2 consecutive X's, r consecutive $X^4$'s, S consecutive $X^5$'s, t consecutive $X^6$'s, u consecutive $X^7$'s, v1 consecutive X's, v2 consecutive X's, w1 consecutive X's, and w2 consecutive X's; $X^4$ and $X^5$ each independently represent an amino acid residue derived from an amino acid having a carboxy group on a side chain or an amino acid residue derived from an amino acid having a hydroxy group on a side chain, and in a case where there is a plurality of $X^4$'s or $X^5$'s, the plurality of $X^4$'s or $X^5$'s may be the same as or different from each other; $X^6$ and $X^7$ each independently represent an amino acid residue derived from an amino acid having an immobilizing functional group on a side chain, and in a case where there is a plurality of $X^6$ or $X^7$, the plurality of $X^6$'s or $X^7$'s may be the same as or different from each other; p1, p2, q1, and q2 each independently represent an integer equal to or greater than 0; r and s each represent an integer satisfying $0 \leq r \leq 5$, $0 \leq s \leq 5$, and $1 \leq \text{Max}(r,s) \leq 5$, where Max (r,s) represents a larger one between two numbers represented by r and s in a case where $r \neq s$ and represents r or s in a case where $r=s$; t and u each represent an integer satisfying $0 \leq t \leq 5$, $0 \leq u \leq 5$, and $1 \leq \text{Max}(t,u) \leq 5$, where Max (t,u) represents a larger one between two numbers represented by t and u in a case where $t \neq u$ and represents t or u in a case where $t=u$; v1, v2, w1, and w2 each independently represent an integer equal to or greater than 0; and in a case where $k \geq 2$, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}-X^4_r-X_{p1}-X^a-X_m-X^1-X^2-X^3-X_n-X^b-X_{q1}-X^5_s-X_{q2}]$ each may be the same or different between the repeating units.

[5] The cyclic peptide described in [1], in which $8 \leq g+h+k \times (i+j+m+n+5) \leq 50$.

[6] The cyclic peptide described in [2], in which $8 \leq g+h+k \times (m+n+p1+p2+q1+q2+5) \leq 50$.

[7] The cyclic peptide described in [3], in which $8 \leq v1+v2+w1+w2+t+u+k \times (i+j+m+n+5) \leq 50$.

[8] The cyclic peptide described in [4], in which $8 \leq v1+v2+w1+w2+t+u+k \times (m+n+p1+p2+q1+q2+5) \leq 50$.

[9] The cyclic peptide described in [2], [4], [6], or [8], in which the amino acid having a carboxy group on a side chain is at least one kind of amino acid selected from the group consisting of L-aspartic acid, D-aspartic acid, L-glutamic acid, D-glutamic acid, L-homoglutamic acid, and D-homoglutamic acid, and the amino acid having a hydroxy group on a side chain is at least one kind of amino acid selected from the group consisting of L-serine, D-serine, L-homoserine, D-homoserine, L-tyrosine, D-tyrosine, L-threonine, D-threonine, L-allothreonine, and D-allothreonine.

[10] The cyclic peptide described in [9], in which the amino acid having a carboxy group on a side chain is L-aspartic acid, and the amino acid having a hydroxy group on a side chain is L-threonine.

[11] The cyclic peptide described in [3], [4], [7], or [8], in which the immobilizing functional group is an amino group or a thiol group.

[12] The cyclic peptide described in [3], [4], [7], or [8], in which the amino acid having an immobilizing functional group on a side chain is at least one kind of amino acid selected from the group consisting of L-lysine, D-lysine, L-cysteine, D-cysteine, L-homocysteine, and D-homocysteine.

[13] The cyclic peptide described in any one of [1] to [12], in which $X^a$ is an amino acid residue derived from an amino acid having a chloroacetyl group on a side chain, selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, and N-ε-chloroacetyl-D-lysine, $X^b$ is an amino acid residue derived from L-homocysteine or D-homocysteine, and $X^a$ and $X^b$ are bonded to each other through a thioether bond.

[14] The cyclic peptide described in any one of [1] to [12], in which $X^a$ is an amino acid residue derived from L-homocysteine or D-homocysteine, $X^b$ is an amino acid residue derived from an amino acid having a chloroacetyl group on a side chain, selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, and N-ε-chloroacetyl-D-lysine, and $X^a$ and $X^b$ are bonded to each other through a thioether bond.

[15] The cyclic peptide described in any one of [1] to [14], in which the partial amino acid sequence $X_m$-$X^1$-$X^2$-$X^3$-$X_n$ in Formula (I), (IA), (IB), or (IC) and an amino acid sequence (SEQ ID NO: 1) represented by Formula (1) share sequence homology equal to or higher than 70%.

$$\text{A-Y-H-L-G-E-L-V-W} \quad (1)$$

In Formula (1), A represents an L-alanine residue; Y represents an L-tyrosine residue; H represents an L-histidine residue; L represents an L-leucine residue; G represents a glycine residue; E represents an L-glutamic acid residue; V represents an L-valine residue; and W represents an L-tryptophan residue.

[16] The cyclic peptide described in any one of [1] to [15], in which in Formula (I), (IA), (IB), or (IC), k=1. [17] The cyclic peptide described in [1] that is represented by Formula (II).

$$R^N\text{-}X_{v0}\text{-}X^6_{t0}\text{-}X_{e0}\text{-}X^4_{r0}\text{-}X_{p0}\text{-}X^a\text{-A-Y-H-X-G-E-L-V-W-}X^b\text{-}X_{q0}\text{-}X^5_{s0}\text{-}X_{f0}\text{-}X^7_{u0}\text{-}X_{w0}\text{-}R^C \quad (II)$$

In Formula (II), $X^a$, $X^b$, X, $R^N$, and $R^C$ have the same definitions as those in Formula (I); $X^4$ and $X^5$ each independently represent an amino acid residue derived from an amino acid having a carboxy group on a side chain or an amino acid residue derived from an amino acid having a hydroxy group on a side chain, and in a case where there is a plurality of $X^4$'s or $X^5$'s, the plurality of $X^4$'s or $X^5$'s may be the same as or different from each other; $X^6$ and $X^7$ each independently represent an amino acid residue derived from an amino acid having an immobilizing functional group on a side chain, and in a case where there is a plurality of $X^6$'s or $X^7$'s, the plurality of $X^6$'s or $X^7$'s may be the same as or different from each other; $X^8$ represents an L-leucine residue, a D-leucine residue, an L-arginine residue, or a D-arginine residue; e0 and f0 each represent an integer satisfying 0≤e0≤10 and 0≤f0≤10; p0 and q0 each represent an integer satisfying 0≤p0≤5 and 0≤q0≤5; r0 and s0 each represent an integer satisfying 0≤r0≤5 and 0≤s0≤5; t0 and u0 each represent an integer satisfying 0≤t0≤5 and 0≤u0≤5; v0 and w0 each represent an integer satisfying 0≤v0≤5 and 3≤w0≤5; p0, q0, r0, s0, t0, u0, v0, and w0 satisfy 0≤p0+q0+r0+s0+t0+u0+v0+w0≤39; A represents an L-alanine residue or a D-alanine residue; Y represents an L-tyrosine residue or a D-tyrosine residue; H represents an L-histidine residue or a D-histidine residue; G represents a glycine residue; E represents an L-glutamic acid residue or a D-glutamic acid residue; L represents an L-leucine residue; V represents an L-valine residue; and W represents an L-tryptophan residue.

[18] The cyclic peptide described in [17], in which $X^6$ and $X^7$ each independently represent an amino acid residue derived from an amino acid selected from the group consisting of L-lysine, D-lysine, L-cysteine, D-cysteine, L-homocysteine, and D-homocysteine.

[19] The cyclic peptide described in [17] or [18], in which $X^a$ is an amino acid residue derived from an amino acid having a chloroacetyl group on a side chain, selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, and N-ε-chloroacetyl-D-lysine, $X^b$ is an amino acid residue derived from L-homocysteine or D-homocysteine, and $X^a$ and $X^b$ are bonded to each other through a thioether bond.

[20] The cyclic peptide described in [17] or [18], in which $X^a$ is an amino acid residue derived from L-homocysteine or D-homocysteine, $X^b$ is an amino acid residue derived from an amino acid having a chloroacetyl group on a side chain, selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, and N-δ-chloroacetyl-D-lysine, and $X^a$ and $X^b$ are bonded to each other through a thioether bond.

[21] A cyclic peptide represented by Formula (I')

$$R^N\text{-}X_g\text{-}[X_i\text{-}X^a\text{-}X_m\text{-}X^1\text{-}X^2\text{-}X^3\text{-}X_n\text{-}X^b\text{-}X_j]_k\text{-}X_h\text{-}R^C \quad (I')$$

In Formula (I'), $R^N$ represents an N-terminal group; $R^C$ represents a C-terminal group; $X^1$ represents an L-leucine residue, an L-isoleucine residue, an L-methionine residue, an L-lysine residue, or an L-arginine residue; $X^2$ represents an L-valine residue or an L-isoleucine residue; $X^3$ represents an L-tryptophan residue; one of $X^a$ and $X^b$ represents an amino acid residue derived from L-cysteine or D-cysteine and the other represents an amino acid residue derived from an amino acid having a haloacetyl group on a side chain, and $X^a$ and $X^b$ are bonded to each other through a thioether bond, or, one of $X^a$ and $X^b$ represents an amino acid residue derived from L-penicillamine or D-penicillamine, and the other represents an amino acid residue derived from an amino acid having a haloacetyl group on a side chain, and $X^a$ and $X^b$ are bonded to each other through a thioether bond; $X_g$, $X_h$, $X_i$, $X_j$, $X_m$, and $X_n$ each represent g consecutive X's, h consecutive X's, i consecutive X's, j consecutive X's, m consecutive X's, and n consecutive X's; in a case where one of $X^a$ and $X^b$ represents an amino acid residue derived from L-cysteine or D-cysteine, X represents an amino acid residue derived from an amino acid other than L-serine, D-serine, L-homoserine, D-homoserine, L-arginine, and D-arginine, in a case where one of $X^a$ and $X^b$ represents an amino acid residue derived from L-penicillamine or D-penicillamine, X represents an amino acid residue derived from an amino acid other than L-serine and D-serine, and in a case where there is a plurality of X's, the plurality of X's may be the same as or different from each other; g, h, i, and j each independently represent an integer equal to or greater than 0; m and n are integers satisfying $0 \leq m \leq 9$, $0 \leq n \leq 9$, and $3 \leq m+n \leq 9$ simultaneously; and k is an integer equal to or greater than 1, and in a case where $k \geq 2$, $X^1$, $X^2$, $X^3$, $X^a$, $X^b$, $X_i$, $X_j$, $X_m$, and $X_n$ in a repeating unit $[X_i\text{-}X^a\text{-}X_m\text{-}X^1\text{-}X^2\text{-}X^3\text{-}X_n\text{-}X^b\text{-}X_j]$ each may be the same or different between the repeating units.

[22] The cyclic peptide described in [21] that is represented by Formula (I'A).

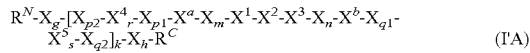
(I'A)

In Formula (I'A), $R^N$, $R^C$, $X^1$, $X^2$, $X^3$, $X^a$, $X^b$, $X_g$, $X_h$, $X_m$, $X_n$, g, h, m, n, and k have the same definitions as those in Formula (I'); $X^4_r$, $X^5_s$, $X_{p1}$, $X_{p2}$, $X_{q1}$, and $X_{q2}$ each represent r consecutive $X^4$'s, s consecutive $X^5$'s, p1 consecutive X's, p2 consecutive X's, q1 consecutive X's, and q2 consecutive X's; in a case where one of $X^a$ and $X^b$ represents an amino acid residue derived from L-cysteine or D-cysteine, X represents an amino acid residue derived from an amino acid other than L-serine, D-serine, L-homoserine, D-homoserine, L-arginine, and D-arginine, in a case where one of $X^a$ and $X^b$ represents an amino acid residue derived from L-penicillamine or D-penicillamine, X represents an amino acid residue derived from an amino acid other than L-serine and D-serine, and in a case where there is a plurality of X's, the plurality of X's may be the same as or different from each other; in a case where one of $X^a$ and $X^b$ represents an amino acid residue derived from L-cysteine or D-cysteine, $X^4$ and $X^5$ each independently represent an amino acid residue derived from an amino acid having a carboxy group on a side chain or an amino acid residue derived from an amino acid, other than L-serine, D-serine, L-homoserine, and D-homoserine, having a hydroxy group on a side chain, in a case where one of $X^a$ and $X^b$ represents an amino acid residue derived from L-penicillamine or D-penicillamine, $X^4$ and $X^5$ each independently represent an amino acid residue derived from an amino acid having a carboxy group on a side chain or an amino acid residue derived from an amino acid, other than L-serine or D-serine, having a hydroxy group on a side chain, and in a case where there is a plurality of $X^4$'s or $X^5$'s, the plurality of $X^4$'s or $X^5$'s may be the same as or different from each other; p1, p2, q1, and q2 each independently represent an integer equal to or greater than 0; r and s each represent an integer satisfying $0 \leq r \leq 5$, $0 \leq s \leq 5$, and $1 \leq \text{Max}(r,s) \leq 5$, where Max (r,s) represents a larger one between two numbers represented by r and s in a case where $r \neq s$ and represents r or s in a case where $r=s$; and in a case where $k \geq 2$, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}\text{-}X^4_r\text{-}X_{p1}\text{-}X^a\text{-}X_m\text{-}X^1\text{-}X^2\text{-}X^3\text{-}X_n\text{-}X^b\text{-}X_{q1}\text{-}X^5_s\text{-}X_{q2}]$ each may be the same or different between the repeating units.

[23] The cyclic peptide described in [21] that is represented by Formula (I'B).

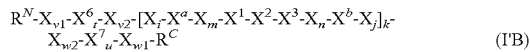
(I'B)

In Formula (I'B), $R^N$, $R^C$, $X^1$, $X^2$, $X^3$, $X^a$, $X^b$, $X_i$, $X_j$, $X_m$, $X_n$, i, j, m, n, and k have the same definitions as those in Formula (I'); $X^6_t$, $X^7_u$, $X_{v1}$, $X_{v2}$, $X_{w1}$, and $X_{w2}$ each represent t consecutive $X^6$'s, u consecutive $X^7$'s, v1 consecutive X's, v2 consecutive X's, w1 consecutive X's, and w2 consecutive X's; in a case where one of $X^a$ and $X^b$ represents an amino acid residue derived from L-cysteine or D-cysteine, X represents an amino acid residue derived from an amino acid other than L-serine, D-serine, L-homoserine, D-homoserine, L-arginine, and D-arginine, in a case where one of $X^a$ and $X^b$ represents an amino acid residue derived from L-penicillamine or D-penicillamine, X represents an amino acid residue derived from an amino acid other than L-serine and D-serine, and in a case where there is a plurality of X's, the plurality of X's may be the same as or different from each other; in a case where one of $X^a$ and $X^b$ represents an amino acid residue derived from L-cysteine or D-cysteine, $X^6$ and $X^7$ each independently represent an amino acid residue derived from an amino acid, other than L-serine, D-serine, L-homoserine, D-homoserine, L-arginine, and D-arginine, having an immobilizing functional group on a side chain or each independently represent an amino acid residue derived from an amino acid having an immobilizing functional group on a side chain, in a case where one of $X^a$ and $X^b$ represents an amino acid residue derived from L-penicillamine or D-penicillamine, $X^6$ and $X^7$ each independently represent an amino acid residue derived from an amino acid, other than L-serine and D-serine, having an immobilizing functional group on a side chain, and in a case where there is a plurality of $X^6$'s or $X^7$'s, the plurality of $X^6$'s or $X^7$'s may be the same as or different from each other; t and u each represent an integer satisfying $0 \leq t \leq 5$, $0 \leq u \leq 5$, and $1 \leq \text{Max}(t,u) \leq 5$, where Max (t,u) represents a larger one between two numbers represented by t and u in a case where $t \neq u$ and represents t or u in a case where $t=u$; v1, v2, w1, and w2 each independently represent an integer equal to or greater than 0; and in a case where $k \geq 2$, $X^1$, $X^2$, $X^3$, $X^a$, $X^b$, $X_i$, $X_j$, $X_m$, and X, in a repeating unit $[X_i\text{-}X^a\text{-}X_m\text{-}X^1\text{-}X^2\text{-}X^3\text{-}X_n\text{-}X^b\text{-}X_j]$ each may be the same or different between the repeating units.

[24] The cyclic peptide described in any one of [21] to [23] that is represented by Formula (I'C).

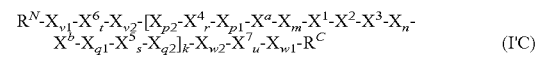
(I'C)

In Formula (I'C), $R^N$, $R^C$, $X^1$, $X^2$, $X^3$, $X^a$, $X^b$, $X_m$, $X_n$, m, n, and k have the same definitions as those in Formula (I'); $X_{p1}$, $X_{p2}$, $X_{q1}$, $X_{q2}$, $X^4_r$, $X^5_s$, $X^6_t$, $X^7_u$, $X_{v1}$, $X_{v2}$, $X_{w1}$, and $X_{w2}$ each represent p1 consecutive X's, p2 consecutive X's, q1 consecutive X's, q2 consecutive X's, r consecutive $X^4$'s, s consecutive $X^5$'s, t consecutive $X^6$'s, u consecutive $X^7$'s, v1 consecutive X's, v2 consecutive X's, w1 consecutive X's, and w2 consecutive X's; in a case where one of $X^a$ and $X^b$ represents an amino acid residue derived from L-cysteine or D-cysteine, X represents an amino acid residue derived from an amino acid other than L-serine, D-serine, L-homoserine, D-homoserine, L-arginine, and D-arginine, in a case where one of $X^a$ and $X^b$ represents an amino acid residue derived from L-penicillamine or D-penicillamine, X represents an amino acid residue derived from an amino acid other than L-serine and D-serine, and in a case where there is a plurality of X's, the plurality of X's may be the same as or different from each other; in a case where one of $X^a$ and $X^b$ represents an amino acid residue derived from L-cysteine or D-cysteine, $X^4$ and $X^5$ each independently represent an amino acid residue derived from an amino acid having a carboxy group on a side chain or an amino acid residue derived from an amino acid, other than L-serine, D-serine, L-homoserine, and D-homoserine, having a hydroxy group on a side chain, in a case where one of $X^a$ and $X^b$ represents an amino acid residue derived from L-penicillamine or D-penicillamine, $X^4$ and $X^5$ each independently represent an amino acid residue derived from an amino acid having a carboxy group on a side chain or an amino acid residue derived from an amino acid, other than L-serine and D-serine, having a hydroxy group on a side chain, and in a case where there is a plurality of $X^4$'s or $X^5$'s, the plurality of $X^4$'s or $X^5$'s may be the same as or different from each other; in a case where one of $X^a$ and $X^b$ represents an amino acid residue derived from L-cysteine or D-cysteine, $X^6$ and $X^7$ each independently represent an amino acid residue derived from an amino acid, other than L-serine, D-serine, L-homoserine, D-homoserine, L-arginine, and D-arginine, having an immobilizing functional group on a side chain or each independently represent an amino acid residue derived from an amino acid having an immobilizing functional group on a side chain, in a case where one of $X^a$ and $X^b$ represents an amino acid residue derived from L-penicillamine or D-penicillamine, $X^6$ and $X^7$ each independently represent an amino acid residue derived from an amino acid, other than L-serine and D-serine, having an immobilizing functional group on a side chain, and in a case where there is a plurality of $X^6$'s or $X^7$'s, the plurality of $X^6$'s or $X^7$'s may be the same as or different from each other; p1, p2, q1, and q2 each independently represent an integer equal to or greater than 0; r and s each represent an integer satisfying $0 \leq r \leq 5$, $0 \leq s \leq 5$, and $1 \leq \text{Max}(r,s) \leq 5$, where $\text{Max}(r,s)$ represents a larger one between two numbers represented by r and s in a case where $r \neq s$ and represents r or s in a case where $r=s$; t and u each represent an integer satisfying $0 \leq t \leq 5$, $0 \leq u \leq 5$, and $1 \leq \text{Max}(t,u) \leq 5$, where $\text{Max}(t,u)$ represents a larger one between two numbers represented by t and u in a case where $t \neq u$ and represents t or u in a case where $t=u$; v1, v2, w1, and w2 each independently represent an integer equal to or greater than 0; and in a case where $k \geq 2$, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}\text{-}X^4_r\text{-}X_{p1}\text{-}X^a\text{-}X_m\text{-}X^1\text{-}X^2\text{-}X^3\text{-}X_n\text{-}X^b\text{-}X_{q1}\text{-}X^5_s\text{-}X_{q2}]$ each may be the same or different between the repeating units.

[25] The cyclic peptide described in [21], in which $8 \leq g+h+k \times (i+j+m+n+5) \leq 50$.

[26] The cyclic peptide described in [22], in which $8 \leq g+h+k \times (m+n+p1+p2+q1+q2+5) \leq 50$.

[27] The cyclic peptide described in [23], in which $8 \leq v1+v2+w1+w2+t+u+k \times (i+j+m+n+5) \leq 50$.

[28] The cyclic peptide described in [24], in which $8 \leq v1+v2+w1+w2+t+u+k \times (m+n+p1+p2+q1+q2+5) \leq 50$.

[29] The cyclic peptide described in [22], [24], [26], or [28], in which the amino acid having a carboxy group on a side chain is at least one kind of amino acid selected from the group consisting of L-aspartic acid, D-aspartic acid, L-glutamic acid, D-glutamic acid, L-homoglutamic acid, and D-homoglutamic acid, in a case where one of $X^a$ and $X^b$ represents an amino acid residue derived from L-cysteine or D-cysteine, the amino acid, other than L-serine, D-serine, L-homoserine, and D-homoserine, having a hydroxy group on a side chain is at least one kind of amino acid selected from the group consisting of L-tyrosine, D-tyrosine, L-threonine, D-threonine, L-allothreonine, and D-allothreonine, and in a case where one of $X^a$ and $X^b$ represents an amino acid residue derived from L-cysteine or D-cysteine, the amino acid, other than L-serine and D-serine, having a hydroxy group on a side chain is at least one kind of amino acid selected from the group consisting of L-homoserine, D-homoserine, L-tyrosine, D-tyrosine, L-threonine, D-threonine, L-allothreonine, and D-allothreonine.

[30] The cyclic peptide described in [22], [24], [26], or [28], in which the amino acid having a carboxy group on a side chain is L-aspartic acid, and the amino acid, other than L-serine, D-serine, L-homoserine, and D-homoserine, having a hydroxy group on a side chain and the amino acid residue derived from the amino acid, other than L-serine and D-serine, having a hydroxy group on a side chain are L-threonine.

[31] The cyclic peptide described in [23], [24], [27], or [28], in which the immobilizing functional group is an amino group or a thiol group.

[32] The cyclic peptide described in [23], [24], [27], or [28], in which the amino acid, other than L-serine, D-serine, L-homoserine, D-homoserine, L-arginine, and D-arginine, having an immobilizing functional group on a side chain and the amino acid residue derived from the amino acid, other than L-serine and D-serine, having an immobilizing functional group on a side chain are at least one kind of amino acid selected from the group consisting of L-lysine, D-lysine, L-cysteine, D-cysteine, L-homocysteine, and D-homocysteine.

[33] The cyclic peptide described in any one of [21] to [32], in which $X^a$ is an amino acid residue derived from an amino acid having a chloroacetyl group on a side chain, selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, and N-ε-chloroacetyl-D-lysine, $X^b$ is an amino acid residue derived from L-cysteine or D-cysteine or an amino acid residue derived from L-penicillamine or D-penicillamine, and $X^a$ and $X^b$ are bonded to each other through a thioether bond.

[34] The cyclic peptide described in any one of [21] to [32] in which $X^a$ is an amino acid residue derived from L-cysteine or D-cysteine or an amino acid residue derived from L-penicillamine or D-penicillamine, $X^b$ is an amino acid residue derived from an amino acid having a chloroacetyl group on a side chain, selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino] butanoic acid, N-δ-chloroacetyl-L-ornithine, N-δ-chloroacetyl-D-omithine, N-ε-chloroacetyl-L-lysine, and N-ε-chloroacetyl-D-lysine, and $X^a$ and $X^b$ are bonded to each other through a thioether bond.

[35] The cyclic peptide described in any one of [21] to [34], in which the partial amino acid sequence $X_m\text{-}X^1\text{-}X^2\text{-}X^3\text{-}X_n$ in Formula (I'), (I'A), (I'B), or (I'C) and an amino acid sequence (SEQ ID NO: 1) represented by Formula (1) share sequence homology equal to or higher than 70%.

$$\text{A-Y-H-L-G-E-L-V-W} \tag{1}$$

In Formula (1), A represents an L-alanine residue; Y represents an L-tyrosine residue; H represents an L-histidine residue; L represents an L-leucine residue; G represents a glycine residue; E represents an L-glutamic acid residue; V represents an L-valine residue; and W represents an L-tryptophan residue.

[36] The cyclic peptide described in any one of [21] to [35], in which in Formula (I'), (I'A), (I'B), or (I'C), $k=1$.

[37] The cyclic peptide described in [21] that is represented by Formula (II').

$$R^N\text{-}X_{v0}\text{-}X^6_{r0}\text{-}X_{e0}\text{-}X^4_{r0}\text{-}X_{p0}\text{-}X^a\text{-}A\text{-}Y\text{-}H\text{-}X^8\text{-}G\text{-}E\text{-}L\text{-}V\text{-}W\text{-}X^b\text{-}X_{q0}\text{-}X^5_{s0}\text{-}X_{f0}\text{-}X^7_{u0}\text{-}X_{w0}\text{-}R^C \tag{II'}$$

In Formula (II'), $X^a$, $X^b$, X, $R^N$, and $R^C$ have the same definitions as those in Formula (I'); in a case where one of $X^a$ and $X^b$ represents an amino acid residue derived from L-cysteine or D-cysteine, $X^4$ and $X^5$ each independently represent an amino acid residue derived from an amino acid having a carboxy group on a side chain or an amino acid residue derived from an amino acid, other than L-serine, D-serine, L-homoserine, and D-homoserine, having a hydroxy group on a side chain, in a case where one of $X^a$ and $X^b$ represents an amino acid residue derived from L-penicillamine or D-penicillamine, $X^4$ and $X^5$ each independently represent an amino acid residue derived from an amino acid having a carboxy group on a side chain or an amino acid residue derived from an amino acid, other than L-serine and D-serine, having a hydroxy group on a side chain, and in a case where there is a plurality of $X^4$'s or $X^5$'s, the plurality of $X^4$'s or $X^5$'s may be the same as or different from each other; in a case where one of $X^a$ and $X^b$ represents an amino acid residue derived from L-cysteine or D-cysteine, $X^6$ and $X^7$ each independently represent an amino acid residue derived from an amino acid, other than L-serine, D-serine, L-homoserine, D-homoserine, L-arginine, and D-arginine, having an immobilizing functional group on a side chain or each independently represent an amino acid residue derived from an amino acid having an immobilizing functional group on a side chain, in a case where one of $X^a$ and $X^b$ represents an amino acid residue derived from L-penicillamine or D-penicillamine, $X^6$ and $X^7$ each independently represent an amino acid residue derived from an amino acid, other than L-serine and D-serine, having an immobilizing functional group on a side chain, and in a case where there is a plurality of $X^6$'s or $X^7$'s, the plurality of $X^6$'s or $X^7$'s may be the same as or different from each other; in a case where one of $X^a$ and $X^b$ represents an amino acid residue derived from L-cysteine or D-cysteine, $X^8$ represents an L-leucine residue or a D-leucine residue, in a case where one of $X^a$ and $X^b$ represents an amino acid residue derived from L-penicillamine or D-penicillamine, $X^8$ represents an L-leucine residue, a D-leucine residue, an L-arginine residue, or a D-arginine residue; e0 and f0 each represent an integer satisfying 0≤e0≤10 and 0≤f0≤10; p0 and q0 each represent an integer satisfying 0≤p0≤5 and 0≤q0≤5; r0 and s0 each represent an integer satisfying 0≤r0≤5 and 0≤s0≤5; t0 and u0 each represent an integer satisfying 0≤t0≤5 and 0≤u0≤5; v0 and w0 each represent an integer satisfying 0≤v0≤5 and 3≤w0≤5; p0, q0, r0, s0, t0, u0, v0, and w0 satisfy 0≤p0+q0+r0+s0+t0+u0+v0+w0≤39; A represents an L-alanine residue or a D-alanine residue; Y represents an L-tyrosine residue or a D-tyrosine residue; H represents an L-histidine residue or a D-histidine residue; G represents a glycine residue; E represents an L-glutamic acid residue or a D-glutamic acid residue; L represents an L-leucine residue; V represents an L-valine residue; and W represents an L-tryptophan residue.

[38] The cyclic peptide described in [37], in which $X^6$ and $X^7$ each independently represent an amino acid residue derived from an amino acid selected from the group consisting of L-lysine, D-lysine, L-cysteine, D-cysteine, L-homocysteine, and D-homocysteine.

[39] The cyclic peptide described in [37] or [38], in which $X^a$ is an amino acid residue derived from an amino acid having a chloroacetyl group on a side chain selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, and N-ε-chloroacetyl-D-lysine, $X^b$ is an amino acid residue derived from L-cysteine or D-cysteine or an amino acid residue derived from L-penicillamine or D-penicillamine, and $X^a$ and $X^b$ are bonded to each other through a thioether bond.

[40] The cyclic peptide described in [37] or [38], in which $X^a$ is an amino acid residue derived from L-cysteine or D-cysteine or an amino acid residue derived from L-penicillamine or D-penicillamine, $X^b$ is an amino acid residue derived from an amino acid having a chloroacetyl group on a side chain selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, and N-ε-chloroacetyl-D-lysine, and $X^a$ and $X^b$ are bonded to each other through a thioether bond.

[41] The cyclic peptide described in any one of [1] to [40] that is an antibody binding ligand.

[42] The cyclic peptide described in any one of [1] to [40] that is a linker for labeling antibodies.

[43] The cyclic peptide described in any one of [1] to [40] that is a linker for antibody drug conjugates.

[44] The cyclic peptide described in any one of [1] to [40] that is a drug carrier.

[45] An affinity chromatography support comprising a water-insoluble support and the cyclic peptide described in any one of [1] to [40], in which the water-insoluble support and the cyclic peptide are directly or indirectly bonded to each other.

[46] A labeled antibody comprising an antibody, a labeling compound, and the cyclic peptide described in any one of [1] to [40], in which the antibody and the labeling compound are bonded to each other through the cyclic peptide.

[47] An antibody drug conjugate comprising an antibody, a drug, and the cyclic peptide described in any one of [1] to [40], in which the antibody and the drug are bonded to each other through the cyclic peptide.

[48] The antibody drug conjugate described in [47], in which the drug is a drug having undergone liposomization, polymer micellization, or PEGylation.

[49] A pharmaceutical preparation comprising a drug and the cyclic peptide described in any one of [1] to [40], in which the drug and the cyclic peptide are directly or indirectly bonded to each other.

[50] The pharmaceutical preparation described in [49], in which the drug is a drug having undergone liposomization, polymer micellization, or PEGylation.

According to the present invention there are provided a cyclic peptide having excellent antibody binding properties and improved chemical resistance, an affinity chromatography support, a labeled antibody, an antibody drug conjugate, and a pharmaceutical preparation.

DESCRIPTION OF THE PREFERRED EMBODIMENTS

[Cyclic Peptide of Present Invention]
First, the characteristics of the present invention that are not found in the related art will be described.

U.S. Pat. No. 2004/0087765, WO2013/027796A, and JP2007-289200A describe cyclic peptides cyclized by forming a disulfide bond between two cysteine residues. According to the results of evaluating the relative binding activity and the chemical resistance in Comparative Example 2 which will be described later, although the antibody binding properties of the cyclic peptides cyclized by forming a disulfide bond between two cysteine residues are excellent, the chemical resistance thereof is poor, and hence a desired performance cannot be obtained.

U.S. Pat. No. 2004/0087765 describes a cyclic peptide cyclized by forming an amide bond between two amino acid residues through a reaction between a side-chain amino group and a side-chain carboxy group. JP2007-289200A describes a cyclic peptide cyclized by forming a lactam bond (amide bond) between an N-terminal amino group or a side-chain amino group and a side-chain carboxy group. According to the results of evaluating the relative binding activity and the chemical resistance in Comparative Example 1 which will be described later, although the chemical resistance of the cyclic peptide cyclized by the amide bond between a side-chain amino group and a side-chain carboxy group is improved, the antibody binding properties thereof are poor, and hence a desired performance cannot be obtained.

On the contrary, in the present invention, because the constitutions which will be described later are adopted, a cyclic peptide having excellent antibody binding properties and improved chemical resistance could be obtained.

In the present specification, in a case where "to" is used for a range of numerical values, the numerical values listed on the left and right sides of "to" are included in the range of numerical values.

<Amino Acid and Amino Acid Residue>

In the present invention, in principle, amino acids are described using names, codes, and the like adopted by INTERNATIONAL UNION OF PURE AND APPLIED CHEMISTRY and INTERNATIONAL UNION OF BIOCHEMISTRY AND MOLECULAR BIOLOGY IUPAC-IUB Joint Commission on Biochemical Nomenclature (JCBN). Furthermore, amino acid residues are described using the codes of amino acids from which the amino acid residues are derived. The amino acid residues include N-terminal amino acids (N-terminal residues) and C-terminal amino acids (C-terminal residues).

Unless otherwise specified, the amino acid sequence (referred to as "primary structure") of a peptide or a protein is described by aligning amino acid residues in a line, such that the left end of the line becomes the N-terminal and the right end of the line becomes the C-terminal. In a case where an amino acid residue in the amino acid sequence of a peptide or a protein is identified, including the position thereof, sometimes a number showing which position the amino acid residue occupies from the N-terminal side is placed on the right side of the code of the amino acid residue. For example, the second L-lysine from the N-terminal is described as Lys2 in some cases.

In a case where an amino acid is described using its name, and the amino acid includes isomers having an enantiomeric relationship, that is, in a case where the amino acid includes an L-isomer and a D-isomer, except for a case where the L-isomer and the D-isomer are clearly differentiated from each other, the amino acid represents the L-isomer in principle. For example, "isoleucine" represents "L-isoleucine", and the enantiomer of "isoleucine" represents "D-isoleucine". The same is true for amino acid residues.

In a case where an amino acid is described using its code (three-letter code or one-letter code), and the amino acid includes isomers having an enantiomeric relationship, that is, in a case where the amino acid includes an L-isomer and a D-isomer, except for a case where the L-isomer and the D-isomer are clearly differentiated from each other, the amino acid represents the L-isomer in principle. Here, "X" representing any amino acid is not limited thereto. For example, "Lys" and "L-Lys" both represent "L-lysine", and "D-Lys" represents "D-lysine". The same is true for amino acid residues.

In a case where an amino acid is described using its name, and the amino acid includes isomers having a diastereomeric relationship, the isomers are not included in the amino acid specified by its name. A diastereomer is described using a prefix "allo" and regarded as a different kind of amino acid. For example, "threonine" and "L-threonine" do not include "L-allothreonine", and "D-threonine" does not include "D-allothreonine". The same is true for amino acid residues.

Table 1 shows the names and the codes (one-letter code and three-letter code) of amino acids having officially recognized one-letter codes and three-letter codes.

TABLE 1

| One-letter code | Three-letter code | Name |
|---|---|---|
| A | Ala | L-alanine |
| B | Asx | L-aspartic acid or L-asparagine |
| C | Cys | L-cysteine |
| D | Asp | L-aspartic acid |
| E | Glu | L-glutamic acid |
| F | Phe | L-phenylalanine |
| G | Gly | Glycine |
| H | His | L-histidine |
| I | Ile | L-isoleucine |
| K | Lys | L-lysine |
| L | Leu | L-leucine |
| M | Met | L-methionine |
| N | Asn | L-asparagine |
| O | Pyl | L-pyrrolysine |
| P | Pro | L-proline |
| Q | Gln | L-glutamine |
| R | Arg | L-arginine |
| S | Ser | L-serine |
| T | Thr | L-threonine |
| U | Sec | L-selenocysteine |
| V | Val | L-valine |
| W | Trp | L-tryptophan |
| X | Xaa | Any amino acid |
| Y | Tyr | L-tyrosine |
| Z | Glx | L-glutamic acid or L-glutamine |

The amino acids are not limited to those listed in Table 1, and the amino acids referred to as unusual amino acid can also be used. Examples of unusual amino acids are listed in Table 2 shown below, but the present invention is not limited thereto.

TABLE 2

| Three-letter code | Name |
|---|---|
| Aad | Homoglutamic acid |
| βAad | 3-Aminoadipic acid |
| Abu | 2-Aminobutanoic acid |
| A$_2$bu | 2,4-Diaminobutanoic acid |
| Ahx | 2-Aminohexanoic acid |
| Ahe | 2-Aminoheptanoic acid |
| Aib | 2-Aminoisobutyric acid |
| εAhx | 6-Aminohexanoic acid |
| βAla | β-Alanine |
| Ape | 2-Aminopentanoic acid |
| A$_2$pr | 2,3-Diaminopropanoic acid |
| Apm | 2-Aminopimelic acid |
| A$_2$pm | 2,6-Diaminopimelic acid |

TABLE 2-continued

| Three-letter code | Name |
| --- | --- |
| Cit | Citrulline |
| Cya | Cysteic acid |
| Dbu | 2,4-Diaminobutanoic acid |
| Dpm | 2,6-Diaminopimelic acid |
| Pen | Penicillamine |
| Dpr | 2,3-Diaminopropanoic acid |
| Gla | 4-Carboxyglutamic acid |
| Glp | 5-Oxoproline |
| Hcy | Homocysteine |
| Hse | Homoserine |
| Hsl | Homoserine lactone |
| 5Hyl | 5-Hydroxylysine (Hyl) |
| aHyl | allo-Hydroxylysine |
| 3Hyp | 3-Hydroxyproline |
| 4Hyp | 4-Hydroxyproline |
| aIle | allo-Isoleucine |
| Nle | Norleucine |
| Nva | Norvaline |
| Orn | Ornithine |
| Sar | Sarcosine |
| aThr | allo-Threonine |
| Thx | Thyroxine |

<Structure of Cyclic Peptide (I) of Present Invention>

Hereinafter, the cyclic peptide of the present invention will be specifically described.

The cyclic peptide of the present invention is a cyclic peptide represented by Formula (I).

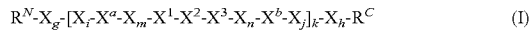

In Formula (I), for example, $X_n$ means that n X's are linked to each other. In other words, $X_n$ means $-(X)_n-$. $X_g$, $X_h$, $X_i$, $X_j$, and $X_m$ mean the same thing as $X_n$.

<<Cyclic Portion, Linear Portion, Cross-Linked Portion, and Antibody Binding Portion>>

Regarding the cyclic peptide of the present invention, in a polypeptide chain, a ring portion closed by cross-linking is referred to as a cyclic portion, and a portion which is not included in the cyclic portion is referred to as a linear portion. Furthermore, in the cyclic portion, a portion forming a cross-linked structure in the molecule of the cyclic peptide of the present invention is referred to as a cross-linked portion, and a portion greatly favoring the antibody binding properties of the cyclic peptide of the present invention is referred to as an antibody binding portion.

In the cyclic peptide represented by Formula (I), "$X^a$-$X_m$-$X^1$-$X^2$-$X^3$-$X_n$-$X^b$" is a cyclic portion, "$X_g$", "$X_h$", "$X_i$", and "$X_j$" are linear portions, "$X^a$" and "$X^b$" are cross-linked portions, and "$X^1$-$X^2$-$X^3$" is an antibody binding portion.

In Formula (1), $[X_i$-$X^a$-$X_m$-$X^1$-$X^2$-$X^3$-$X_n$-$X^b$-$X_j]$ is referred to as a repeating portion in some cases.

<<N-Terminal Group>>

In Formula (I), $R^N$ represents an N-terminal group.

Examples of the N-terminal group include an amino group, and the amino group may have undergone N-terminal modification such as N-acetylation, N-formylation, or N-acylation.

<<C-Terminal Group>>

In Formula (I), $R^C$ represents a C-terminal group.

Examples of the C-terminal group include a carboxy group, and the carboxy group may have undergone C-terminal modification such as amidation.

<<$X^1$, $X^2$, and $X^3$>>

In Formula (I), $X^1$ is an L-leucine residue, an L-isoleucine residue, an L-methionine residue, an L-lysine residue, or an L-arginine residue. $X^1$ is preferably an L-leucine residue or an L-isoleucine residue, and more preferably an L-leucine residue.

In Formula (I), $X^2$ is an L-valine residue or an L-isoleucine residue, and preferably an L-valine residue.

In Formula (I), $X^3$ is an L-tryptophan residue.

<<$X^a$ and $X^b$>>

In Formula (I), $X^a$ and $X^b$ are as explained in first to fourth embodiments described below.

First Embodiment

In Formula (I), $X^a$ and $X^b$ each independently represent an amino acid residue derived from an amino acid, other than L-cysteine and D-cysteine, having a thiol group on a side chain, and are bonded to each other through a disulfide bond.

((Type of Amino Acid and Amino Acid Residue))

The amino acid, other than L-cysteine and D-cysteine, having a thiol group on a side chain is not particularly limited as long as it is an amino acid, other than L-cysteine and D-cysteine, having a thiol group on a side chain. Examples of the amino acid include an amino acid represented by the following formula.

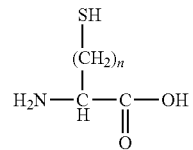

In the above formula, n is an integer equal to or greater than 2. n is preferably an integer satisfying 2≤n≤4, more preferably an integer satisfying 2≤n≤3, and even more preferably 2.

The amino acid represented by the above formula may be an L-isomer or a D-isomer, and is preferably an L-isomer.

Specifically, examples of the amino acid, other than L-cysteine and D-cysteine, having a thiol group on a side chain include L-homocysteine, D-homocysteine, L-bishomocysteine, D-bishomocysteine, and the like, but the amino acid is not limited to these.

The amino acid, other than L-cysteine and D-cysteine, having a thiol group on a side chain is preferably L-homocysteine or D-homocysteine, and more preferably L-homocysteine.

Examples of amino acid residues derived from the amino acid, other than L-cysteine and D-cysteine, having a thiol group on a side chain include an amino acid residue represented by the following formula.

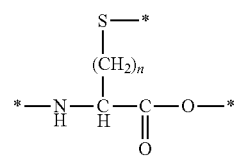

In the above formula, n is an integer equal to or greater than 2. n is preferably an integer satisfying 2≤n≤4, more preferably an integer satisfying 2≤n≤3, and even more preferably 2; and * represents a binding point.

The amino acid residue represented by the above formula may be derived from an L-amino acid or a D-amino acid, and is preferably derived from an L-amino acid.

Specifically, examples of the amino acid residue derived from an amino acid, other than L-cysteine and D-cysteine, having a thiol group on a side chain include amino acid residues derived from L-homocysteine, D-homocysteine, L-bishomocysteine, D-bishomocysteine, and the like, but the amino acid residue is not limited to these.

The amino acid residue derived from the amino acid, other than L-cysteine and D-cysteine, having a thiol group on a side chain is preferably an amino acid residue derived from L-homocysteine or D-homocysteine, and more preferably an amino acid residue derived from L-homocysteine.

((Disulfide Bond))

In the first embodiment of the cyclic peptide of the present invention, between $X^a$ and $X^b$, a cross-linked structure is formed by a disulfide bond formed between side-chain disulfide groups. That is, a disulfide bond is formed between a side-chain thiol group of a first amino acid residue, which is derived from an amino acid, other than L-cysteine and D-cysteine, having a thiol group on a side chain, and a side-chain thiol group of a second amino acid residue derived from an amino acid, other than L-cysteine and D-cysteine, having a thiol group on a side chain.

The following formula shows an example of the cross-linked structure formed by the formation of a disulfide bond between side-chain thiol groups of two amino acid residues derived from amino acids, other than L-cysteine and D-cysteine, having a thiol group on a side chain.

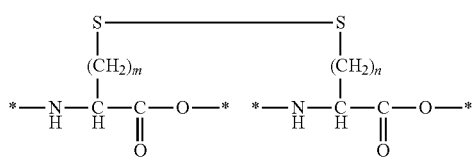

In the above formula, m is an integer equal to or greater than 2, preferably an integer satisfying $2 \le m \le 4$, more preferably an integer satisfying $2 \le m \le 3$, and even more preferably 2; n is an integer equal to or greater than 2, preferably an integer satisfying $2 \le n \le 4$, more preferably an integer satisfying $2 \le n \le 3$, and even more preferably 2; it is particularly preferable that m=n=2; and * represents a binding point.

Second Embodiment

In Formula (I), one of $X^a$ and $X^b$ represents an amino acid residue derived from an amino acid, other than L-cysteine, D-cysteine, L-penicillamine, and D-penicillamine, having a thiol group on a side chain and the other represents an amino acid residue derived from an amino acid having a haloacetyl group on a side chain, and $X^a$ and $X^b$ are bonded to each other through a thioether bond.

((Type of Amino Acid and Amino Acid Residue))

The amino acid, other than L-cysteine, D-cysteine, L-penicillamine, and D-penicillamine, having a thiol group on a side chain is not particularly limited as long as it is an amino acid, other than L-cysteine, D-cysteine, L-penicillamine, and D-penicillamine, having a thiol group on a side chain. Examples thereof include an amino acid represented by the following formula.

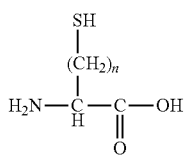

In the above formula, n is an integer equal to or greater than 2, preferably an integer satisfying $2 \le n \le 4$, more preferably an integer satisfying $2 \le n \le 3$, and even more preferably 2.

The amino acid represented by the above formula may be an L-isomer or a D-isomer, and is preferably an L-isomer.

Specifically, examples of the amino acid, other than L-cysteine, D-cysteine, L-penicillamine, and D-penicillamine, having a thiol group on a side chain include L-homocysteine, D-homocysteine, L-bishomocysteine, D-bishomocysteine, and the like, but the amino acid is not limited to these.

From the viewpoint of economic efficiency, the amino acid, other than L-cysteine, D-cysteine, L-penicillamine, and D-penicillamine, having a thiol group on a side chain is preferably L-homocysteine or D-homocysteine, and more preferably L-homocysteine.

Examples of the amino acid residue derived from the amino acid, other than L-cysteine, D-cysteine, L-penicillamine, and D-penicillamine, having a thiol group on a side chain include an amino acid residue represented by the following formula.

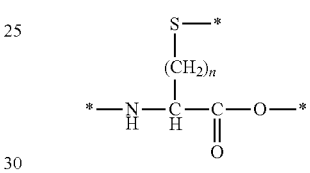

In the above formula, n is an integer equal to or greater than 2, preferably an integer satisfying $2 \le n \le 4$, more preferably an integer satisfying $2 \le n \le 3$, and even more preferably 2; and * represents a binding point.

The amino acid residue represented by the above formula may be derived from an L-amino acid or a D-amino acid, and is preferably derived from an L-amino acid.

Specifically, examples of the amino acid residue derived from the amino acid, other than L-cysteine, D-cysteine, L-penicillamine, and D-penicillamine, having a thiol group on a side chain include amino acid residues derived from L-homocysteine, D-homocysteine, L-bishomocysteine, D-bishomocysteine, and the like, but the amino acid residue is not limited to these.

From the viewpoint of economic efficiency, the amino acid residue derived from the amino acid, other than L-cysteine, D-cysteine, L-penicillamine, and D-penicillamine, having a thiol group on a side chain is preferably an amino acid residue derived from L-homocysteine or D-homocysteine, and more preferably an amino acid residue derived from L-homocysteine.

The amino acid having a haloacetyl group on a side chain is not particularly limited as long as it is an amino acid having a haloacetyl group on a side chain. Examples thereof include an amino acid represented by the following formula.

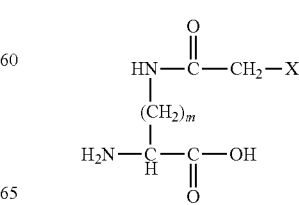

In the above formula, m is an integer equal to or greater than 1, preferably an integer satisfying 1≤m≤4, more preferably an integer satisfying 3≤m≤4, and even more preferably 4; and X represents a halogen atom, preferably represents a chlorine atom or a bromine atom, and more preferably represents a chlorine atom.

The amino acid represented by the above formula may be an L-isomer or a D-isomer, and is preferably an L-isomer.

In a case where n=1, the above formula represents $N^3$-haloacetyl-2,3-diaminopropanoic acid[2-amino-3-[(2-haloacetyl)amino]propanoic acid]; in a case where n=2, the above formula represents $N^4$-haloacetyl-2,4-diaminobutanoic acid[2-amino-4-[(2-haloacetyl)amino]butanoic acid]; in a case where n=3, the above formula represents N-δ-haloacetyl ornithine; and in a case where n=4, the above formula represents N-ε-haloacetyl lysine.

Here, the amino acid having a haloacetyl group on a side chain is not limited to these.

Examples of the amino acid residue derived from the amino acid having a haloacetyl group on a side chain include an amino acid residue represented by the following formula.

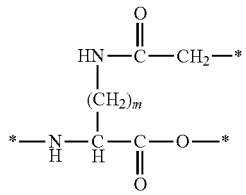

In the above formula, m is an integer equal to or greater than 1, preferably an integer satisfying 1≤m≤4, more preferably an integer satisfying 3≤m≤4, and even more preferably 4; X represents a halogen atom, preferably represents a chlorine atom or a bromine atom, and more preferably represents a chlorine atom; and * represents a binding point.

The amino acid residue represented by the above formula may be derived from an L-amino acid or a D-amino acid, and is preferably derived from an L-amino acid.

Specifically, examples of the amino acid residue derived from the amino acid having a haloacetyl group on a side chain include amino acid residues derived from (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, N-ε-chloroacetyl-D-lysine, and the like, but the amino acid residue is not limited to these.

From the viewpoint of economic efficiency, the amino acid residue derived from the amino acid having a haloacetyl group on a side chain is preferably an amino acid residue derived from N-δ-chloroacetyl-L-ornithine, N-δ-chloroacetyl-D-ornithine, N-ε-chloroacetyl-L-lysine, or N-ε-chloroacetyl-D-lysine, and more preferably an amino acid residue derived from N-ε-chloroacetyl-D-lysine.

((Thioether Bond))

In the second embodiment of the cyclic peptide of the present invention, between $X^a$ and $X^b$, a cross-linked structure is formed by a thioether bond formed between the side-chain thiol group and the side-chain haloacetyl group. That is, the thioether bond is formed between a thiol group of a first amino acid residue derived from an amino acid, other than L-cysteine, D-cysteine, L-penicillamine, and D-penicillamine, having a thiol group on a side chain, and a haloacetyl group of a second amino acid residue which is derived from an amino acid having a haloacetyl group on a side chain.

The following formulae show examples of the thioether bond formed between the side-chain thiol group of the amino acid residue, which is derived from the amino acid, other than L-cysteine, D-cysteine, L-penicillamine, and D-penicillamine, having a thiol group on a side chain and the side-chain haloacetyl group of the amino acid residue derived from the amino acid having a haloacetyl group on a side chain.

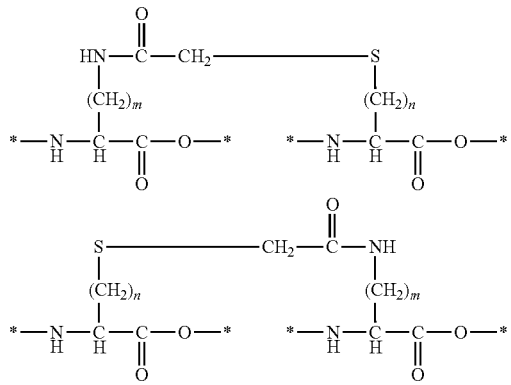

In the above formulae, m is an integer equal to or greater than 1, preferably an integer satisfying 1≤m≤4, more preferably an integer satisfying 3≤m≤4, and even more preferably 4; n is an integer equal to or greater than 2, preferably an integer satisfying 2≤n≤4, more preferably an integer satisfying 2≤n≤3, and even more preferably 2; it is particularly preferable that m=4 and n=2; and * represents a binding point.

Regarding $X^a$ and $X^b$, $X^a$ may be an amino acid residue derived from an amino acid having a haloacetyl group on a side chain, and $X^b$ may be an amino acid residue derived from an amino acid, other than L-cysteine, D-cysteine, L-penicillamine, and D-penicillamine, having a thiol group on a side chain; or $X^a$ may be an amino acid residue derived from amino acid, other than L-cysteine, D-cysteine, L-penicillamine, and D-penicillamine, having a thiol group on a side chain and $X^b$ may be an amino acid residue derived from an amino acid having a haloacetyl group on a side chain.

A thioether bond is known to be a bond more stable than a disulfide bond.

Third Embodiment

In Formula (I), one of $X^a$ and $X^b$ represents an amino acid residue derived from L-cysteine or D-cysteine and the other represents an amino acid residue derived from an amino acid having a haloacetyl group on a side chain, and $X^a$ and $X^b$ are bonded to each other through a thioether bond.

((Type of Amino Acid and Amino Acid Residue))

The amino acid having a haloacetyl group on a side chain is not particularly limited as long as it is an amino acid having a haloacetyl group on a side chain. Examples thereof include an amino acid represented by the following formula.

Fourth Embodiment

In Formula (I), one of $X^a$ and $X^b$ represents an amino acid residue derived from L-penicillamine or D-penicillamine and the other represents an amino acid residue derived from an amino acid having a haloacetyl group on a side chain, and $X^a$ and $X^b$ are bonded to each other through a thioether bond.

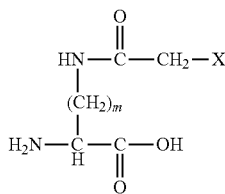

In the above formula, m is an integer equal to or greater than 1, preferably an integer satisfying $1 \leq m \leq 4$, more preferably an integer satisfying $3 \leq m \leq 4$, and even more preferably 4; and X represents a halogen atom, preferably represents a chlorine atom or a bromine atom, and even more preferably represents a chlorine atom.

The amino acid represented by the above formula may be an L-isomer or a D-isomer, and is preferably an L-isomer.

In a case where n=1, the above formula represents $N^3$-haloacetyl-2,3-diaminopropanoic acid[2-amino-3-[(2-haloacetyl)amino]propanoic acid]; in a case where n=2, the above formula represents $N^4$-haloacetyl-2,4-diaminobutanoic acid[2-amino-4-[(2-haloacetyl)amino]butanoic acid]; in a case where n=3, the above formula represents N-δ-haloacetyl ornithine; and in a case where n=4, the above formula represents N-ε-haloacetyl lysine.

Here, the amino acid having a haloacetyl group on a side chain is not limited to these.

Examples of the amino acid residue derived from the amino acid having a haloacetyl group on a side chain include an amino acid residue represented by the following formula.

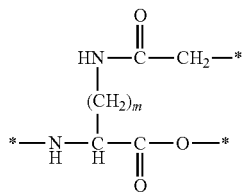

In the above formula, m is an integer equal to or greater than 1, preferably an integer satisfying $1 \leq m \leq 4$, more preferably an integer satisfying $3 \leq m \leq 4$, and even more preferably 4; X represents a halogen atom, more preferably represents a chlorine atom or a bromine atom, and even more preferably represents a chlorine atom; and * represents a binding point.

The amino acid residue represented by the above formula may be derived from an L-amino acid or a D-amino acid, and is preferably derived from an L-amino acid.

Specifically, examples of the amino acid residue derived from the amino acid having a haloacetyl group on a side chain include amino acid residues derived from (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, N-ε-chloroacetyl-D-lysine, and the like, but the amino acid residue is not limited to these.

From the viewpoint of economic efficiency, the amino acid residue derived from the amino acid having a haloacetyl group on a side chain is preferably an amino acid residue derived from N-δ-chloroacetyl-L-ornithine, N-δ-chloroacetyl-D-ornithine, N-ε-chloroacetyl-L-lysine, or N-ε-chloroacetyl-D-lysine, and more preferably an amino acid residue derived from N-ε-chloroacetyl-D-lysine.

((Thioether Bond))

In the third embodiment of the cyclic peptide of the present invention, between $X^a$ and $X^b$, a cross-linked structure is formed by a thioether bond formed between the side-chain thiol group and the side-chain haloacetyl group. That is, the thioether bond is formed between a thiol group of a first amino acid residue derived from L-cysteine or D-cysteine and a haloacetyl group of a second amino acid residue derived from an amino acid having a haloacetyl group on a side chain.

The following formulae show examples of the thioether bond formed between the side-chain thiol group of the amino acid residue derived from L-cysteine or D-cysteine and the side-chain haloacetyl group of the amino acid residue derived from the amino acid having a haloacetyl group on a side chain.

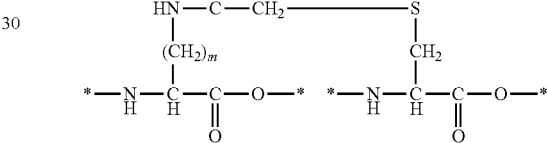

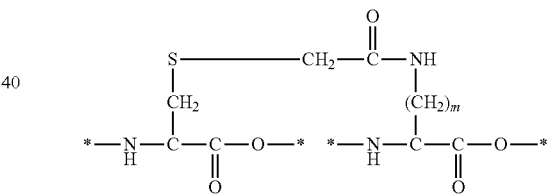

In the above formulae, m is an integer equal to or greater than 1, preferably an integer satisfying $1 \leq m \leq 4$, more preferably an integer satisfying $3 \leq m \leq 4$, and even more preferably 4; and * represents a binding point.

Regarding $X^a$ and $X^b$, $X^a$ may be an amino acid residue derived from an amino acid having a haloacetyl group on a side chain, and $X^b$ may be an amino acid residue derived from L-cysteine or D-cysteine; or $X^a$ may be an amino acid residue derived from L-cysteine or D-cysteine, and $X^b$ may be an amino acid residue derived from an amino acid having a haloacetyl group on a side chain.

A thioether bond is known to be a bond more stable than a disulfide bond.

((Type of Amino Acid and Amino Acid Residue))

The amino acid having a haloacetyl group on a side chain is not particularly limited as long as it is an amino acid having a haloacetyl group on a side chain. Examples thereof include an amino acid represented by the following formula.

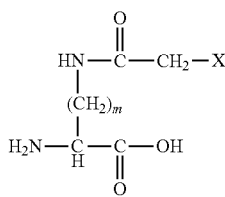

In the above formula, m is an integer equal to or greater than 1, preferably an integer satisfying $1 \leq m \leq 4$, more preferably an integer satisfying $3 \leq m \leq 4$, and even more preferably 4; and X represents a halogen atom, preferably represents a chlorine atom or a bromine atom, and more preferably represents a chlorine atom.

The amino acid represented by the above formula may be an L-isomer or a D-isomer, and is preferably an L-isomer.

In a case where n=1, the above formula represents $N^3$-haloacetyl-2,3-diaminopropanoic acid[2-amino-3-[(2-haloacetyl)amino]propanoic acid]; in a case where n=2, the above formula represents $N^4$-haloacetyl-2,4-diaminobutanoic acid[2-amino-4-[(2-haloacetyl)amino]butanoic acid]; in a case where n=3, the above formula represents N-δ-haloacetyl ornithine; and in a case where n=4, the above formula represents N-ε-haloacetyl lysine.

Here, the amino acid having a haloacetyl group on a side chain is not limited to these.

Examples of the amino acid residue derived from the amino acid having a haloacetyl group on a side chain include an amino acid residue represented by the following formula.

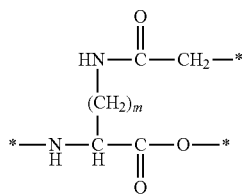

In the above formula, m is an integer equal to or greater than 1, preferably an integer satisfying $1 \leq m \leq 4$, more preferably an integer satisfying $3 \leq m \leq 4$, and even more preferably 4; X represents a halogen atom, preferably represents a chlorine atom or a bromine atom, and more preferably represents a chlorine atom; and * represents a binding point.

The amino acid residue represented by the above formula may be derived from an L-amino acid or a D-amino acid, and is preferably derived from an L-amino acid.

Specifically, examples of the amino acid residue derived from the amino acid having a haloacetyl group on a side chain include amino acid residues derived from (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, N-ε-chloroacetyl-D-lysine, and the like, but the amino acid residue is not limited to these.

From the viewpoint of economic efficiency, the amino acid residue derived from the amino acid having a haloacetyl group on a side chain is preferably an amino acid residue derived from N-δ-chloroacetyl-L-ornithine, N-δ-chloroacetyl-D-ornithine, N-ε-chloroacetyl-L-lysine, or N-ε-chloroacetyl-D-lysine, and more preferably an amino acid residue derived from N-ε-chloroacetyl-D-lysine.

((Thioether Bond))

In the fourth embodiment of the cyclic peptide of the present invention, between $X^a$ and $X^b$, a cross-linked structure is formed by a thioether bond formed between the side-chain thiol group and the side-chain haloacetyl group. That is, the thioether bond is formed between a thiol group of a first amino acid residue derived from L-penicillamine or D-penicillamine and a haloacetyl group of a second amino acid residue derived from an amino acid having a haloacetyl group on a side chain.

The following formulae show examples of the thioether bond formed between the side-chain thiol group of the amino acid residue derived from L-penicillamine or D-penicillamine and the side-chain haloacetyl group of the amino acid residue derived from the amino acid having a haloacetyl group on a side chain.

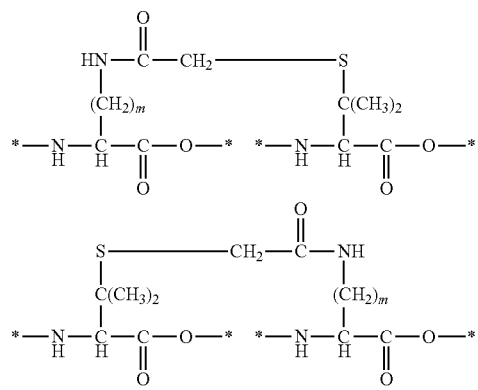

In the above formulae, m is an integer equal to or greater than 1, preferably an integer satisfying $1 \leq m \leq 4$, more preferably an integer satisfying $3 \leq m \leq 4$, and even more preferably 4; and * represents a binding point.

Regarding $X^a$ and $X^b$, $X^a$ may be an amino acid residue derived from an amino acid having a haloacetyl group on a side chain, and $X^b$ may be an amino acid residue derived from L-penicillamine or D-penicillamine; or $X^a$ may be an amino acid residue derived from L-penicillamine or D-penicillamine, and $X^b$ may be an amino acid residue derived from an amino acid having a haloacetyl group on a side chain.

A thioether bond is known to be a bond more stable than a disulfide bond.

<<$X_g$, $X_h$, $X_i$, $X_j$, $X_m$, and $X_n$>>

In Formula (I), $X_g$, $X_h$, $X_i$, $X_j$, $X_m$, and $X_n$ each represent g consecutive X's, h consecutive X's, i consecutive X's, j consecutive X's, m consecutive X's, and n consecutive X's.

In Formula (I), in a case where X represents an amino acid residue, and there is a plurality of X's, the plurality of X's may be the same as or different from each other.

In Formula (I), X is not particularly limited as long as it is an amino acid residue. X is preferably an amino acid residue derived from an amino acid selected from the group consisting of amino acids (excluding B, Z, and X) shown in Table 1 and amino acids shown in Table 2, and more preferably an amino acid residue derived from an amino acid selected from the group consisting of amino acids (excluding B, Z, and X) shown in Table 1. In a case where there is an enantiomer or a diastereomer of these amino acids, X may be an amino acid residue derived from the enantiomer or the diastereomer.

In Formula (I), g, h, i, and j each independently represent an integer equal to or greater than 0.

g preferably satisfies 0≤g≤20, more preferably satisfies 0≤g≤10, and even more preferably satisfies 0≤g≤5.

h preferably satisfies 0≤h≤20, more preferably satisfies 0≤h≤10, and even more preferably satisfies 0≤h≤5.

i preferably satisfies 0≤i≤20, more preferably satisfies 0≤i≤10, and even more preferably satisfies 0≤i≤5.

j preferably satisfies 0≤j≤20, more preferably satisfies 0≤j≤10, and even more preferably satisfies 0≤j≤5.

In Formula (I), m and n are integers satisfying 0≤m≤9 and 0≤n≤9. m and n satisfy 3≤m+n≤9, preferably satisfy 4≤m+n≤8, and more preferably satisfy 5≤m+n≤7.

<<Number of Amino Acid Residues in Cyclic Portion>>

In Formula (I), the number of amino acid residues [(m+n+5) residues] in the cyclic portion [$X^a$-$X_m$-$X^1$-$X^2$-$X^3$-$X_n$-$X^b$] is 8 to 14, preferably 9 to 13, and more preferably 10 to 12.

In a case where the number of amino acid residues in the cyclic portion is within the above range, the intramolecular strain of the cyclic peptide does not excessively increase, and the high-order structure such as α-helix is stabilized. Therefore, the antibody binding properties of the cyclic peptide of the present invention become excellent.

<<Number of Repeating Units>> k is an integer satisfying k≥1. k preferably satisfies 1≤k≤3, more preferably satisfies 1≤k≤2, and even more preferably satisfies k=1.

Although the number of repeating units is not particularly limited, the larger the number of repeating units, the more the cyclic portions can be included in the cyclic peptide. Accordingly, it is possible to improve the antibody binding properties of the cyclic peptide. The smaller the number of repeating units, the further the total number of amino acid residues can be reduced. Accordingly, it is possible to inhibit the antigenicity of the cyclic peptide. From the viewpoint the synthesis cost of the cyclic peptide, it is preferable that the number of amino acid residues and the number of repeating units are small.

In a case where k≥2, that is, in a case where the cyclic peptide represented by Formula (I) includes two or more repeating units [$X_i$-$X^a$-$X_m$-$X^1$-$X^2$-$X^3$-$X_n$-$X^b$-$X_j$], $X^1$, $X^2$, $X^3$, $X^a$, $X^b$, $X_i$, $X_j$, $X_m$, and $X_n$ in the repeating unit each may be the same as or different between the repeating units.

<<Total Number of Amino Acid Residues in Cyclic Peptide>>

The total number of amino acid residues in the cyclic peptide represented by Formula (I) is preferably 8 to 50, more preferably 9 to 40, even more preferably 10 to 30, and still more preferably 10 to 20.

That is, in Formula (I), g, h, i, j, m, n, and k preferably satisfy 8≤g+h+(i+j+m+n+5)×k≤50, more preferably satisfy 9≤g+h+(i+j+m+n+5)×k≤40, even more preferably satisfy 10≤g+h+(i+j+m+n+5)×k≤30, and still more preferably satisfy 10≤g+h+(i+j+m+n+5)×k≤20.

Generally, the larger the number of amino acid residues, the higher the manufacturing cost. Therefore, from the viewpoint of economic efficiency, it is preferable that the total number of amino acid residues is small.

<<Molecular Weight of Cyclic Peptide>>

The molecular weight of the cyclic peptide represented by Formula (I) is not particularly limited. However, from the viewpoint of antigenicity, the molecular weight of the cyclic peptide of the present invention is preferably about equal to or smaller than 5,000, more preferably about equal to or smaller than 4,000, even more preferably about equal to or smaller than 3,000, and most preferably about equal to or smaller than 2,000. "About" means that the molecular weight includes a margin of ±2%.

Exception in Third Embodiment

In the third embodiment of the present invention, X in Formula (I) represents an amino acid residue derived from an amino acid other than L-serine, D-serine, L-homoserine, D-homoserine, L-arginine, and D-arginine, and in a case where there is a plurality of X's, the plurality of X's may be the same as or different from each other.

In the third embodiment of the present invention, due to this difference, Formula (I) is referred to as Formula (I') in some cases.

Exception in Fourth Embodiment

In the fourth embodiment of the present invention, X in Formula (I) represents an amino acid residue derived from an amino acid other than L-serine and D-serine, and in a case where there is a plurality of X's, the plurality of X's may be the same as or different from each other.

In the fourth embodiment of the present invention, due to this difference, Formula (I) is referred to as Formula (I') in some cases.

<Structure of Cyclic Peptide (IA) of Present Invention>

The cyclic peptide of the present invention is preferably a cyclic peptide represented by Formula (IA).

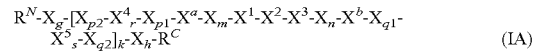

$$R^N\text{-}X_g\text{-}[X_{p2}\text{-}X^4_r\text{-}X_{p1}\text{-}X^a\text{-}X_m\text{-}X^1\text{-}X^2\text{-}X^3\text{-}X_n\text{-}X^b\text{-}X_{q1}\text{-}X^5_s\text{-}X_{q2}]_k\text{-}X_h\text{-}R^C \quad \text{(IA)}$$

In Formula (IA), all of $R^N$, $R^C$, $X^1$, $X^2$, $X^3$, $X^a$, $X^b$, $X_g$, $X_h$, $X_m$, $X_n$, X, g, h, m, n, and k have the same definitions as those in Formula (I).

In Formula (IA), similarly to $X_n$ in Formula (I), $X_n$ means that n X's are linked to each other. The same is true for $X_m$, $X_{p1}$, $X_{p2}$, $X_{q1}$, and $X_{q2}$.

In Formula (IA), $X^4_r$ and $X^5_s$ each mean that r $X^4$'s are linked to each other, and s $X^5$'s are linked to each other.

<<Cyclic Portion, Linear Portion, Cross-Linked Portion, and Antibody Binding Portion>>

In the cyclic peptide represented by Formula (IA), "$X_g$", "$X_h$", "$X_{p2}$-$X^4_r$-$X_{p1}$", and "$X_{q1}$-$X^5_s$-$X_{q2}$" are linear portions. The cyclic portion, the cross-linked portion, and the antibody binding portion are the same as those in the cyclic peptide represented by Formula (I).

In Formula (IA), [$X_{p2}$-$X^4_r$-$X_{p1}$-$X^a$-$X_m$-$X^1$-$X^2$-$X^3$-$X_n$-$X^b$-$X_{q1}$-$X^5_s$-$X_{q2}$] is a repeating unit.

<<$X^4_r$ and $X^5_s$>>

In Formula (IA), $X^4_r$ and $X^5_s$ each mean r consecutive $X^4$'s and s consecutive $X^5$'s.

In Formula (IA), $X^4$ and $X^5$ each independently represent an amino acid residue derived from an amino acid having a carboxy group on a side chain or an amino acid residue derived from an amino acid having a hydroxy group on a side chain.

In a case where there is a plurality of $X^4$'s or $X^5$'s, the plurality of $X^4$'s or $X^5$'s may be the same as or different from each other.

In Formula (IA), r and s each represent an integer satisfying 0≤r≤5, 0≤s≤5, and 1≤Max (r,s)≤5. r and s preferably each represent an integer satisfying 0≤r≤4, 0≤s≤4, and 1≤Max (r,s)≤4, and more preferably each represent an integer satisfying 0≤r≤3, 0≤s≤3, and 1≤Max (r,s)≤3.

Max (r,s) represents a larger one between two numbers represented by r and s in a case where r≠s and represents r or s in a case where r=s.

(Amino Acid Having Carboxy Group on Side Chain)

Examples of the amino acid having a carboxy group on a side chain include L-aspartic acid, D-aspartic acid, L-glutamic acid, D-glutamic acid, L-homoglutamic acid, D-homoglutamic acid, and the like.

(Amino Acid Having Hydroxy Group on Side Chain)

Examples of the amino acid having a hydroxy group on a side chain include L-serine, D-serine, L-homoserine, D-homoserine, L-tyrosine, D-tyrosine, L-threonine, D-threonine, L-allothreonine, D-allothreonine, and the like.

(Preferred Amino Acid Residues)

$X^4$ and $X^5$ preferably each independently represent an amino acid residue selected from the group consisting of an L-serine residue, a D-serine residue, an L-homoserine residue, a D-homoserine residue, an L-aspartic acid residue, a D-aspartic acid residue, an L-glutamic acid residue, a D-glutamic acid residue, an L-homoglutamic acid residue, a D-homoglutamic acid residue, an L-tyrosine residue, a D-tyrosine residue, an L-homotyrosine residue, a D-homotyrosine residue, an L-threonine residue, a D-threonine residue, an L-allothreonine residue, and a D-allothreonine residue, and more preferably each independently represent an amino acid residue selected from the group consisting of an L-aspartic acid residue, a D-aspartic acid residue, an L-threonine residue, and a D-threonine residue. It is even more preferable that $X^4$ represents an L-aspartic acid residue and $X^5$ represents an L-threonine residue.

It is considered that in a case where $X^4$ and $X^5$ each independently represent an amino acid residue derived from an amino acid having a carboxy group on a side chain or an amino acid residue derived from an amino acid having a hydroxy group on a side chain, due to a hydrogen bond and/or an electrostatic interaction, the interaction between the antibody binding portion of the cyclic portion and an antibody can become stronger, and hence the antibody binding properties are improved.

≤≤$X_{p1}$, $X_{p2}$, $X_{q1}$, and $X_{q2}$>>

In Formula (IA), $X_{p1}$, $X_{p2}$, $X_{q1}$, and $X_{q2}$ each represent p1 consecutive X's, p2 consecutive X's, q1 consecutive X's, and q2 consecutive X's.

In Formula (IA), p1, p2, q1, and q2 each independently represent an integer equal to or greater than 0.

p1 preferably satisfies 0≤p1≤20, more preferably satisfies 0≤p1≤10, even more preferably satisfies 0≤p1≤5, and still more preferably satisfies 0≤p1≤2.

p2 preferably satisfies 0≤p2≤20, more preferably satisfies 0≤p2≤10, even more preferably satisfies 0≤p2≤5, and still more preferably satisfies 0≤p2≤2.

q1 preferably satisfies 0≤q1≤20, more preferably satisfies 0≤q1≤10, even more preferably satisfies 0≤q1≤5, and still more preferably satisfies 0≤q1≤2.

q2 preferably satisfies 0≤q2≤20, more preferably satisfies 0≤q2≤10, even more preferably satisfies 0≤q2≤5, and still more preferably satisfies 0≤q2≤2.

<<Number of Amino Acid Residues in Cyclic Portion>>

In Formula (IA), the number of amino acid residues [(m+n+5) residues] in the cyclic portion [$X^a$-$X_m$-$X^1$-$X^2$-$X^3$-$X_n$-$X^b$] is 8 to 14, preferably 9 to 13, and more preferably 10 to 12, similarly to Formula (I).

In a case where the number of amino acid residues in the cyclic portion is within the above range, the intramolecular strain of the cyclic peptide does not excessively increase, and the high-order structure such as α-helix is stabilized. Therefore, the antibody binding properties of the cyclic peptide of the present invention become excellent.

<<Number of Repeating Units>>

In a case where k≥2, that is, in a case where the cyclic peptide represented by Formula (IA) includes two or more repeating units [$X_{p2}$-$X^4_r$-$X_{p1}$-$X^a$-$X_m$-$X^1$-$X^2$-$X^3$-$X_n$-$X^b$-$X_{q1}$-$X^5_s$-$X_{q2}$], $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in the repeating unit each may be the same or different between the repeating units.

<<Total Number of Amino Acid Residues in Cyclic Peptide>>

The total number of amino acid residues in the cyclic peptide represented by Formula (IA) is preferably 8 to 50, more preferably 9 to 40, even more preferably 10 to 30, and still more preferably 10 to 20.

That is, in Formula (IA), g, h, m, n, p1, p2, q1, q2, r, s, and k preferably satisfy 8≤g+h+(m+n+p1+p2+q1+q2+r+s+5)×k≤50, more preferably satisfy 9≤g+h+(m+n+p1+p2+q1+q2+r+s+5)×k≤40, even more preferably satisfy 10≤g+h+(m+n+p1+p2+q1+q2+r+s+5)×k≤30, and still more preferably satisfy 10≤g+h+(m+n+p1+p2+q1+q2+r+s+5)×k≤20.

Generally, the larger the number of amino acid residues, the higher the manufacturing cost. Therefore, from the viewpoint of economic efficiency, it is preferable that the total number of amino acid residues is small.

Exception in Third Embodiment

In the third embodiment of the present invention, X in Formula (IA) represents an amino acid residue derived from an amino acid other than L-serine, D-serine, L-homoserine, D-homoserine, L-arginine, and D-arginine, and in a case where there is a plurality of X's, the plurality of X's may be the same as or different from each other; $X^4$ and $X^5$ in Formula (IA) each independently represent "an amino acid residue derived from an amino acid having a carboxy group on a side chain" or "an amino acid residue derived from an amino acid, 'other than include L-serine, D-serine, L-homoserine, and D-homoserine', having a hydroxy group on a side chain", and in a case where there is a plurality of $X^4$'s or $X^5$'s, the plurality of $X^4$'s or $X^5$'s may be the same as or different from each other.

In the third embodiment of the present invention, due to these differences, Formula (IA) is referred to as Formula (I'A) in some cases.

Exception in Fourth Embodiment

In the fourth embodiment of the present invention, X in Formula (IA) represents an amino acid residue derived from an amino acid other than L-serine and D-serine, and in a case where there is a plurality of X's, the plurality of X's may be the same as or different from each other; $X^4$ and $X^5$ in Formula (IA) each independently represent "an amino acid residue derived from an amino acid having a carboxy group on a side chain" or "an amino acid residue derived from an amino acid, 'other than include L-serine and D-serine', having a hydroxy group on a side chain", and in a case where there is a plurality of $X^4$'s or $X^5$'s, the plurality of $X^4$'s or $X^5$'s may be the same as or different from each other.

In the fourth embodiment of the present invention, due to these differences, Formula (IA) is referred to as Formula (I'A) in some cases.

<Structure of Cyclic Peptide (IB) of Present Invention>
The cyclic peptide of the present invention is preferably a cyclic peptide represented by Formula (IB).

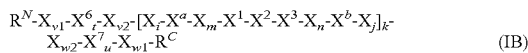
(IB)

In Formula (IB), all of $R^N$, $R^C$, $X^1$, $X^2$, $X^3$, $X^a$, $X^b$, $X_i$, $X_j$, $X_m$, $X_n$, X, i, j, m, n, and k have the same definitions as those in Formula (I).

In Formula (IB), similarly to $X_n$ in Formula (I), $X_n$ means that n X's are linked to each other. The same is true for $X_m$, $X_{v1}$, $X_{v2}$, $X_{w1}$, and $X_{w2}$.

In Formula (IB), $X^6_t$ and $X^7_u$ each mean that t $X^6$'s are linked to each other, and u $X^7$'s are linked to each other.

<<Cyclic Portion, Linear Portion, Cross-Linked Portion, and Antibody Binding Portion>>

In the cyclic peptide represented by Formula (IB), "$X_i$", "$X_j$", "$X_{v1}$-$X^6_t$-$X_{v2}$", and "$X_{w2}$-$X^7_u$-$X_{w1}$" are linear portions. The cyclic portion, the cross-linked portion, and the antibody binding portion are the same as those in the cyclic peptide represented by Formula (I).

In Formula (IB), $[X_i$-$X^a$-$X_m$-$X^1$-$X^2$-$X^3$-$X_n$-$X^b$-$X_j]$ is a repeating unit, similarly to Formula (I).

<<$X^6_t$ and $X^7_u$>>

In Formula (IB), $X^6_t$ and $X^7_u$ each represent t consecutive $X^6$'s and u consecutive $X^7$'s.

In Formula (IB), $X^6$ and $X^7$ each independently represent an amino acid residue derived from an amino acid having an immobilizing functional group on a side chain.

In a case where there is a plurality of $X^6$'s or $X^7$'s, the plurality of $X^6$'s or $X^7$'s may be the same as or different from each other.

In Formula (IB), t and u each represent an integer satisfying $0 \leq t \leq 5$, $0 \leq u \leq 5$, and $1 \leq Max (t,u) \leq 5$, preferably each represent an integer satisfying $0 \leq t \leq 4$, $0 \leq u \leq 4$, and $1 \leq Max (t,u) \leq 4$, and more preferably each represent an integer satisfying $0 \leq t \leq 3$, $0 \leq u \leq 3$, and $1 \leq Max (t,u) \leq 3$.

Max (t,u) represents a larger one between two numbers represented by t and u in a case where t≠u and represents t or u in a case where t=u.

(Immobilizing Functional Group)

The aforementioned "immobilizing functional group" is a functional group which can form a covalent bond by reacting with a functional group on a support (described later).

Examples of the immobilizing functional group include an amino group, a carboxy group, a hydroxy group, a thiol group, an aldehyde group (formyl group), a carbamoyl group, an azide group, an alkynyl group, and the like.

Examples of the combination of the immobilizing functional group that the cyclic peptide of the present invention has and the functional group on the support include an amino group and a carboxy group (amide bond forming reaction), an amino group and an aldehyde group (reductive amination reaction), an amino group and an epoxy group, a hydroxy group and an epoxy group, a carboxy group and a hydroxy group (ester bond forming reaction), a thiol group and a thiol group (disulfide bond), a thiol group and an epoxy group, an azide group and an alkynyl group (Huisgen cycloaddition reaction), and the like.

In a case where the immobilizing functional group that the cyclic peptide of the present invention has and the functional group on the support form a covalent bond by reacting with each other, the cyclic peptide of the present invention is immobilized on the support. At least some of the immobilizing functional groups that the cyclic peptide of the present invention has may form a covalent bond by reacting with the functional group on the support, and it is not necessary for all the immobilizing functional groups to react with the functional group on the support.

In the aforementioned amino acid having an immobilizing functional group on a side chain, the immobilizing functional group is preferably at least one kind of functional group selected from the group consisting of an amino group, a thiol group, and an aldehyde group, and more preferably at least one kind of functional group selected from the group consisting of an amino group and a thiol group.

(Amino Acid Having Immobilizing Functional Group on Side Chain)

The amino acid having an immobilizing functional group on a side chain is preferably at least one kind of amino acid selected from the group consisting of L-lysine, D-lysine, L-cysteine, D-cysteine, L-homocysteine, and D-homocysteine.

In a case where an amino group is used as the immobilizing functional group, the amino group can be bonded to a carboxy group on the support through an amide bond, and the cyclic peptide of the present invention as an affinity ligand can be easily immobilized.

In a case where a thiol group is used as the immobilizing functional group, the thiol group can be bonded to an epoxy group on the support through a covalent bond, and the cyclic peptide of the present invention as an affinity ligand can be easily immobilized.

Examples of the amino acid having an amino group on a side chain include L-lysine, D-lysine, and the like, and examples of the amino acid having a thiol group on a side chain include L-cysteine and D-cysteine. Because these amino acids are relatively cheap, the manufacturing cost of the cyclic peptide of the present invention can be reduced. Therefore, from the viewpoint of economic efficiency, these amino acids are preferable.

(Support)

In the present invention, "support" refers to a substrate on which the cyclic peptide of the present invention can be immobilized. The support has a functional group which can form a covalent bond by reacting with the immobilizing functional group that the cyclic peptide of the present invention has. The functional group is appropriately selected according to the immobilizing functional group.

(Material Constituting Support)

Examples of the material constituting the support include polysaccharides such as agarose, dextran, starch, cellulose, pullulan, chitin, chitosan, cellulose triacetate, and cellulose diacetate, derivatives of these, vinyl-based polymers such as polyacrylamide, polymethacrylamide, polyacrylate, polymethacrylate, polyalkyl vinyl ether, and polyvinyl alcohol, and the like. These materials may form a cross-linked structure because then mechanical strength can be secured. It is preferable that the support is formed of one kind of material or two or more kinds of materials among these.

The support is preferably porous, more preferably a porous film or a porous particle, and even more preferably a porous particle.

<<$X_{v1}$, $X_{v2}$, $X_{w1}$, and $X_{w2}$>>

In Formula (IB), $X_{v1}$, $X_{v2}$, $X_{w1}$, and $X_{w2}$ each represent v1 consecutive X's, v2 consecutive X's, w1 consecutive X's, and w2 consecutive X's.

In Formula (IB), v1, v2, w1, and w2 each independently represent an integer equal to or greater than 0.

v1 preferably satisfies $0 \leq v1 \leq 20$, more preferably satisfies $0 \leq v1 \leq 10$, even more preferably satisfies $0 \leq v1 \leq 5$, and still more preferably satisfies $0 \leq v1 \leq 2$.

v2 preferably satisfies 0≤v2≤20, more preferably satisfies 0≤v2≤10, even more preferably satisfies 0≤v2≤5, and still more preferably satisfies 0≤v2≤2.

w1 preferably satisfies 0≤w1≤20, more preferably satisfies 0≤w1≤10, even more preferably satisfies 0≤w1≤5, and still more preferably satisfies 0≤w1≤2.

w2 preferably satisfies 0≤w2≤20, more preferably satisfies 0≤w2≤10, even more preferably satisfies 0≤w2≤5, and still more preferably satisfies 0≤w2≤2.

<<Number of Amino Acid Residues in Cyclic Portion>>

In Formula (IB), the number of amino acid residues [(m+n+5) residues] in the cyclic portion $[X^a\text{-}X_m\text{-}X^1\text{-}X^2\text{-}X^3\text{-}X_n\text{-}X^b]$ is 8 to 14, preferably 9 to 13, and more preferably 10 to 12, similarly to Formula (I).

In a case where the number of amino acid residues in the cyclic portion is within the above range, the intramolecular strain of the cyclic peptide does not excessively increase, and the high-order structure such as α-helix is stabilized. Therefore, the antibody binding properties of the cyclic peptide of the present invention become excellent.

<<Number of Repeating Units>>

In a case where k≥2, that is, in a case where the cyclic peptide represented by Formula (IB) includes two or more repeating units $[X_i\text{-}X^a\text{-}X_m\text{-}X^1\text{-}X^2\text{-}X^3\text{-}X_n\text{-}X^b\text{-}X_j]$, $X^1$, $X^2$, $X^3$, $X^a$, $X^b$, $X_m$, $X_n$, $X_i$, and $X_j$ in the repeating unit each may be the same or different between the repeating units.

<<Total Number of Amino Acid Residues in Cyclic Peptide>>

The total number of amino acid residues in the cyclic peptide represented by Formula (IB) is preferably 8 to 50, more preferably 9 to 40, even more preferably 10 to 30, and still more preferably 10 to 20.

That is, in Formula (IB), i, j, m, n, t, u, v1, v2, w1, w2, and k preferably satisfy 8≤(i+j+m+n+5)×k+t+u+v1+v2+w1+w2≤50, more preferably satisfy 9≤(i+j+m+n+5)×k+t+u+v1+v2+w1+w2≤40, even more preferably satisfy 10≤(i+j+m+n+5)×k+t+u+v1+v2+w1+w2≤30, and still more preferably satisfy 10≤(i+j+m+n+5)×k+t+u+v1+v2+w1+w2≤20.

Generally, the larger the number of amino acid residues, the higher the manufacturing cost. Therefore, from the viewpoint of economic efficiency, it is preferable that the total number of amino acid residues is small.

Exception in Third Embodiment

In the third embodiment of the present invention, X in Formula (IB) represents an amino acid residue derived from an amino acid other than L-serine, D-serine, L-homoserine, D-homoserine, L-arginine, and D-arginine, in a case where there is a plurality of X's, the plurality of X's may be the same as or different from each other; and $X^6$ and $X^7$ in Formula (IB) each independently represents "an amino acid residue derived from an amino acid, 'other than L-serine, D-serine, L-homoserine, D-homoserine, L-arginine, and D-arginine', having an immobilizing functional group on a side chain", and in a case where there is a plurality of $X^6$'s and $X^7$'s, the plurality of $X^6$'s or $X^7$'s may be the same as or different from each other. In the third embodiment of the present invention, due to these differences, Formula (IB) is referred to as Formula (I'B) in some cases.

Exception in Fourth Embodiment

In the fourth embodiment of the present invention, X in Formula (IB) represents an amino acid residue derived from an amino acid other than L-serine and D-serine, and in a case where there is a plurality of X's, the plurality of X's may be the same as or different from each other; and $X^6$ and $X^7$ in Formula (IB) each independently represent "an amino acid residue derived from an amino acid, 'other than L-serine and D-serine', having an immobilizing functional group on a side chain, and in a case where there is a plurality of $X^6$'s or $X^7$'s, the plurality of $X^6$'s or $X^7$'s may be the same as or different from each other.

In the fourth embodiment of the present invention, due to these differences, Formula (IB) is referred to as Formula (I'B) in some cases.

<Structure of Cyclic Peptide (IC) of Present Invention>

The cyclic peptide of the present invention is more preferably a cyclic peptide represented by Formula (IC).

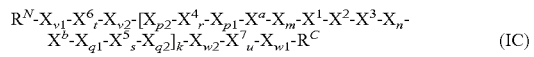

$$R^N\text{-}X_{v1}\text{-}X^6_t\text{-}X_{v2}\text{-}[X_{p2}\text{-}X^4_r\text{-}X_{p1}\text{-}X^a\text{-}X_m\text{-}X^1\text{-}X^2\text{-}X^3\text{-}X_n\text{-}X^b\text{-}X_{q1}\text{-}X^5_s\text{-}X_{q2}]_k\text{-}X_{w2}\text{-}X^7_u\text{-}X_{w1}\text{-}R^C \quad (IC)$$

In Formula (IC), all of $R^N$, $R^C$, $X^1$, $X^2$, $X^3$, $X^a$, $X^b$, $X_m$, $X_n$, X, m, n, and k have the same definitions as those in Formula (I), all of $X^4$, $X^5$, p1, p2, q1, q2, r, and s have the same definitions as those in Formula (IA), and all of $X^6$, $X^7$, t, u, v1, v2, w1, and w2 have the same definitions as those in Formula (IB).

In Formula (IC), similarly to $X_n$ in Formula (I), $X_n$ means that n X's are linked to each other. The same is true for $X_m$, $X_{p1}$, $X_{p2}$, $X_{q1}$, $X_{q2}$, $X_{v1}$, $X_{v2}$, $X_{w1}$, and $X_{w2}$.

In Formula (IC), $X^4_r$, $X^5_s$, $X^6_t$, and $X^7_u$ each mean that r $X^4$'s are linked to each other, s $X^5$'s are linked to each other, t $X^6$'s are linked to each other, and u $X^7$'s are linked to each other.

<<Cyclic Portion, Linear Portion, Cross-Linked Portion, and Antibody Binding Portion>>

In the cyclic peptide represented by Formula (IC), "$X_{v1}\text{-}X^6_t\text{-}X_{v2}$", "$X_{w2}\text{-}X^7_u\text{-}X_{w1}$", "$X_{p2}\text{-}X^4_r\text{-}X_{p1}$", and "$X_{q1}\text{-}X^5_s\text{-}X_{q2}$" are linear portions. The cyclic portion, the cross-linked portion, and the antibody binding portion are the same as those in the cyclic peptide represented by Formula (I).

In Formula (IC), $[X_{p2}\text{-}X^4_r\text{-}X_{p1}\text{-}X^a\text{-}X_m\text{-}X^1\text{-}X^2\text{-}X^3\text{-}X_n\text{-}X^b\text{-}X^5\text{-}X_{q2}]$ is a repeating unit, similarly to Formula (IA).

<<Number of Amino Acid Residues in Cyclic Portion>>

In Formula (IC), the number of amino acid residues [(m+n+5) residues] in the cyclic portion $[X^a\text{-}X_m\text{-}X^1\text{-}X^2\text{-}X^3\text{-}X_n\text{-}X^b]$ is 8 to 14, preferably 9 to 13, and even more preferably 10 to 12, similarly to Formula (I).

In a case where the number of amino acid residues in the cyclic portion is within the above range, the intramolecular strain of the cyclic peptide does not excessively increase, and the high-order structure such as α-helix is stabilized. Therefore, the antibody binding properties of the cyclic peptide of the present invention become excellent.

<<Number of Repeating Units>>

In a case where k≥2, that is, in a case where the cyclic peptide represented by Formula (IC) includes two or more repeating units $[X_{p2}\text{-}X^4_r\text{-}X_{p1}\text{-}X^a\text{-}X_m\text{-}X^1\text{-}X^2\text{-}X^3\text{-}X_n\text{-}X^b\text{-}X_{q1}\text{-}X^5_s\text{-}X_{q2}]$, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in the repeating unit each may be the same or different between the repeating units.

<<Total Number of Amino Acid Residues in Cyclic Peptide>>

The total number of amino acid residues in the cyclic peptide represented by Formula (IC) is preferably 8 to 50, more preferably 9 to 40, even more preferably 10 to 30, and still more preferably 10 to 20.

That is, in Formula (IC), m, n, p1, p2, q1, q2, r, s, t, u, v1, v2, w1, w2, and k preferably satisfy 8≤(m+n+p1+p2+q1+q2+r+s+5)×k+t+u+v1+v2+w1+w2≤50, more preferably satisfy 9≤(m+n+p1+p2+q1+q2+r+s+5)×k+t+u+v1+v2+w1+ w2≤40, even more preferably satisfy 10≤(m+n+p1+p2+q1+q2+r+s+5)×k+t+u+v1+v2+w1+w2≤30, and still more preferably satisfy 10≤(m+n+p1+p2+q1+q2+r+s+5)×k+t+u+v1+v2+w1+w2≤20.

Generally, the larger the number of amino acid residues, the higher the manufacturing cost. Therefore, from the viewpoint of economic efficiency, it is preferable that the total number of amino acid residues is small.

Exception in Third Embodiment

In the third embodiment of the present invention, X in Formula (IC) represents an amino acid residue derived from an amino acid other than L-serine, D-serine, L-homoserine, D-homoserine, L-arginine, and D-arginine, and in a case where there is a plurality of X's, the plurality of X's may be the same as or different from each other; $X^4$ and $X^5$ in Formula (IC) each independently represent "an amino acid residue derived from an amino acid having a carboxy group on a side chain" or "an amino acid residue derived from an amino acid, 'other than L-serine, D-serine, L-homoserine, and D-homoserine', having a hydroxy group on a side chain, and in a case where there is a plurality of $X^4$'s or $X^5$'s, the plurality of $X^4$'s or $X^5$'s may be the same as or different from each other; and $X^6$ and $X^7$ in Formula (IC) each independently represent "an amino acid residue derived from an amino acid, 'other than L-serine, D-serine, L-homoserine, D-homoserine, L-arginine, and D-arginine', having an immobilizing functional group on a side chain", and in a case where there is a plurality of $X^6$'s or $X^7$', the plurality of $X^6$'s or $X^7$'s may be the same as or different from each other.

In the third embodiment of the present invention, due to these differences, Formula (IC) is referred to as Formula (I'C) in some cases.

Exception in Fourth Embodiment

In the fourth embodiment of the present invention, X in Formula (IC) represents an amino acid residue derived from an amino acid other than L-serine and D-serine, and in a case where there is a plurality of X's, the plurality of X's may be the same as or different from each other; $X^4$ and $X^5$ in Formula (IC) each independently represent "an amino acid residue derived from an amino acid having a carboxy group on a side chain" or "an amino acid residue derived from an amino acid, 'other than L-serine and D-serine', having a hydroxy group on a side chain", and in a case where there is a plurality of $X^4$'s or $X^5$'s, the plurality of $X^4$'s or $X^5$'s may be the same as or different from each other; and $X^6$ and $X^7$ in Formula (IC) each independently represent "an amino acid residue derived from an amino acid, 'other than L-serine and D-serine', having an immobilizing functional group on a side chain", and in a case where there is a plurality of $X^6$'s or $X^7$'s, the plurality of $X^6$'s or $X^7$'s may be the same as or different from each other.

In the fourth embodiment of the present invention, due to these differences, Formula (IC) is referred to as Formula (I'C) in some cases.

<Preferred Partial Amino Acid Sequence>

The partial amino acid sequence $X_m$-$X^1$-$X^2$-$X^3$-$X_n$ in Formula (I), (IA), (IB), or (IC) and an amino acid sequence (SEQ ID NO: 1) represented by Formula (1) preferably share sequence homology of equal to or higher than 70%, more preferably share sequence homology of equal to or higher than 75%, even more preferably share sequence homology of equal to or higher than 85%, and still more preferably share sequence homology of equal to or higher than 90%.

$$\text{A-Y-H-L-G-E-L-V-W} \quad (1)$$

In Formula (1), A represents an L-alanine residue; Y represents an L-tyrosine residue; H represents an L-histidine residue; L represents an L-leucine residue; G represents a glycine residue; E represents an L-glutamic acid residue; V represents an L-valine residue; and W represents an L-tryptophan residue.

The partial amino acid sequence $X_m$-$X^1$-$X^2$-$X^3$-$X_n$ in Formula (I), (IA), (IB), or (IC) and an amino acid sequence (SEQ ID NO: 2) represented by Formula (2) preferably share sequence homology of equal to or higher than 70%, more preferably share sequence homology of equal to or higher than 75%, even more preferably share sequence homology of equal to or higher than 85%, and still more preferably share sequence homology of equal to or higher than 90%.

$$\text{A-Y-H-R-G-E-L-V-W} \quad (2)(\text{SEQ ID NO:2})$$

In Formula (2), A represents an L-alanine residue; Y represents an L-tyrosine residue; H represents an L-histidine residue; R represents an L-arginine residue; G represents a glycine residue; E represents an L-glutamic acid residue; L represents an L-leucine residue; V represents an L-valine residue; and W represents an L-tryptophan residue.

The sequence homology between two amino acid sequences is determined as below.

(i) Performing Alignment of Two Amino Acid Sequences

By assigning a score of +1 to matches, a score of −1 to mismatches, and a score of −1 to gaps, alignment is performed such that the alignment score is maximized.

(ii) Calculating Sequence Homology

Based on the obtained alignment, the sequence homology is calculated by the following expression.

Sequence homology [%]=(number of matching positions/total number of positions)×100[%]

The total number of positions is the length of an alignment, and the number of matching positions is the number of positions in which the types of amino acids are matched.

Whether or not the types of amino acid residues are matched is determined according to whether or not the structure of a side chain of an amino acid (amino acid side chain) from which the amino acid residues are derived is the same. The structures of side chains of amino acids having an enantiomeric relationship are not the same as each other.

(iii) Calculation Example of Sequence Homology

For example, suppose that there are amino acid sequences shown below.

Sequence A AYHRGELVW (SEQ ID NO: 2)
Sequence B AWHLGELVW (SEQ ID NO: 94)

In a case where alignment is performed under the conditions described above, the following result is obtained. Herein, the sites where the types of amino acids (residues) are the same between the sequences A (SEQ ID NO: 2) and B (SEQ II) NO: 94) are marked with a homology string "|" such that the sites are easily recognized. Furthermore, "-" is a gap.

```
Sequence A   A Y H R G E L V W
             |   |   | | | | |
Sequence B   A W H L G E L V W
```

The scores of this alignment is that matches (+1)×7+ mismatches (−1)×1+gaps (−1)×1=5.

In this example, the total number of positions is 9, the number of matching positions is 7. Therefore, the sequence homology calculated according to the above expression is 7/9×100=77.8%.

<Preferred Number of Repeating Units>

In the present invention, k in Formulae (I) to (IC) is preferably 1.

In a case where the cyclic peptide has one cyclic portion-including portion, the total length of the cyclic peptide can be shortened, and hence the cyclic peptide is easily synthesized. Furthermore, by the Huisgen reaction at the time of cyclization, it is possible to avoid the formation of a cross-link at an unintended site.

<Structure of Cyclic Peptide (II) of Present Invention>

The cyclic peptide of the present invention is particularly preferably a cyclic peptide represented by Formula (II).

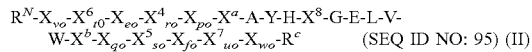

$R^N$-$X_{vo}$-$X^6_{t0}$-$X_{eo}$-$X^4_{ro}$-$X_{po}$-$X^a$-A-Y-H-$X^8$-G-E-L-V-W-$X^b$-$X_{qo}$-$X^5_{so}$-$X_{fo}$-$X^7_{uo}$-$X_{wo}$-$R^c$      (SEQ ID NO: 95) (II)

In Formula (II), xa, xb, RN, and RC have the same definitions as those in Formula (I).

<<Cyclic Portion, Linear Portion, Cross-Linked Portion, and Antibody Binding Portion>>

In the cyclic peptide represented by Formula (II), "$X^a$-A-Y-H-$X_8$-G-E-L-V-W-$X^b$" (SEQ ID NO: 96) is a cyclic portion, "$X_{vo}$-$X^6_{t0}$-$X_{eo}$-$X4_{ro}$-$X_{po}$-" and "$X_{qo}$-$X^5_{so}$-$X_{fo}$-$X^7_{uo}$-$X_{wo}$" are linear portions, "$X^a$" and "$X^b$" are cross-linked portions, and "L-V-W" is an antibody binding portion.

<<$X^4_{r0}$ and $X^5_{s0}$>>

In Formula (II), $X^4_{r0}$ and $X^5_{s0}$ each represent r0 consecutive $X^4$'s and s0 consecutive $X^5$'s.

In Formula (II), $X^4$ and $X^5$ have the same definitions as those in Formula (IA).

In Formula (II), r0 and s0 each represent an integer satisfying 0≤r0≤5 and 0≤s0≤5.

r0 preferably satisfies 0≤r0≤3, and more preferably satisfies 0≤r0≤2.

s0 preferably satisfies 0≤s0≤3, and more preferably satisfies 0≤s0≤2.

<<$X^6_{t0}$ and $X^7_{u0}$>>

In Formula (II), $X^6_{r0}$ and $X^7_{t0}$ each represent t0 consecutive $X^6$'s and u0 consecutive $X^7$'s.

In Formula (II), $X^6$ and $X^7$ have the same definitions as those in Formula (IB).

In Formula (II), t0 and u0 each represent an integer satisfying 0≤t0≤5 and 0≤u0≤5.

t0 preferably satisfies 0≤t0≤3, and more preferably satisfies 0≤t0≤2.

u0 preferably satisfies 0≤u0≤3, and more preferably satisfies 0≤u0≤2.

<<$X_{e0}$, $X_{f0}$, $X_{p0}$, $X_{q0}$, $X_{v0}$, and $X_{w0}$>>

$X_{e0}$, $X_{f0}$, $X_{p0}$, $X_{q0}$, $X_{v0}$, and $X_{w0}$ each represent e0 consecutive X's, f0 consecutive X's, p0 consecutive X's, q0 consecutive X's, v0 consecutive X's, and w0 consecutive X's.

X has the same definition as that in Formula (I).

e0 and f0 each represent an integer satisfying 0≤e0≤10 and 0≤f0≤10.

e0 preferably satisfies 0≤e0≤5, more preferably satisfies 0≤e0≤3, and even more preferably satisfies 0≤e0≤2.

f0 preferably satisfies 0≤f0≤5, more preferably satisfies 0≤f0≤3, and even more preferably satisfies 0≤f0≤2.

p0 and q0 each represent an integer satisfying 0≤p0≤5 and 0≤q0≤5.

p0 preferably satisfies 0≤p0≤3, and more preferably satisfies 0≤p0≤2.

q0 preferably satisfies 0≤q0≤3, and more preferably satisfies 0≤q0≤2.

v0 and w0 each represent an integer satisfying 0≤v0≤5 and 3≤w0≤5.

v0 preferably satisfies 0≤v0≤3, and more preferably satisfies 0≤v0≤2.

w0 preferably satisfies 0≤w0≤3, and more preferably satisfies 0≤w0≤2.

$X^8$ represents an L-leucine residue, a D-leucine residue, an L-arginine residue, or a D-arginine residue.

In Formula (II), A represents an L-alanine residue or a D-alanine residue; Y represents an L-tyrosine residue or a D-tyrosine residue; H represents an L-histidine residue or a D-histidine residue; G represents a glycine residue; E represents an L-glutamic acid residue or a D-glutamic acid residue; L represents an L-leucine residue; V represents an L-valine residue; and W represents an L-tryptophan residue.

<<Total Number of Amino Acid Residues in Cyclic Peptide>>

In Formula (II), the total number of amino acid residues in the cyclic peptide is 11 to 50, preferably 11 to 40, more preferably 11 to 30, and even more preferably 11 to 20.

That is, in Formula (II), e0, f0, p0, q0, r0, s0, t0, u0, v0, and w0 satisfy 0≤e0+f0+p0+q0+r0+s0+t0+u0+v0+w0≤39, preferably satisfy 0≤e0+f0+p0+q0+r0+s0+t0+u0+v0+w0≤29, more preferably satisfy 0≤e0+f0+p0+q0+r0+s0+t0+u0+v0+w0≤19, and even more preferably satisfy 0≤e0+f0+p0+q0+r0+s0+t0+u0+v0+w0≤9.

<Antibody Binding Properties>

The cyclic peptide of the present invention has excellent antibody binding properties. The antibody binding properties refer to binding activity with respect to antibodies and/or antibody derivatives. The higher the binding activity is, the more the antibodies are adsorbed onto the cyclic peptide in a case where the cyclic peptide is used as an affinity ligand for affinity chromatography for antibody purification, and hence a large amount of antibodies can be purified at a time. An antibody refers to immunoglobulin or an analogue, a fragment, or a conjugate of the antibody. The analogue refers to a natural protein or protein conjugate or to an artificially prepared protein or protein conjugate which keeps the structure or function of immunoglobulin in at least a portion thereof. The fragment refers to a protein which is prepared by an enzymatic treatment or designed by genetic engineering and has a partial structure of immunoglobulin. The conjugate refers to a protein prepared by fusing a functional portion of proteins having a biological activity such as various cytokines or cytokine receptors with the entirety or a portion of immunoglobulin through genetic engineering. The antibody is preferably a monoclonal antibody or a conjugate having an Fc region of immunoglobulin, and more preferably a monoclonal antibody. In the present invention, the immunoglobulin may be of any of five classes (isotypes) including immunoglobulin G (IgG), immunoglobulin M (IgM), immunoglobulin A (IgA), immunoglobulin D (IgD), and immunoglobulin E (IgE). Among these, IgG or IgM is preferable, and IgG is more preferable.

<Alkali Resistance>

The cyclic peptide of the present invention has excellent temporal stability or chemical resistance. Particularly, the cyclic peptide of the present invention has excellent alkali resistance. Because the cyclic peptide has excellent chemical resistance, for example, in a case where a support for affinity chromatography, in which the cyclic peptide of the present invention is used as an affinity ligand, is used for antibody purification, even if the support is repeatedly washed with a chemical, particularly, an alkali, the antibody binding properties are maintained. Therefore, the antibody purification cost can be further reduced.

Exception in Third Embodiment

In the third embodiment of the present invention, X in Formula (II) represents an amino acid residue derived from an amino acid other than L-serine, D-serine, L-homoserine, D-homoserine, L-arginine, and D-arginine, and in a case where there is a plurality of X's, the plurality of X's may be the same as or different from each other; $X^4$ and $X^5$ in Formula (II) each independently represent "an amino acid residue derived from an amino acid having a carboxy group on a side chain" or "an amino acid residue derived from an amino acid, 'other than L-serine, D-serine, L-homoserine, and D-homoserine', having a hydroxy group on a side chain", and in a case where there is a plurality of $X^4$'s or $X^5$'s, the plurality of $X^4$'s or $X^5$'s may be the same as or different from each other; $X^6$ and $X^7$ in Formula (II) each independently represent "an amino acid residue derived from an amino acid, 'other than L-serine, D-serine, L-homoserine, D-homoserine, L-arginine, and D-arginine', having an immobilizing functional group on a side chain, and in a case where there is a plurality of $X^6$'s or $X^7$'s, the plurality of $X^6$'s or $X^7$'s may be the same as or different from each other; and $X^8$ in Formula (II) represents an L-leucine residue or a D-leucine residue.

In the third embodiment of the present invention, due to these differences, Formula (II) is referred to as Formula (II') in some cases.

Exception in Fourth Embodiment

In the fourth embodiment of the present invention, X in Formula (II) represents an amino acid residue derived from an amino acid other than L-serine and D-serine, in a case where there is a plurality of X's, the plurality of X's may be the same as or different from each other; $X^4$ and $X^5$ in Formula (II) each independently represent "an amino acid residue derived from an amino acid having a carboxy group on a side chain" or "an amino acid residue derived from an amino acid, 'other than L-serine and D-serine', having a hydroxy group on a side chain", and in a case where there is a plurality of $X^4$'s or $X^5$'s, the plurality of $X^4$'s or $X^5$'s may be the same as or different from each other; and $X^6$ and $X^7$ in Formula (II) each independently represent "an amino acid residue derived from an amino acid, 'other than L-serine and D-serine', having an immobilizing functional group on a side chain", and in a case where there is a plurality of $X^6$'s or $X^7$'s, the plurality of $X^6$'s or $X^7$'s may be the same as or different from each other.

In the fourth embodiment of the present invention, due to these differences, Formula (II) is referred to as Formula (II') in some cases.

[Method for Synthesizing Cyclic Peptide]

The method for synthesizing the cyclic peptide of the present invention is not particularly limited. For example, the cyclic peptide can be synthesized by a peptide synthesis method based on synthetic organic chemistry or by a peptide synthesis method based on genetic engineering.

As the peptide synthesis method based on synthetic organic chemistry, any of a liquid-phase synthesis method and a solid-phase synthesis method can be used. As the method for synthesizing the polypeptide of the present invention, a solid-phase synthesis method in which an automatic peptide synthesis device is used is preferable because this method is convenient.

The peptide synthesis method based on genetic engineering is a method of synthesizing a peptide by introducing a gene into a cell. As the cell, bacteria, eelworm cells, insect cells, mammal cells, animal cells, and the like are used.

For example, by introducing a non-natural amino acid into a cell by using a four-base codon method, the cyclic peptide can be synthesized. Furthermore, by synthesizing a linear peptide and causing cyclization by reacting a cross-linking functional group on a side chain of an amino acid residue introduced into a cyclic portion, the cyclic peptide can be synthesized.

In a case where a disulfide bond needs to be formed, for example, by reacting side-chain thiol groups of two amino acid residues, which are derived from an amino acid having a thiol group on a side chain, under oxidizing conditions, a disulfide bond can be formed. Specifically, for example, by forming a disulfide bond between side-chain thiol groups of two L-homocysteine residues, a linear polypeptide can be cyclized.

In a case where a thioether bond needs to be formed, for example, by reacting a side-chain thiol group of an amino acid residue derived from an amino acid having a thiol group on a side chain with a side-chain chloroacetyl group of an amino acid residue derived from an amino acid having a chloroacetyl group on a side chain, a thioether bond can be formed. Specifically, for example, by forming a thioether bond between a side-chain thiol group of an L-homocysteine residue and a side-chain chloroacetyl group of an N-ε-chloroacetyl-L-lysine residue, a linear polypeptide can be cyclized.

Instead of an amino acid having a haloacetyl group such as a chloroacetyl group on a side chain, it is possible to use an amino acid having a haloalkanoyl group such as a chloropropionyl group, which has more methylene units compared to a haloacetyl group, on a side chain. However, it is preferable to use the amino acid having a haloacetyl group on a side chain, because the smaller the number of methylene units, the higher the cyclization efficiency. For example, between a halopropionyl group (—C(=O)—$(CH_2)_2$—X; X represents a halogen atom, having two methylene units) and an acetyl group (—C(=O)—$CH_2$—X; X represents a halogen atom, having one methylene unit), the acetyl group is preferable because it has a higher cyclization efficiency.

[Use of Cyclic Peptide of Present Invention]

The cyclic peptide of the present invention can be used as an antibody binding ligand, a linker for labeling antibodies, a linker for an antibody drug conjugate, a drug carrier (linker for pharmaceutical products), and the like, but the use of the cyclic peptide of the present invention is not limited to these.

<Antibody Binding Ligand and Affinity Chromatography Support>

The cyclic peptide of the present invention can be used as an antibody binding ligand in the technical field of affinity chromatography.

Examples of applications of the cyclic peptide of the present invention used as an antibody binding ligand include an antibody or antibody derivative adsorbing material in which the cyclic peptide of the present invention is immobilized on a water-insoluble support and an affinity chromatography support.

"Water-insoluble support" refers to a support which is substantially insoluble in water. Examples of such a support include polysaccharides such as crystalline cellulose, cross-linked cellulose, cross-linked agarose, cross-linked dextran, and cross-linked pullulan, organic supports such as an acrylate-based polymer and a styrene-based polymer, inorganic supports such as glass beads and silica gel, composite supports such as an organic-organic composite support and an organic-inorganic composite support obtained by combining the above supports, and the like. From the viewpoint of alkali resistance, as the water-insoluble support, polysaccharides or an acrylate-based polymer is more preferable, and polysaccharides such as agarose or cellulose are more preferable. Examples of commercial products that can be used as the water-insoluble support include porous cellulose gel such as Cellufine GCL2000 (manufactured by JNC Corporation) (CELLUFINE is a registered trademark) and Cellfine MAX (manufactured by JNC Corporation), Sephacryl S-1000 SF (manufactured by GE Healthcare) obtained by cross-linking allyl dextran to methylenebisacrylamide through a covalent bond (SEPHACRYL is a registered trademark), acrylate-based supports such as TOYOPEARL (manufactured by Tosoh Corporation) (TOYOPEARL is a registered trademark), TOYOPEARL AF-Carboxy-650 (manufactured by Tosoh Corporation), and TOYOPEARL GigaCap CM-650 (manufactured by Tosoh Corporation), an agarose-based cross-linked support such as Sepharose CL4B (manufactured by GE Healthcare) (SEPHAROSE is a registered trademark), polymethcrylamide activated by an epoxy group such as Eupergit C250L (manufactured by Sigma-Aldrich Co., LLC.) (EUPERGIT is a registered trademark), and the like. Here, the water-insoluble support in the present invention is not limited to the supports or the activated supports described above. Considering the purpose of use of the original adsorbing material and how to use the original absorbing material, it is preferable that the water-insoluble support used in the present invention has a large surface area and is porous support having a number of pores with an appropriate size. The shape of the support is not particularly limited. The support can be any of a bead-like support, a fibrous support, a film-like support, and hollow fibrous support, and it is possible to select any shape.

The method for immobilizing the cyclic peptide of the present invention on the water-insoluble support is not particularly limited. For example, generally, it is possible to adopt a method that is adopted in a case where a protein or a polypeptide is immobilized on a support.

For example, the cyclic peptide can be immobilized by a method of activating a support by reacting the support with cyanogen bromide, epichlorohydrin, diglycidyl ether, tosyl chloride, tresyl chloride, hydrazine, and the like or introducing a reactive functional group into the surface of the support and immobilizing the support by reacting the support with a compound immobilized as a ligand, or a method of causing condensation by adding a condensation reagent such as carbodiimide or a reagent having a plurality of functional groups in a molecule such as glyceraldehyde to a system including a support and a compound immobilized as a ligand and cross-linking the condensate.

In the present invention, "ligand" refers to a molecule which has a certain degree of affinity with a specific substance and binds to the substance. The specific substance is not particularly limited, and is preferably an antibody or an antibody derivative. The binding site at which the ligand binds to an antibody or an antibody derivative is not particularly limited. From the viewpoint of versatility, the binding site is preferably a constant region of an antibody or an antibody derivative. The constant region is not particularly limited, and is preferably fragment crystallizable (Fc) regions, constant regions of a light chain (CL regions), or constant regions of a heavy chain (CH regions). In the present invention, the ligand which can bind to an antibody or an antibody derivative is referred to as "antibody binding ligand" in some cases.

At the time of immobilizing a ligand on a support, it is preferable to dissolve (disperse) the ligand in an aqueous solvent (aqueous dispersion medium) or an organic solvent (organic dispersion medium). The aqueous solvent (aqueous dispersion medium) is not particularly limited, and examples thereof include a 4-(2-hydroxyethyl)-1-piperazineethanesulfonic acid (HEPES) buffer solution, an acetic acid buffer solution, a phosphoric acid buffer solution, a citric acid buffer solution, a tris-hydrochloric acid buffer solution, and the like. The organic solvent (organic dispersion medium) is not particularly limited. The organic solvent is particularly preferably an organic polar solvent such as dimethyl sulfoxide (DMSO), N,N-dimethylformamide (DMF), or alcohol, and examples thereof include methanol, ethanol, isopropyl alcohol (IPA), 2,2,2-trifluoroethanol (TFE), 1,1,1,3,3,3-hexafluoro-2-propanol (HFIP), and the like.

The pH condition at the time of immobilizing the ligand is not particularly limited, and any of acidic, neutral, and alkaline conditions can be adopted. For example, the pH condition can be appropriately set according to the solvent (dispersion medium) to be used.

For example, in a case where the pH condition needs to be made alkaline, a base such as diazabicycloundecene (DBU) may be added to dimethyl sulfoxide (DMSO) or an alcohol.

In a case where the aforementioned adsorbing material is used as a filler for affinity chromatography, the density of antibody binding ligands is not particularly limited. However, the density is preferably 0.1 to 1,000 mmol/1 L of filler, more preferably 0.1 to 100 mmol/1 L of filler, and even more preferably 0.5 to 20 mmol/1 L of filler. In a case where the density is within the above range, the amount of the antibody binding ligand used and the antibody purification performance are balanced well, and it is possible to efficiently purify antibodies at lower costs.

<Linker for Labeling Antibodies and Labeled Antibody>

In the technical field of immunoassay, the cyclic peptide of the present invention can be used as a linker for labeling antibodies.

Examples of applications of the cyclic peptide of the present invention used as the linker for labeling antibodies include a labeled antibody which includes an antibody, a labeling compound, and the cyclic peptide of the present invention and in which the antibody and the labeling compound are bonded to each other through the cyclic peptide of the present invention.

Immunoassay is an analysis method for detecting or quantifying a trace substance by using an immune reaction (antigen-antibody reaction), and features high specificity and high sensitivity.

In the immunoassay, in order to detect an antibody (primary antibody) having bonded to a trace substance (antigen), a method of directly labeling the primary antibody, a method of labeling an antibody (secondary antibody) binding to the primary antibody, and the like are used. The cyclic peptide of the present invention can be used as a linker for causing a labeling substance to bind to a primary antibody or as a linker for causing a labeling substance to bind to a secondary antibody. The cyclic peptide of the present invention has antibody binding properties (immunoglobulin G (IgG) binding properties). Therefore, the labeled cyclic peptide of the present invention can also be used instead of a labeled secondary antibody.

There are various labels. A system in which a radioisotope is used as a label is called radioimmunoassay (RIA), a system in which an enzyme such as peroxidase is used as a label is called enzyme immunoassay (EIA), a system in which a chemiluminescent substance such as luminol is used as a label is called chemiluminescent immunoassay (CLIA), and a system in which a fluorescent substance (fluorescent dye) such as fluorescein isothiocyanate (FITC) is used as a labeling substance is called fluorescent immunoassay (FIA). The cyclic peptide of the present invention can be used as a linker for labeling antibodies in any of the systems.

In order to improve the detection sensitivity of immunoassay, a number of labels need to be attached to one antibody molecule. With the linker for labeling antibodies of the related art, in a case where a number of the linkers bind to an antibody, the antibody binding activity deteriorate. Accordingly, the specificity and the sensitivity which are advantages of immunoassay are likely to be impaired. In contrast, according to the cyclic peptide of the present invention, even in a case where a number of the cyclic peptides bind to an antibody, the structural integrity of the antibody can be maintained, and the antibody binding activity is not reduced. Therefore, even in a case where a number of the cyclic peptides bind to an antibody, the detection sensitivity could be improved without impairing the specificity and the sensitivity which are advantages of immunoassay. In addition, because the cyclic peptide binds to an antibody through an antigen-antibody reaction, the separation of the cyclic peptide after labeling that was difficult to perform in the related art can be conducted, and hence reversible labeling can be realized.

<Linker for Antibody Drug Conjugates and Antibody Drug Conjugate>

In the technical field of antibody drug conjugates, the cyclic peptide of the present invention can be used as a linker for antibody drug conjugates.

Examples of applications of the cyclic peptide of the present invention used as a linker for antibody drug conjugates include an antibody drug conjugate which includes an antibody, a drug, and the cyclic peptide of the present invention and in which the antibody binds to the drug through the cyclic peptide of the present invention.

The antibody drug conjugate (ADC) is also called by another name "armed antibody". ADC is a drug obtained by binding an antibody recognizing a cell to a drug (low-molecular weight drug) which is a main active component by using an appropriate linker. The mechanism of action of the antibody drug conjugate is roughly as below.

(1) The antibody portion of an antibody drug conjugate binds to a target molecule on the surface of a target cell.

(2) The antibody drug conjugate infiltrates into the cell.

(3) The linker of the antibody drug conjugate is cleaved in the cell.

(4) The drug (low-molecular weight drug) exerts its efficacy in the cell.

With the antibody drug conjugate, because the efficacy is exerted only in the cell expressing a molecule that the antibody targets, it is possible to inhibit the systemic side effects and to cause the efficacy to be exerted mainly in a target cell. Therefore, the antibody drug conjugate is more efficacious and causes less side effects compared to simple drugs. For example, the anticancer agent developed for attacking cancer cells in which cell division vigorously occurs also attacks the cells, in which cell division vigorously occurs as in the cancer cells but the function thereof is maintained, specifically, the cells responsible for immunity, the cells of the gastrointestinal tract, the hair follicle cells, and the like. Consequently, as side effects, the symptoms such as vulnerability to infectious diseases, diarrhea, and hair loss occur in some cases. However, with the antibody drug conjugate, the anticancer agent can be selectively carried to target cancer cells, and accordingly, it is possible to inhibit the side effects caused in a case where the anticancer agent attacks cells other than the target cells.

A linker for antibody drug conjugates is required to link the antibody portion of the antibody drug conjugates to the drug portion, be stable in the blood, and cut off the drug from the antibody in a cell such that the drug is released. Furthermore, the linker for antibody drug conjugates is also required not to impair the binding activity of the antibody. In order to improve the drug carrying efficiency, a number of drugs need to be attached to one antibody molecule. However, with the linker for antibody drug conjugates of the related art, in a case where a number of the linkers bind to an antibody, the antibody binding activity deteriorates. As a result, the selectivity which is the advantage of an antibody drug conjugate is impaired, and the drug is likely to be carried to target cells with low efficiency. However, with the cyclic peptide of the present invention, even in a case where a number of the cyclic peptides bind to an antibody, the structural integrity of the antibody can be maintained, and the antibody binding activity is not reduced. Accordingly, even in a case where a number of the cyclic peptides bind to an antibody, the selectivity which is the advantage of an antibody drug conjugate is not impaired, and the drug could be carried to target cells with improved efficiency. Furthermore, because the temporal stability of the cyclic peptide of the present invention is higher than that of the cyclic peptide of the related art, the stability of the cyclic peptide in the blood could be improved. In addition, by modifying the side-chain portion of a disulfide bond which is a cyclic portion, the drug releasing properties in a cell could be controlled.

The drug may be a liposomized drug, a polymerically micellized drug, or a polyethylene glycolated (PEGylated) drug.

By liposomizing, polymerically micellizing, or PEGylating the drug, in many cases, it is possible to improve the in vivo stability of active components, the pharmacokinetics including a tissue migration profile, the intracellular pharmacokinetics, and the like.

<Drug Carrier and Pharmaceutical Preparation>

The cyclic peptide of the present invention can be used as a drug carrier in a drug delivery system.

Examples of applications of the cyclic peptide of the present invention used as a drug carrier include a pharmaceutical preparation which includes a drug and the cyclic peptide of the present invention and in which the drug and the cyclic peptide of the present invention are directly or indirectly bonded to each other.

In a case where the cyclic peptide of the present invention binds to IgG present in a biological body, the same effects as those brought about by the aforementioned antibody drug conjugate could be obtained. The drug may bind to the cyclic peptide as it is or bind to the cyclic peptide as a drug having undergone liposomization, polymer micellization, or polyethylene glycolation (PEGylation). Furthermore, the drug may bind to the cyclic peptide through polysaccharides such as dextran or a hydrophilic polymer.

As the method for binding a drug to the cyclic peptide of the present invention, the use of a disulfide bond between amino acid residues in the cross-linked portion can be considered.

Specifically, this is a method of reducing a disulfide bond (—S—S—) such that it is cleaved (—S⁻S⁻—) and adding the two ions to a compound in a manner of cross-linking. As this method, for example, ThioBridge (trademark) is known.

EXAMPLES

Hereinafter, the present invention will be more specifically described based on examples, but the present invention is not limited to the examples.

Example 1

(1) Synthesis of Cyclic Peptide

A cyclic peptide (SEQ ID NO: 3; hereinafter, this cyclic peptide will be referred to as "cyclic peptide 1" in some cases) represented by Formula (3) was synthesized using a full automatic peptide synthesis device (PSSM-8, manufactured by Shimadzu Corporation).

$DX^aAYHRGELVWX^bTKK$ (3)

$X^a$ represents an amino acid residue derived from N-ε-chloroacetyl-L-lysine, and $X^b$ represents an amino acid residue derived from L-homocysteine. Between $X^a$ and $X^b$, a thioether bond is formed by a reaction between a side-chain chloroacetyl group of N-ε-chloroacetyl-L-lysine and a side-chain thiol group of L-homocysteine.

(2) Ligand Immobilization

A commercially available CM5 (carboxymethyl dextran introduction-type, manufactured by GE Healthcare) sensor chip was set in Biacore 3000 (Biacore is a registered trademark) as a surface plasmon resonance device manufactured by GE Healthcare, a 4-(2-hydroxyethyl)-1-piperazineethanesulfonic acid (HEPES) buffer solution (20 mM HEPES-HCl, 150 mM NaCl, pH 7.4) for surface plasmon resonance (SPR) was stabilized at a flow rate of 10 μL/min, and 70 μL of an aqueous mixed solution of 0.2 M 1-(3-Dimethylaminopropyl)-3-ethylcarbodiimide (EDC) and 0.04 M of N-Hydroxysuccinimide (NHS) was added thereto. Thereafter, 100 μL of a sample solution of the cyclic peptide 1, which was diluted with a HEPES buffer solution at 0.2 g/L and treated with a polytetrafluoroethylene (PTFE) filter (manufactured by Advantec MFS, Inc.) having a diameter of 0.20 μm, was supplied to the sensor chip, a blocking treatment was then performed using an ethanolamine solution, and the sensor chip was washed with an aqueous sodium hydroxide solution, thereby performing immobilization. Likewise, 70 μL of an aqueous mixed solution of 0.2 M EDC and 0.04 M NHS was added to the same sensor chip without immobilizing the sample in another flow channel, and then the blocking treatment and the washing treatment were performed. Hereinafter, the obtained immobilized sensor chip will be referred to as "immobilized sensor chip A".

(3) Evaluation of Binding Activity

At 25° C., 3,000 nM of human immunoglobulin G (IgG) antibodies were added for 10 minutes to the immobilized sensor chip A prepared in (1) described above. Immediately after the addition, the antibody binding amount was measured, and from the difference in the antibody binding amount between the flow channel in which the cyclic peptide was immobilized and the flow channel in which the cyclic peptide was not immobilized and the amount of the immobilized cyclic peptide, the activity of the cyclic peptide was calculated. Furthermore, by regarding the activity of a cyclic peptide 91 in Comparative Example 1 as 1, the relative binding activity with respect to the human IgG antibodies was calculated.

(Evaluation Standards for Relative Binding Activity)

| | |
|---|---|
| The relative binding activity was higher than 2,000% of the binding activity of the cyclic peptide 5. | S |
| The relative binding activity was higher than 800% of the binding activity of the cyclic peptide 5. | A |
| The relative binding activity was higher than 400% and equal to or lower than 800% of the binding activity of the cyclic peptide 5. | B |
| The relative binding activity was higher than 200% and equal to or lower than 400% of the binding activity of the cyclic peptide 5. | C |
| The relative binding activity was higher than 100% and equal to or lower than 200% of the binding activity of the cyclic peptide 5. | D |
| The relative binding activity was equal to or lower than 100% of the binding activity of the cyclic peptide 5. | E |

The grades A, B, and C show that the immobilization brings about a sufficient improving effect, and the grades D and E show that sufficient binding activity is not exhibited. The grade S shows that the cyclic peptide brings about a particularly excellent improving effect among the cyclic peptides graded A, and such a cyclic peptide is described as "A (S)".

In a case where a cyclic peptide exhibiting sufficient binding activity is used, the cyclic peptide can specifically bind to antibodies, antibodies are more efficiently purified, and the antibody purification cost can be reduced.

(4) Ligand Immobilization 1 mL of HiTrap NHS-activated HP Columns (coupling columns for ligand immobilization, manufactured by GE Healthcare) (HITRAP is a registered trademark) was reacted with 1 mL of 10 mg/mL cyclic peptide solution, which was prepared by dissolving the cyclic peptide 1 in an immobilization buffer (200 mM NaHCO₃, 500 mM NaCl, pH 8.3), for 1 hour at 25° C. The reaction product was blocked by an aqueous ethanolamine solution and washed, thereby obtaining a cyclic peptide 1-immobilized support. Hereinafter, the obtained immobilized support will be referred to as "immobilized support A".

(5) Evaluation of Chemical Resistance

The immobilized support A prepared in (4) described above was connected to a chromatography system AKTA avant 25 (manufactured by GE Healthcare) (AKTAAVANT is a registered trademark), and the antibody binding capacity was measured. The columns were equilibrated using an equilibration solution (20 mM phosphoric acid buffer, 150 mM NaCl, pH 7.4), and then 15 mL of a human IgG antibody solution, of which the concentration was adjusted to be 5 mg/mL by using a standard buffer (20 mM phosphoric acid buffer, 150 mM NaCl, pH 7.4), was added thereto at a flow rate of 0.21 mL/min. Thereafter, the columns were washed with 5 mL of a postloading wash solution (20 mM phosphoric acid buffer, 150 mM NaCl, pH 7.4) caused to flow at the same flow rate and then washed with 5 mL of a pre-elution wash solution (20 mM phosphoric acid buffer, 1 M NaCl, pH 7.4) at the same flow rate. Then, 5 mL of an elution solution (100 mM citric acid buffer, pH 3.2) was caused to flow at the same flow rate. Subsequently, 5 mL of a cleaning in place (CIP) solution (0.1 M sodium hydroxide) was caused to flow at the same flow rate, and then 5 mL of a reequilibration solution (20 mM phosphoric acid buffer, 150 mM NaCl, pH 7.4) was caused to flow at the same flow rate. At this time, by using an immunoglobulin G (IgG) elution peak obtained by monitoring absorbance at 280 nm, the amount of antibodies binding to the support until 10% of the antibody stock solution leaked out of the support was measured as the antibody binding capacity. Then, the immobilized support A was filled with a 0.2 M aqueous NaOH solution for 6 hours at 25° C. and left to stand, the antibody binding capacity of the support was measured in the same manner, and a rate of change in the binding amount was calculated from the antibody binding amount before and after the alkali treatment.

(Evaluation Standards of Rate of Change in Binding Amount)

| | |
|---|---|
| The rate of change in the binding amount was higher than 90% | A |
| The rate of change in the binding amount was higher than 80% and equal to or lower than 90% | B |
| The rate of change in the binding amount was higher than 70% and equal to or lower than 80% | C |
| The rate of change in the binding amount was higher than 50% and equal to or lower than 70% | D |
| The rate of change in the binding amount was equal to or lower than 50% | E |

The grades A, B, and C show that the chemical resistance is sufficient, and the grades D and E show that sufficient chemical resistance is not exhibited. In a case where a cyclic peptide exhibiting sufficient chemical resistance is used, the cyclic peptide can repeatedly specifically bind to antibodies even after washing, antibodies can be purified for a long period of time, and the antibody purification costs can be reduced.

Table 3 shows the structures of the cyclic peptides of Example 1 and the evaluation results of the relative binding activity and the chemical resistance.

Examples 2 and 6

Based on Example 1, a cyclic peptide 2 and a cyclic peptide 6 were synthesized, and the relative binding activity and the chemical resistance were evaluated.

The following code in Table 3 means the following substance.

Hcy: amino acid residue derived from L-homocysteine

Due to the reaction between side-chain thiol groups, a disulfide bond is formed between the amino acid residues in the cross-linked portion, and hence the amino acid residues are cross-linked.

Table 3 shows the structures of the cyclic peptides of Example 2 and Example 6 and the evaluation results of the relative binding activity and the chemical resistance.

Examples 3 to 5

Based on Example 1, cyclic peptides 3 to 5 were synthesized, and the relative binding activity and the chemical resistance were evaluated.

The following codes in Table 3 mean the following substances.

Hcy: amino acid residue derived from L-homocysteine

Orn (acetyl): amino acid residue derived from N-δ-chloroacetyl-L-ornithine

Lys (acetyl): amino acid residue derived from N-ε-chloroacetyl-L-lysine

Due to the reaction between a chloroacetyl group and a thiol group, a thioether bond is formed between the amino acid residues in the cross-linked portion, and hence the amino acid residues are cross-linked.

Table 3 shows the structures of the cyclic peptides of Examples 3 to 5 and the evaluation results of the relative binding activity and the chemical resistance.

Examples 7 to 12

Based on Example 1, cyclic peptides 7 to 12 were synthesized, and the relative binding activity and the chemical resistance were evaluated.

The following codes in Table 3 mean the following substances.

Dap (acetyl): amino acid residue derived from $N^3$-haloacetyl-L-2,3-diaminopropanoic acid[(2S)-2-amino-3-[(2-haloacetyl)amino]propanoic acid]

Dab (acetyl): amino acid residue derived from $N^4$-haloacetyl-L-2,4-diaminobutanoic acid[(2S)-2-amino-4-[(2-haloacetyl)amino]butanoic acid]

Orn (acetyl): amino acid residue derived from N-δ-chloroacetyl-L-ornithine

Lys (acetyl): amino acid residue derived from N-ε-chloroacetyl-L-lysine

Hcy: amino acid residue derived from L-homocysteine

Due to the reaction between a chloroacetyl group and a thiol group, a thioether bond is formed between the amino acid residues in the cross-linked portion, and hence the amino acid residues are cross-linked.

Table 3 shows the structures of the cyclic peptides of Examples 7 to 12 and the evaluation results of the relative binding activity and the chemical resistance.

TABLE 3

| | | Cyclic peptide | | | | | Performance evaluation | | |
|---|---|---|---|---|---|---|---|---|---|
| | Iden- | Amino acid | Amino acid residue in cross-linked portion | | Special amino acid residue | Cross-linked structure | Relative binding activity | Chemical resistance | SEQ ID NO: |
| | tification name | sequence (N terminal → C terminal) | $X^a$ | $X^b$ | $X^α$ | | | | |
| Example 1 | Cyclic peptide 1 | DX$^a$AYHRGELVWX$^b$TKK | Lys (acetyl) | Hcy | — | Thioether bond | A | A | 3 |
| 2 | Cyclic peptide 2 | DX$^a$AYHRGELVWX$^b$TKK | Hcy | Hcy | — | Disulfide bond | A | B | 4 |

TABLE 3-continued

| Iden-tifi-cation name | Cyclic peptide | | | | | Performance evaluation | | SEQ ID NO: |
|---|---|---|---|---|---|---|---|---|
| | Amino acid sequence (N terminal → C terminal) | Amino acid residue in cross-linked portion | | Special amino acid residue $X^\alpha$ | Cross-linked structure | Relative binding activity | Chemical resis-tance | |
| | | $X^a$ | $X^b$ | | | | | |
| 3 Cyclic peptide 3 | DX$^a$AYHRGELVWX$^b$TKK | Hcy | Orn (ace-tyl) | — | Thioether bond | A | A | 5 |
| 4 Cyclic peptide 4 | KKDX$^a$AYHRGELVWX$^b$T | Lys (ace-tyl) | Hcy | — | Thioether bond | A | A | 6 |
| 5 Cyclic peptide 5 | DX$^a$AYHLGELVWX$^b$TKK | Lys (ace-tyl) | Hcy | — | Thioether bond | A | A | 7 |
| 6 Cyclic peptide 6 | DX$^a$AYHLGELVWX$^b$TKK | Hcy | Hcy | — | Disulfide bond | A | A | 8 |
| 7 Cyclic peptide 7 | DX$^a$AYHLGELVWX$^b$TKK | Dap (ace-tyl) | Hcy | — | Thioether bond | A | A | 9 |
| 8 Cyclic peptide 8 | DX$^a$AYHLGELVWX$^b$TKK | Dab (ace-tyl) | Hcy | — | Thioether bond | A | A | 10 |
| 9 Cyclic peptide 9 | DX$^a$AYHLGELVWX$^b$TKK | Orn (ace-tyl) | Hcy | — | Thioether bond | A | A | 11 |
| 10 Cyclic peptide 10 | DX$^a$AYHLGELVWX$^b$TKK | Hcy | Dab (ace-tyl) | — | Thioether bond | A | A | 12 |
| 11 Cyclic peptide 11 | DX$^a$AYHLGELVWX$^b$TKK | Hcy | Orn (ace-tyl) | — | Thioether bond | A | A | 13 |
| 12 Cyclic peptide 12 | DX$^a$AYHLGELVWX$^b$TKK | Hcy | Lys (ace-tyl) | — | Thioether bond | A | A | 14 |

Examples 13 to 22

Based on Example 1, cyclic peptides 13 to 22 were synthesized, and the relative binding activity and the chemical resistance were evaluated.

The following codes in Table 4 mean the following substances.

Lys (acetyl): amino acid residue derived from N-ε-chloroacetyl-L-lysine

Hcy: amino acid residue derived from L-homocysteine
HmS: amino acid residue derived from L-homoserine
HmY: amino acid residue derived from L-homotyrosine Due to the reaction between a chloroacetyl group and a thiol group, a thioether bond is formed between the amino acid residues in the cross-linked portion, and hence the amino acid residues are cross-linked.

Table 4 shows the structures of the cyclic peptides of Examples 13 to 22 and the evaluation results of the relative binding activity and the chemical resistance.

TABLE 4

| | Identification name | Amino acid sequence (N terminal → C terminal) | Amino acid residue in cross-linked portion $X^a$ | Amino acid residue in cross-linked portion $X^b$ | Special amino acid residue $X^\alpha$ | Cross-linked structure | Relative binding activity | Chemical resistance | SEQ ID NO: |
|---|---|---|---|---|---|---|---|---|---|
| Example 13 | Cyclic peptide 13 | DX$^a$AYHLGELVWX$^b$SKK | Lys (acetyl) | Hcy | — | Thioether bond | A | B | 15 |
| 14 | Cyclic peptide 14 | DX$^a$AYHLGELVWX$^b$X$^\alpha$KK | Lys (acetyl) | Hcy | HmS | Thioether bond | A | A | 16 |
| 15 | Cyclic peptide 15 | DX$^a$AYHLGELVWX$^b$DKK | Lys (acetyl) | Hcy | — | Thioether bond | A | A | 17 |
| 16 | Cyclic peptide 16 | DX$^a$AYHLGELVWX$^b$EKK | Lys (acetyl) | Hcy | — | Thioether bond | A | A | 18 |
| 17 | Cyclic peptide 17 | DX$^a$AYHLGELVWX$^b$YKK | Lys (acetyl) | Hcy | — | Thioether bond | A | A | 19 |
| 18 | Cyclic peptide 18 | DX$^a$AYHLGELVWX$^b$X$^\alpha$KK | Lys (acetyl) | Hcy | HmY | Thioether bond | A | A | 20 |
| 19 | Cyclic peptide 19 | SX$^a$AYHLGELVWX$^b$TKK | Lys (acetyl) | Hcy | — | Thioether bond | A | B | 21 |
| 20 | Cyclic peptide 20 | TX$^a$AYHLGELVWX$^b$TKK | Lys (acetyl) | Hcy | — | Thioether bond | A | A | 22 |
| 21 | Cyclic peptide 21 | X$^\alpha$X$^a$AYHLGELVWX$^b$TKK | Lys (acetyl) | Hcy | HmS | Thioether bond | A | A | 23 |
| 22 | Cyclic peptide 22 | EV$^a$AYHLGELVWX$^b$TKK | Lys (acetyl) | Hcy | — | Thioether bond | A | A | 24 |

Examples 23 to 53

Based on Example 1, cyclic peptides 23 to 53 were synthesized, and the relative binding activity and the chemical resistance were evaluated.

The following codes in Table 5 mean the following substances.

Lys (acetyl): amino acid residue derived from N-ε-chloroacetyl-L-lysine

Hcy: amino acid residue derived from L-homocysteine

Due to the reaction between a chloroacetyl group and a thiol group, a thioether bond is formed between the amino acid residues in the cross-linked portion, and hence the amino acid residues are cross-linked.

Table 5 shows the structures of the cyclic peptides of Examples 23 to 53 and the evaluation results of the relative binding activity and the chemical resistance.

TABLE 5

| | Identification name | Amino acid sequence (N terminal → C terminal) | Amino acid residue in cross-linked portion $X^a$ | Amino acid residue in cross-linked portion $X^b$ | Special amino acid residue $X^\alpha$ | Cross-linked structure | Relative binding activity | Chemical resistance | SEQ ID NO: |
|---|---|---|---|---|---|---|---|---|---|
| Example 23 | Cyclic peptide 23 | DX$^a$AAYHLGELVWX$^b$TKK | Lys (acetyl) | Hcy | — | Thioether bond | A | A | 25 |

TABLE 5-continued

| Identification name | Cyclic peptide Amino acid sequence (N terminal → C terminal) | Amino acid residue in cross-linked portion $X^a$ | | Special amino acid residue $X^\alpha$ | Cross-linked structure | Performance evaluation | | SEQ ID NO: |
| --- | --- | --- | --- | --- | --- | --- | --- | --- |
| | | | $X^b$ | | | Relative binding activity | Chemical resistance | |
| 24 Cyclic peptide 24 | DX$^a$AAAYHLGELVWX$^b$TKK | Lys (acetyl) | Hcy | — | Thioether bond | A | A | 26 |
| 25 Cyclic peptide 25 | DX$^a$AAAAYHLGELVWX$^b$TKK | Lys (acetyl) | Hcy | — | Thioether bond | B | A | 27 |
| 26 Cyclic peptide 26 | DX$^a$SYHLGELVWX$^b$TKK | Lys (acetyl) | Hcy | — | Thioether bond | A | B | 28 |
| 27 Cyclic peptide 27 | DX$^a$TYHLGELVWX$^b$TKK | Lys (acetyl) | Hcy | — | Thioether bond | A | A | 29 |
| 28 Cyclic peptide 28 | DX$^a$AFHLGELVWX$^b$TKK | Lys (acetyl) | Hcy | — | Thioether bond | A | A | 30 |
| 29 Cyclic peptide 29 | DX$^a$AHHLGELVWX$^b$TKK | Lys (acetyl) | Hcy | — | Thioether bond | A | A | 31 |
| 30 Cyclic peptide 30 | DX$^a$AVHLGELVWX$^b$TKK | Lys (acetyl) | Hcy | — | Thioether bond | A | A | 32 |
| 31 Cyclic peptide 31 | DX$^a$AMHLGELVWX$^b$TKK | Lys (acetyl) | Hcy | — | Thioether bond | A | A | 33 |
| 32 Cyclic peptide 32 | DX$^a$AYYLGELVWX$^b$TKK | Lys (acetyl) | Hcy | — | Thioether bond | A | A | 34 |
| 33 Cyclic peptide 33 | DX$^a$AYWLGELVWX$^b$TKK | Lys (acetyl) | Hcy | — | Thioether bond | A | A | 35 |
| 34 Cyclic peptide 34 | DX$^a$AYHMGELVWX$^b$TKK | Lys (acetyl) | Hcy | — | Thioether bond | A | A | 36 |
| 35 Cyclic peptide 35 | DX$^a$AYHFGELVWX$^b$TKK | Lys (acetyl) | Hcy | — | Thioether bond | A | A | 37 |
| 36 Cyclic peptide 36 | DX$^a$AYHHGELVWX$^b$TKK | Lys (acetyl) | Hcy | — | Thioether bond | A | A | 38 |
| 37 Cyclic peptide 37 | DX$^a$AYHVGELVWX$^b$TKK | Lys (acetyl) | Hcy | — | Thioether bond | A | A | 39 |
| 38 Cyclic peptide 38 | DX$^a$AYHIGELVWX$^b$TKK | Lys (acetyl) | Hcy | — | Thioether bond | A | A | 40 |
| 39 Cyclic peptide 39 | DX$^a$AYHNGELVWX$^b$TKK | Lys (acetyl) | Hcy | — | Thioether bond | A | A | 41 |
| 40 Cyclic peptide 40 | DX$^a$AYHWGELVWX$^b$TKK | Lys (acetyl) | Hcy | — | Thioether bond | A | A | 42 |

TABLE 5-continued

Cyclic peptide

| Identification name | Amino acid sequence (N terminal → C terminal) | Amino acid residue in cross-linked portion $X^a$ | Amino acid residue in cross-linked portion $X^b$ | Special amino acid residue $X^\alpha$ | Cross-linked structure | Relative binding activity | Chemical resistance | SEQ ID NO: |
|---|---|---|---|---|---|---|---|---|
| 41 Cyclic peptide 41 | DX$^a$AYHLDELVWX$^b$TKK | Lys (acetyl) | Hcy | — | Thioether bond | A | A | 43 |
| 42 Cyclic peptide 42 | DX$^a$AYHLEELVWX$^b$TKK | Lys (acetyl) | Hcy | — | Thioether bond | A | A | 44 |
| 43 Cyclic peptide 43 | DX$^a$AYHLGDLVWX$^b$TKK | Lys (acetyl) | Hcy | — | Thioether bond | A | A | 45 |
| 44 Cyclic peptide 44 | DX$^a$AYHLGKLVWX$^b$TKK | Lys (acetyl) | Hcy | — | Thioether bond | A | A | 46 |
| 45 Cyclic peptide 45 | DX$^a$AYHLGRLVWX$^b$TKK | Lys (acetyl) | Hcy | — | Thioether bond | A | A | 47 |
| 46 Cyclic peptide 46 | DX$^a$AYHLGHLVWX$^b$TKK | Lys (acetyl) | Hcy | — | Thioether bond | A | A | 48 |
| 47 Cyclic peptide 47 | DX$^a$AYHLGMLVWX$^b$TKK | Lys (acetyl) | Hcy | — | Thioether bond | A | A | 49 |
| 48 Cyclic peptide 48 | DX$^a$AYHLGNLVWX$^b$TKK | Lys (acetyl) | Hcy | — | Thioether bond | A | A | 50 |
| 49 Cyclic peptide 49 | DX$^a$AVHLGEIVWX$^b$TKK | Lys (acetyl) | Hcy | — | Thioether bond | A | A | 51 |
| 50 Cyclic peptide 50 | DX$^a$AYHLGEMVWX$^b$TKK | Lys (acetyl) | Hcy | — | Thioether bond | A | A | 52 |
| 51 Cyclic peptide 51 | DX$^a$AYHLGEKVWX$^b$TKK | Lys (acetyl) | Hcy | — | Thioether bond | A | A | 53 |
| 52 Cyclic peptide 52 | DX$^a$AYHLGERVWX$^b$TKK | Lys (acetyl) | Hcy | — | Thioether bond | B | B | 54 |
| 53 Cyclic peptide 53 | DX$^a$AYHLGELIWX$^b$TKK | Lys (acetyl) | Hcy | — | Thioether bond | A | A | 55 |

Examples 54 to 71

Based on Example 1, cyclic peptides 54 to 71 were synthesized, and the relative binding activity and the chemical resistance were evaluated.

The following code in Table 6 means the following substance.

Hcy: amino acid residue derived from L-homocysteine

Due to the reaction between side-chain thiol groups, a disulfide bond is formed between the amino acid residues in the cross-linked portion, and hence the amino acid residues are cross-linked.

Table 6 shows the structures of the cyclic peptides of Examples 54 to 71 and the evaluation results of the relative binding activity and the chemical resistance.

Comparative Example 1

Based on Example 1, a cyclic peptide 91 was synthesized, and the relative binding activity and the chemical resistance were evaluated.

The following codes in Table 6 mean the following substances.

Glu: amino acid residue derived from L-glutamic acid
Lys: amino acid residue derived from L-lysine Due to the reaction between a carboxy group and an amino group, an amide bond is formed between the amino acid residues in the cross-linked portion, and hence the amino acid residues are cross-linked.

Table 6 shows the structure of the cyclic peptide of Comparative Example 1 and the evaluation results of the relative binding activity and the chemical resistance.

Comparative Example 2

Based on Example 1, a cyclic peptide 92 was synthesized, and the relative binding activity and the chemical resistance were evaluated.

The following code in Table 6 means the following substance.

Cys: amino acid residue derived from L-cysteine

Due to the reaction between side-chain thiol groups, a disulfide bond is formed between the amino acid residues in the cross-linked portion, and hence the amino acid residues are cross-linked.

Table 6 shows the structure of the cyclic peptide of Comparative Example 2 and the evaluation results of the relative binding activity and the chemical resistance.

TABLE 6

| | | Cyclic peptide | | | | | Performance evaluation | | |
|---|---|---|---|---|---|---|---|---|---|
| | Identification name | Amino acid sequence (N terminal → C terminal) | Amino acid residue in cross-linked portion $X^a$ | $X^b$ | Special amino acid residue $X^\alpha$ | Cross-linked structure | Relative binding activity | Chemical resistance | SEQ ID NO: |
| Example | 54 Cyclic peptide 54 | DX$^a$SYHLGELVWX$^b$TKK | Hcy | Hcy | — | Disulfide bond | A | B | 56 |
| | 55 Cyclic peptide 55 | DX$^a$TYHLGELVWX$^b$TKK | Hcy | Hcy | — | Disulfide bond | A | B | 57 |
| | 56 Cyclic peptide 56 | DX$^a$AWHLGELVWX$^b$TKK | Hcy | Hcy | — | Disulfide bond | A | A | 58 |
| | 57 Cyclic peptide 57 | DX$^a$AFHLGELVWX$^b$TKK | Hcy | Hcy | — | Disulfide bond | A | A | 59 |
| | 58 Cyclic peptide 58 | DX$^a$AHHLGELVWX$^b$TKK | Hcy | Hcy | — | Disulfide bond | B | A | 60 |
| | 59 Cyclic peptide 59 | DX$^a$AYYLGELVWX$^b$TKK | Hcy | Hcy | — | Disulfide bond | A | A | 61 |
| | 60 Cyclic peptide 60 | DX$^a$AYHMGELVWX$^b$TKK | Hcy | Hcy | — | Disulfide bond | A | A | 62 |
| | 61 Cyclic peptide 61 | DX$^a$AYHFGELVWX$^b$TKK | Hcy | Hcy | — | Disulfide bond | A | A | 63 |
| | 62 Cyclic peptide 62 | DX$^a$AYHHGELVWX$^b$TKK | Hcy | Hcy | — | Disulfide bond | A | A | 64 |
| | 63 Cyclic peptide 63 | DX$^a$AYHLGDLVWX$^b$TKK | Hcy | Hcy | — | Disulfide bond | A | A | 65 |
| | 64 Cyclic peptide 64 | DX$^a$AYHLGMLVWX$^b$TKK | Hcy | Hcy | — | Disulfide bond | A | A | 66 |
| | 65 Cyclic peptide 65 | DX$^a$AYHLGHLVWX$^b$TKK | Hcy | Hcy | — | Disulfide bond | A | A | 67 |
| | 66 Cyclic peptide 66 | DX$^a$AYHLGNLVWX$^b$TKK | Hcy | Hcy | — | Disulfide bond | A | A | 68 |

TABLE 6-continued

| | Identification name | Amino acid sequence (N terminal → C terminal) | Amino acid residue in cross-linked portion X^a | Amino acid residue in cross-linked portion X^b | Special amino acid residue X^α | Cross-linked structure | Relative binding activity | Chemical resistance | SEQ ID NO: |
|---|---|---|---|---|---|---|---|---|---|
| 67 | Cyclic peptide 67 | DX^aAYHLGEIVWX^bTKK | Hcy | Hcy | — | Disulfide bond | A | A | 69 |
| 68 | Cyclic peptide 68 | DX^aAYHLGEMVWX^bTKK | Hcy | Hcy | — | Disulfide bond | A | A | 70 |
| 69 | Cyclic peptide 69 | DX^aAYHLGEKVWX^bTKK | Hcy | Hcy | — | Disulfide bond | B | A | 71 |
| 70 | Cyclic peptide 70 | DX^aAYHLGERVWX^bTKK | Hcy | Hcy | — | Disulfide bond | B | B | 72 |
| 71 | Cyclic peptide 71 | DX^aAYHLGELIWX^bTKK | Hcy | Hcy | — | Disulfide bond | B | A | 73 |
| Comparative 1 | Cyclic peptide 91 | DX^aAYHRGELVWX^bTKK | Glu | Lys | — | Amide bond | E (standard) | D | 86 |
| Example 2 | Cyclic peptide 92 | DX^aAYHRGELVWX^bTKK | Cys | Cys | — | Disulfide bond | A | E | 87 |

Examples 72 to 75 and Comparative Example 3

Based on Example 1, cyclic peptides 72 to 75 and a cyclic peptide 93 were synthesized, and the relative binding activity and the chemical resistance were evaluated.

The following codes in Table 7 mean the following substances.

Lys (acetyl): amino acid residue derived from N-ε-chloroacetyl-L-lysine

Pen: amino acid residue derived from L-penicillamine

HmS: amino acid residue derived from L-homoserine

Due to the reaction between a chloroacetyl group and a thiol group, a thioether bond is formed between the amino acid residues in the cross-linked portion, and hence the amino acid residues are cross-linked.

Table 7 shows the structures of the cyclic peptides of Examples 72 to 75 and Comparative Example 3 and the evaluation results of the relative binding activity and the chemical resistance.

Examples 76 to 83 and Comparative Examples 4 to 6

Based on Example 1, cyclic peptides 78 to 91 were synthesized, and the relative binding activity and the chemical resistance were evaluated.

The following codes in Table 7 mean the following substances.

Dap (acetyl): amino acid residue derived from N^3-haloacetyl-L-2,3-diaminopropanoic acid[(2S)-2-amino-3-[(2-haloacetyl)amino]propanoic acid]

Dab (acetyl): amino acid residue derived from N^4-haloacetyl-L-2,4-diaminobutanoic acid[(2S)-2-amino-4-[(2-haloacetyl)amino]butanoic acid]

Orn (acetyl): amino acid residue derived from N-δ-chloroacetyl-L-ornithine

Lys (acetyl): amino acid residue derived from N-ε-chloroacetyl-L-lysine

HmS: amino acid residue derived from L-homoserine

Due to the reaction between a chloroacetyl group and a thiol group, a thioether bond is formed between the amino acid residues in the cross-linked portion, and hence the amino acid residues are cross-linked.

Table 7 shows the structures of the cyclic peptides of Examples 72, 73, 74, and 75 and Comparative Example 3 and the evaluation results of the relative binding activity and the chemical resistance.

TABLE 7

| | | Cyclic peptide | | | | | Performance evaluation | | |
|---|---|---|---|---|---|---|---|---|---|
| | Identification name | Amino acid sequence (N terminal → C terminal) | Amino acid residue in cross-linked portion $X^a$ | | Special amino acid residue $X^\alpha$ | Cross-linked structure | Relative binding activity | Chemical resistance | SEQ ID NO: |
| | | | $X^a$ | $X^b$ | | | | | |
| Example | 72 Cyclic peptide 72 | DX$^a$AYHLGELVWX$^b$TKK | Lys (acetyl) | Pen | — | Thioether bond | A (S) | A | 74 |
| | 73 Cyclic peptide 73 | DX$^a$AYHLGELVWX$^b$TKK | Pen | K (acetyl) | — | Thioether bond | A | A | 75 |
| | 74 Cyclic peptide 74 | DX$^a$AYHRGELVWX$^b$TKK | Lys (acetyl) | Pen | — | Thioether bond | A (S) | B | 76 |
| | 75 Cyclic peptide 75 | DX$^a$AYHLGELVWX$^b$X$^\alpha$KK | Lys (acetyl) | Pen | HmS | Thioether bond | A (S) | B | 77 |
| | 76 Cyclic peptide 76 | DX$^a$AYHLGELVWX$^b$TKK | Dap (acetyl) | Cys | — | Thioether bond | A (S) | B | 78 |
| | 77 Cyclic peptide 77 | DX$^a$AYHLGELVWX$^b$TKK | Dab (acetyl) | Cys | — | Thioether bond | A (S) | B | 79 |
| | 78 Cyclic peptide 78 | DX$^a$AYHLGELVWX$^b$TKK | Orn (acetyl) | Cys | — | Thioether bond | A | B | 80 |
| | 79 Cyclic peptide 79 | DX$^a$AYHLGELVWX$^b$TKK | Lys (acetyl) | Cys | — | Thioether bond | A (S) | B | 81 |
| | 80 Cyclic peptide 80 | DX$^a$AYHLGELVWX$^b$TKK | Cys | Dap (acetyl) | — | Thioether bond | A (S) | B | 82 |
| | 81 Cyclic peptide 81 | DX$^a$AYHLGELVWX$^b$TKK | Cys | Dab (acetyl) | — | Thioether bond | A (S) | B | 83 |
| | 82 Cyclic peptide 82 | DX$^a$AYHLGELVWX$^b$TKK | Cys | Orn (acetyl) | — | Thioether bond | A | B | 84 |
| | 83 Cyclic peptide 83 | DX$^a$AYHLGELVWX$^b$TKK | Cys | Lys (acetyl) | — | Thioether bond | A (S) | B | 85 |
| Comparative | 3 Cyclic peptide 93 | DX$^a$SYHLGELVWX$^b$TKK | Lys (acetyl) | Pen | — | Thioether bond | A | D | 88 |
| Example | 4 Cyclic peptide 94 | DX$^a$SYHLGELVWX$^b$TKK | Lys (acetyl) | Cys | — | Thioether bond | A | E | 89 |
| | 5 Cyclic peptide 95 | DX$^a$AYHRGELVWX$^b$TKK | Lys (acetyl) | Cys | — | Thioether bond | A | E | 90 |
| | 6 Cyclic peptide 96 | X$^\alpha$X$^a$AYHRGELVWX$^b$TKK | Lys (acetyl) | Cys | HmS | Thioether bond | A | E | 91 |

Description of Results of Examples and Comparative Examples

Examples 1 to 6

All of the cyclic peptides 1 to 6 of Examples 1 to 6 were graded A by the evaluation of the relative binding activity and had excellent relative binding activity.

Except for the cyclic peptide 2 of Example 2, the cyclic peptides 1 to 6 of Examples 1 to 6 were graded A by the evaluation of the chemical resistance and had excellent chemical resistance.

Although both the cyclic peptide 2 of Example 2 and the cyclic peptide 6 of Example 6 had a cross-linked structure formed by a disulfide bond, they had a difference in that the cyclic peptide 2 was graded B by the evaluation of the chemical resistance while the cyclic peptide 6 was graded A by the evaluation of the chemical resistance. Presumably, this is because the cyclic peptide 2 had an amino acid sequence of AYHRGELVW (SEQ ID NO: 2) in the cyclic portion while the cyclic peptide 6 had an amino acid sequence of AYHLGELVW (SEQ ID NO: 1) in the cyclic portion. At this point in time, the mechanism that makes the cyclic peptides exhibit different levels of chemical resistance cannot be clearly explained.

Examples 7 to 12

Examples 7 to 9 and Examples 10 to 12 are obtained by changing the type of amino acid residue derived from an amino acid having a chloroacetyl group on a side chain. Examples 7 to 9 and Examples 10 to 12 have a relationship established by changing the positions of the amino acid residue derived from an amino acid having a chloroacetyl group on a side chain and the amino acid residue derived from an amino acid, other than L-cysteine and D-cysteine, having a thiol group on a side chain.

All of the cyclic peptides 7 to 12 of Examples 7 to 12 were graded A by the evaluation of the relative binding activity and the chemical resistance, and had excellent relative binding activity and chemical resistance.

Examples 13 to 22

The cyclic peptides 13 to 22 of Examples 13 to 22 are examples obtained by changing the amino acid residue derived from an amino acid having a carboxy group on a side chain on the outside of the cyclic portion or an amino acid residue derived from an amino acid having a hydroxy group on a side chain.

The cyclic peptide 13 (Example 13) having the amino acid residue derived from L-serine (amino acid having a hydroxy group on a side chain) on the C-terminal side of the cyclic portion and the cyclic peptide 19 (Example 19) having the same amino acid residue on the N-terminal side were graded B by the evaluation of the chemical resistance. Except for these cyclic peptides, all of the cyclic peptides 14 to 18 (Examples 14 to 18) and the cyclic peptides 20 to 22 (Examples 20 to 22) were graded A by the evaluation of the relative binding activity and the chemical resistance, and these cyclic peptides had excellent relative binding activity and chemical resistance.

Examples 23 to 53

The cyclic peptides 23 to 53 of Examples 23 to 53 are examples obtained by changing the type of amino acid residue on the inside of the cyclic portion in a case where the cross-linked structure is a thioether bond.

Examples 54 to 71

The cyclic peptides 54 to 71 of Examples 54 to 71 are examples obtained by changing the type of amino acid residue on the inside of the cyclic portion in a case where the cross-linked structure is a disulfide bond.

Examples 72 to 75 and Comparative Example 3

The cyclic peptides 72 to 75 of Examples 72 to 75 and the cyclic peptide 93 of Comparative Example 3 are examples obtained in a case where the cross-linked structure is a thioether bond. In these cyclic peptides, the amino acid having a thiol group on a side chain is L-penicillamine.

The cyclic peptide 93 of Comparative Example 3 including L-serine in the cyclic portion was graded A by the evaluation of the relative binding activity but graded D by the evaluation of the chemical resistance.

Examples 76 to 83 and Comparative Examples 4 to 6

The cyclic peptides 76 to 83 of Examples 76 to 83 and the cyclic peptides 94 to 96 of Comparative Examples 4 to 6 are examples obtained in a case where the cross-linked structure is a thioether bond. In these cyclic peptides, the amino acid having a thiol group on a side chain is L-cysteine.

All of Comparative Example 4 including L-serine in the cyclic portion, Comparative Example 5 including L-aspartic acid in the cyclic portion, and Comparative Example 6 including L-homoserine on the outside of the N-terminal side of the cyclic portion were graded E by the evaluation of chemical resistance, and had poor chemical resistance.

Presumably, this is because either or both of the hydroxy group and the carboxy group on a side chain of the amino acid residue exert an influence. However, at this point in time, why the chemical resistance of the above examples is significantly poorer than that of Examples 76 to 83 cannot be clearly explained.

SUMMARY

To summarize, as a cross-linked structure, a thioether bond in which an L-homocysteine residue is involved tends to exhibit the highest stability, a disulfide bond between L-homocysteine residues tends to exhibit the second highest stability, a thioether bond in which L-penicillamine is involved tends to exhibit the third highest stability, and a thioether bond in which L-cysteine is involved tends to exhibit the fourth highest stability.

Example A

<Results of Experiment Performed in Human Plasma>
<<Evaluation of Plasma Stability>>

The stability of the cyclic peptide 5 manufactured in Example 5 in human plasma (manufactured by ProMedDX) was evaluated.

Each of the peptides was prepared as a 5 µM aqueous solution, and 2 µL of each of the aqueous solutions was added to 20 µL of the human plasma and left to stand for 20 minutes at room temperature. After 20 minutes, 100 µL of methanol (manufactured by Wako Pure Chemical Industries, Ltd.) was added thereto such that the reaction stopped. After being stirred, the solution was subjected to centrifugation, and the supernatant was collected and named 20-minute sample. Meanwhile, 100 μL of methanol was added to 20 μL of the human plasma, 2 μL of the aqueous peptide solution was added thereto, the solution was stirred and subjected to centrifugation, and the supernatant was collected. The collected supernatant was named 0-minute sample.

Each of the samples was quantified using a mass spectrometer TRIPLE QUAD 5500 (manufactured by AB Sciex Pte. Ltd.). By regarding the quantified value of the 0-minute sample as 100%, the quantified value of the 20-minute sample was calculated as a residual rate.

(Evaluation Standards for Residual Rate)

| | |
|---|---|
| The rate of change in the binding amount was higher than 90% | A |
| The rate of change in the binding amount was higher than 80% and equal to or lower than 90% | B |
| The rate of change in the binding amount was higher than 70% and equal to or lower than 80% | C |
| The rate of change in the binding amount was higher than 50% and equal to or lower than 70% | D |
| The rate of change in the binding amount was equal to or lower than 50% | E |

The structure of the cyclic peptide and the evaluation result are shown in the corresponding column in Table 8.

Example B

The stability of the cyclic peptide 6 manufactured in Example 6 in the human plasma was evaluated in the same manner as in Example A. The structure of the cyclic peptide and the evaluation result are shown in the corresponding column in Table 8.

Comparative Example C

The stability of the cyclic peptide 91 manufactured in Comparative Example 1 in the human plasma was evaluated in the same manner as in Example A. The structure of the cyclic peptide and the evaluation result are shown in the corresponding column in Table 8.

TABLE 8

| | Cyclic peptide | | | | | | |
|---|---|---|---|---|---|---|---|
| | Identification name | Amino acid sequence (N terminal → C terminal) | Amino acid residue in cross-linked portion $X^a$ | $X^b$ | Cross-linked structure | Rate of change in binding amount (evaluation) | SEQ ID NO: |
| Example A | Cyclic peptide 5 | DXaAYHLGELVWXbTKK | Lys (acetyl) | Hcy | Thioether bond | A | 7 |
| Example B | Cyclic peptide 6 | DXaAYHLGELVWXbTKK | Hcy | Hcy | Disulfide bond | A | 8 |
| Comparative Example C | Cyclic peptide 91 | DXCaAYHRGELVWXbTKKGlu | | Lys | Amide bond | E | 86 |

<<Description of Results>>

The rate of change in the binding amount (residual rate) of the cyclic peptide 5 (Example A) and the cyclic peptide 6 (Example B) in the human plasma was higher than 90%. The cyclic peptides 5 and 6 exhibited excellent stability in the human plasma.

In contrast, the rate of change in the binding amount (residual rate) of the cyclic peptide 91 (Comparative Example C) was equal to or lower than 50%. The cyclic peptide 91 exhibited poor stability in the human plasma.

The stability in the human plasma is a characteristic which is important in a case where the cyclic peptide of the present invention is used as an antibody drug conjugate or a pharmaceutical preparation. The higher the rate of change in the binding amount (residual rate) is, the more difficult it is for the cyclic peptide to be dissociated from the drug in the blood. Therefore, a high residual rate is advantageous for accurate drug delivery to a target and for inhibiting side effects.

[Sequence List]

International Patent Application No. W-5923PCT based on International Patent Cooperation Treaty, Cyclic Peptide, Affinity ChroJP16081353 20161021—00260157151602210379normal20161021161101201609151052110950_P1AP10 1_W-_25.app

What is claimed is:

1. A cyclic peptide represented by Formula (I),

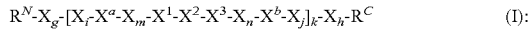 (I)

in Formula (I), $R^N$ represents an amino group, an amino group have undergone N-acetylation, an amino group have undergone N-formylation, or an amino group have undergone N-acylation;

$R^C$ represents a carboxy group or a carboxy group have undergone amidation;

$X^1$ represents an L-leucine residue, an L-isoleucine residue, an L-methionine residue, an L-lysine residue, or an L-arginine residue;

$X^2$ represents an L-valine residue or an L-isoleucine residue;

$X^3$ represents an L-tryptophan residue;

$X^a$ is an amino acid residue selected from the group consisting of (2S)-2-amino-3-[(2-chloroacetyl)amino] propanoic acid residue, (2R)-2-amino-3-[(2-chloroacetyl)amino]propanoic acid residue, (2S)-2-amino-4-[(2-chloroacetyl)amino]butanoic acid residue, (2R)-2-amino-4-[(2-chloroacetyl)amino]butanoic acid residue, N-δ-chloroacetyl-L-ornithine residue, N-δ-chloroacetyl-D-ornithine residue, N-ε-chloroacetyl-L-lysine residue, and N-ε-chloroacetyl-D-lysine residue, $X^b$ is an L-homocysteine residue or D-homocysteine residue, and $X^a$ and $X^b$ are bonded to each other through a thioether bond;

$X_g$, $X_h$, $X_i$, $X_j$, $X_m$, and $X_n$ each represent g consecutive X's, h consecutive X's, i consecutive X's, j consecutive X's, m consecutive X's, and n consecutive X's;

X represents an amino acid residue, and in a case where there is a plurality of X's, the plurality of X's may be the same as or different from each other;

g, h, i, and j each independently represent an integer equal to or greater than 0;

m and n are integers satisfying 0≤m≤9, 0≤n≤9, and 3≤m+n≤9 simultaneously; and k is an integer equal to or greater than 1, and in a case where k≥2, $X^1$, $X^2$, $X^3$, $X^a$, $X^b$, $X_i$, $X_j$, $X_m$, and $X_n$ in a repeating unit $[X_i\text{-}X^a\text{-}X_m\text{-}X^1\text{-}X^2\text{-}X^3\text{-}X_n\text{-}X^b\text{-}X_j]$ each may be the same or different between the repeating units.

2. The cyclic peptide according to claim 1 that is represented by Formula (IA),

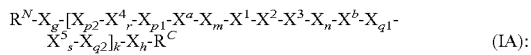 (IA)

in Formula (IA), $R^N$, $R^C$, $X^1$, $X^2$, $X^3$, $X^a$, $X^b$, $X_g$, $X_h$, $X_m$, $X_n$, X, g, h, m, n, and k have the same definitions as those in Formula (I);

$X^4_r$, $X^5_s$, $X_{p1}$, $X_{p2}$, $X_{q1}$, and $X_{q2}$ each represent r consecutive $X^4$'s, s consecutive $X^5$'s, p1 consecutive X's, p2 consecutive X's, q1 consecutive X's, and q2 consecutive X's;

$X^4$ and $X^5$ each independently represent an amino acid residue having a carboxy group on a side chain or an amino acid residue having a hydroxy group on a side chain, and in a case where there is a plurality of $X^4$'s or $X^5$'s, the plurality of $X^4$'s or $X^5$'s may be the same as or different from each other;

p1, p2, q1, and q2 each independently represent an integer equal to or greater than 0;

r and s each represent an integer satisfying 0≤r≤5, 0≤s≤5, and 1≤Max (r,s)≤5, where Max (r,s) represents a larger one between two numbers represented by r and s in a case where r≠s and represents r or s in a case where r=s; and in a case where k≥2, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}\text{-}X^4_r\text{-}X_{p1}\text{-}X^a\text{-}X_m\text{-}X^1\text{-}X^2\text{-}X^3\text{-}X_n\text{-}X^b\text{-}X_{q1}\text{-}X^5_s\text{-}X_{q2}]$ each may be the same or different between the repeating units.

3. The cyclic peptide according to claim 1 that is represented by Formula (IB),

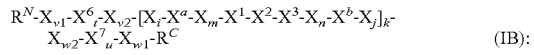 (IB)

in Formula (IB), $R^N$, $R^C$, $X^1$, $X^2$, $X^3$, $X^a$, $X^b$, $X_i$, $X_j$, $X_m$, $X_n$, X, i, j, m, n, and k have the same definitions as those in Formula (I);

$X^6_t$, $X^7_u$, $X_{v1}$, $X_{v2}$, $X_{w1}$, and $X_{w2}$ each represent t consecutive $X^6$'s, u consecutive $X^7$'s, v1 consecutive X's, v2 consecutive X's, w1 consecutive X's, and w2 consecutive X's;

$X^6$ and $X^7$ each independently represent an amino acid residue having an immobilizing functional group on a side chain, and in a case where there is a plurality of $X^6$'s or $X^7$'s, the plurality of $X^6$'s or $X^7$'s may be the same as or different from each other;

t and u each represent an integer satisfying 0≤t≤5, 0≤u≤5, and 1≤Max (t,u)≤5, where Max (t,u) represents a larger one between two numbers represented by t and u in a case where t≠u and represents t or u in a case where t=u;

v1, v2, w1, and w2 each independently represent an integer equal to or greater than 0; and in a case where k≥2, $X^1$, $X^2$, $X^3$, $X^a$, $X^b$, $X_i$, $X_j$, $X_m$, and $X_n$ in a repeating unit $[X_i\text{-}X^a\text{-}X_m\text{-}X^1\text{-}X^2\text{-}X^3\text{-}X_n\text{-}X^b\text{-}X_j]$ each may be the same or different between the repeating units.

4. The cyclic peptide according to claim 1 that is represented by Formula (IC),

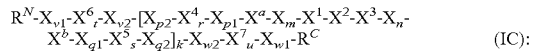 (IC)

in Formula (IC), $R^N$, $R^C$, $X^1$, $X^2$, $X^3$, $X^a$, $X^b$, $X_m$, $X_n$, X, m, n, and k have the same definitions as those in Formula (I);

$X_{p1}$, $X_{p2}$, $X_{q1}$, $X_{q2}$, $X^4_r$, $X^5_s$, $X^6_t$, $X^7_u$, $X_{v1}$, $X_{v2}$, $X_{w1}$, and $X_{w2}$ each represent p1 consecutive X's, p2 consecutive X's, q1 consecutive X's, q2 consecutive X's, r consecutive $X^4$'s, s consecutive $X^5$'s, t consecutive $X^6$'s, u consecutive $X^7$'s, v1 consecutive X's, v2 consecutive X's, w1 consecutive X's, and w2 consecutive X's';

$X^4$ and $X^5$ each independently represent an amino acid residue having a carboxy group on a side chain or an amino acid residue having a hydroxy group on a side chain, and in a case where there is a plurality of $X^4$'s or $X^5$'s, the plurality of $X^4$'s or $X^5$'s may be the same as or different from each other;

$X^6$ and $X^7$ each independently represent an amino acid residue having an immobilizing functional group on a side chain, and in a case where there is a plurality of $X^6$ or $X^7$, the plurality of $X^6$'s or $X^7$'s may be the same as or different from each other;

p1, p2, q1, and q2 each independently represent an integer equal to or greater than 0;

r and s each represent an integer satisfying 0≤r≤5, 0≤s≤5, and 1≤Max (r,s)≤5, where Max (r,s) represents a larger one between two numbers represented by r and s in a case where r≠s and represents r or s in a case where r=s;

t and u each represent an integer satisfying 0≤t≤5, 0≤u≤5, and 1≤Max (t,u) ≤5, where Max (t,u) represents a larger one between two numbers represented by t and u in a case where t≠u and represents t or u in a case where t=u;

v1, v2, w1, and w2 each independently represent an integer equal to or greater than 0; and in a case where k≥2, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}\text{-}X^4_r\text{-}X_{p1}\text{-}X^a\text{-}X_m\text{-}X^1\text{-}X^2\text{-}X^3\text{-}X_n\text{-}X^b\text{-}X_{q1}\text{-}X^5_s\text{-}X_{q2}]$ each may be the same or different between the repeating units.

5. The cyclic peptide according to claim 1, wherein 8≤g+h+k×(i+j+m+n+5)≤50.

6. The cyclic peptide according to claim 2, wherein 8≤g+h+k×(m+n+p1+p2+q1+q2+5)≤50.

7. The cyclic peptide according to claim 3, wherein 8≤v1+v2+w1+w2+t+u+k×(i+j+m+n+5)≤50.

8. The cyclic peptide according to claim 4, wherein 8≤v1+v2+w1+w2+t+u+k×(m+n+p1+p2+q1+q2+5)≤50.

9. The cyclic peptide according to claim 2, wherein the amino acid having a carboxy group on a side chain is at least one kind of amino acid selected from the group consisting of L-aspartic acid, D-aspartic acid, L-glutamic acid, D-glutamic acid, L-homoglutamic acid, and D-homoglutamic acid, and the amino acid having a hydroxy group on a side chain is at least one kind of amino acid selected from the group consisting of L-serine, D-serine, L-homoserine, D-homoserine, L-tyrosine, D-tyrosine, L-threonine, D-threonine, L-allothreonine, and D-allothreonine.

10. The cyclic peptide according to claim 9, wherein the amino acid having a carboxy group on a side chain is L-aspartic acid, and the amino acid having a hydroxy group on a side chain is L-threonine.

11. The cyclic peptide according to claim 3, wherein the immobilizing functional group is an amino group or a thiol group.

12. The cyclic peptide according to claim 3, wherein the amino acid having an immobilizing functional group on a side chain is at least one kind of amino acid selected from the group consisting of L-lysine, D-lysine, L-cysteine, D-cysteine, L-homocysteine, and D-homocysteine.

13. The cyclic peptide according to claim 1 that is an antibody binding ligand.

14. The cyclic peptide according to claim 1 that is a linker for labeling antibodies.

15. The cyclic peptide according to claim 1 that is a linker for antibody drug conjugates.

16. The cyclic peptide according to claim 1 that is a drug carrier.

17. An affinity chromatography support comprising:
a water-insoluble support; and
the cyclic peptide according to claim 1,
wherein the water-insoluble support and the cyclic peptide are directly or indirectly bonded to each other.

18. A labeled antibody comprising:
an antibody;
a labeling compound; and
the cyclic peptide according to claim 1,
wherein the antibody and the labeling compound are bonded to each other through the cyclic peptide.

19. A method for preparing the cyclic peptide of claim 1, the method which comprises:
synthesizing a linear peptide represented by Formula (I); and
reacting a side-chain thiol group of the $X^b$ residue with a side-chain chloroacetyl group of the $X^a$ residue, thereby forming a thioether bond.

20. The method of claim 19, wherein the step of synthesizing comprises using synthetic organic chemistry.

21. The method of claim 19, wherein the step of synthesizing comprises using synthetic genetic engineering.

* * * * *

SEQUENCE LISTING

<160> NUMBER OF SEQ ID NOS: 95

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide: Sequence-1

<400> SEQUENCE: 1

Ala Tyr His Leu Gly Glu Leu Val Trp
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide: Sequence-2

<400> SEQUENCE: 2

Ala Tyr His Arg Gly Glu Leu Val Trp
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic: Cyclic_peptide_1
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 3

Asp Xaa Ala Tyr His Arg Gly Glu Leu Val Trp Xaa Thr Lys Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic: Cyclic_peptide_2
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 4

Asp Xaa Ala Tyr His Arg Gly Glu Leu Val Trp Xaa Thr Lys Lys
1               5                   10                  15

```
<210> SEQ ID NO 5
<211> LENGTH: 15
<212> TYPE: PRT
<213> ORGANISM: Artificial Sequence
<220> FEATURE:
<223> OTHER INFORMATION: Synthetic: Cyclic_peptide_3
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      N-delta-chloroacetyl-L-ornithine.

<400> SEQUENCE: 5

Asp Xaa Ala Tyr His Arg Gly Glu Leu Val Trp Xaa Thr Lys Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic: Cyclic_peptide_4
<220> FEATURE:
<221> NAME/KEY: MISC_FEATURE
<223> OTHER INFORMATION: Xaa4 and Xaa14 are bridged by a thioether bond.
<220> FEATURE:
<221> NAME/KEY: MISC_FEATURE
<222> LOCATION: (4)..(4)
<223> OTHER INFORMATION: Xaa4 is an amino acid residue derived from
      N-epsilon-cloroacetyl-L-lysine.
<220> FEATURE:
<221> NAME/KEY: MISC_FEATURE
<222> LOCATION: (14)..(14)
<223> OTHER INFORMATION: Xaa14 is an amino acid residue derived from
      L-homocysteine.

<400> SEQUENCE: 6

Lys Lys Asp Xaa Ala Tyr His Arg Gly Glu Leu Val Trp Xaa Thr
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic: Cyclic_peptide_5
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 7

Asp Xaa Ala Tyr His Leu Gly Glu Leu Val Trp Xaa Thr Lys Lys
1               5                   10                  15
```

```
<210> SEQ ID NO 8
<211> LENGTH: 15
<212> TYPE: PRT
<213> ORGANISM: Artificial Sequence
<220> FEATURE:
<223> OTHER INFORMATION: Synthetic: Cyclic_peptide_6
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 8

Asp Xaa Ala Tyr His Leu Gly Glu Leu Val Trp Xaa Thr Lys Lys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic: Cyclic_peptide_7
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      (2S)-2-amino-3-[(2-chloroacetyl)amino]propanoic acid.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 9

Asp Xaa Ala Tyr His Leu Gly Glu Leu Val Trp Xaa Thr Lys Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic: Cyclic_peptide_8
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      (2S)-2amino-4-[(2-chloroacetyl)amino]butanoic acid.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 10

Asp Xaa Ala Tyr His Leu Gly Glu Leu Val Trp Xaa Thr Lys Lys
1               5                   10                  15
```

```
<210> SEQ ID NO 11
<211> LENGTH: 15
<212> TYPE: PRT
<213> ORGANISM: Artificial Sequence
<220> FEATURE:
<223> OTHER INFORMATION: Synthetic: Cyclic_peptide_9
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-delta-chloroacetyl-L-ornithine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 11

Asp Xaa Ala Tyr His Leu Gly Glu Leu Val Trp Xaa Thr Lys Lys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic: Cyclic_peptide_10
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      (2S)-2-amino-4-[(2-chloroacetyl)amino]butanoic acid.

<400> SEQUENCE: 12

Asp Xaa Ala Tyr His Leu Gly Glu Leu Val Trp Xaa Thr Lys Lys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic: Cyclic_peptide_11
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      homocysteine.
<220> FEATURE:
<221> NAME/KEY: MISC_FEATURE
<222> LOCATION: (12)..(12)
<223> OTHER INFORMATION: Xaa12 is an amino acid residue derived from
      N-delta-chloroacetyl-L-ornithine.

<400> SEQUENCE: 13

Asp Xaa Ala Tyr His Leu Gly Glu Leu Val Trp Xaa Thr Lys Lys
1               5                   10                  15

<210> SEQ ID NO 14
```

```
<211> LENGTH: 15
<212> TYPE: PRT
<213> ORGANISM: Artificial Sequence
<220> FEATURE:
<223> OTHER INFORMATION: Synthetic: Cyclic_peptide_12
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      N-epsilon-chloroacetyl-L-lysine.

<400> SEQUENCE: 14

Asp Xaa Ala Tyr His Leu Gly Glu Leu Val Trp Xaa Thr Lys Lys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic: Cyclic_peptide_13
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 15

Asp Xaa Ala Tyr His Leu Gly Glu Leu Val Trp Xaa Ser Lys Lys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic: Cyclic_peptide_14
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.
<220> FEATURE:
<221> NAME/KEY: MISC_FEATURE
<222> LOCATION: (13)..(13)
<223> OTHER INFORMATION: Xaa13 is an amino acid residue derived from
      L-homoserine.

<400> SEQUENCE: 16

Asp Xaa Ala Tyr His Leu Gly Glu Leu Val Trp Xaa Xaa Lys Lys
```

```
<210> SEQ ID NO 17
<211> LENGTH: 15
<212> TYPE: PRT
<213> ORGANISM: Artificial Sequence
<220> FEATURE:
<223> OTHER INFORMATION: Synthetic: Cyclic_peptide_15
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 17

Asp Xaa Ala Tyr His Leu Gly Glu Leu Val Trp Xaa Asp Lys Lys
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic: Cyclic_peptide_16
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 18

Asp Xaa Ala Tyr His Leu Gly Glu Leu Val Trp Xaa Glu Lys Lys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic: Cyclic_peptide_17
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 19

Asp Xaa Ala Tyr His Leu Gly Glu Leu Val Trp Xaa Tyr Lys Lys
1               5                   10                  15
```

```
<210> SEQ ID NO 20
<211> LENGTH: 15
<212> TYPE: PRT
<213> ORGANISM: Artificial Sequence
<220> FEATURE:
<223> OTHER INFORMATION: Synthetic: Cyclic_peptide_18
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.
<220> FEATURE:
<221> NAME/KEY: MISC_FEATURE
<222> LOCATION: (13)..(13)
<223> OTHER INFORMATION: Xaa13 is an amino acid residue derived from
      L-homotyrosine.

<400> SEQUENCE: 20

Asp Xaa Ala Tyr His Leu Gly Glu Leu Val Trp Xaa Xaa Lys Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic: Cyclic_peptide_19
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 21

Ser Xaa Ala Tyr His Leu Gly Glu Leu Val Trp Xaa Thr Lys Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic: Cyclic_peptide_20
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.
```

<400> SEQUENCE: 22

Thr Xaa Ala Tyr His Leu Gly Glu Leu Val Trp Xaa Thr Lys Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic: Cyclic_peptide_21
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (1)..(1)
<223> OTHER INFORMATION: Xaa1 is an amino acid residue derived from
      L-homoserine.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 23

Xaa Xaa Ala Tyr His Leu Gly Glu Leu Val Trp Xaa Thr Lys Lys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic: Cyclic_peptide_22
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 24

Glu Xaa Ala Tyr His Leu Gly Glu Leu Val Trp Xaa Thr Lys Lys
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic: Cyclic_peptide_23
<220> FEATURE:
<221> NAME/KEY: MISC_FEATURE
<223> OTHER INFORMATION: Xaa2 and Xaa13 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE -continued

```
<222> LOCATION: (13)..(13)
<223> OTHER INFORMATION: Xaa13 is an amino acid residue derived from
      L-homocysteine.

<400> SEQUENCE: 25

Asp Xaa Ala Ala Tyr His Leu Gly Glu Leu Val Trp Xaa Thr Lys Lys
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: Synthetic: Cyclic_peptide_24
<220> FEATURE:
<221> NAME/KEY: MISC_FEATURE
<223> OTHER INFORMATION: Xaa2 and Xaa14 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (14)..(14)
<223> OTHER INFORMATION: Xaa14 is an amino acid residue derived from
      L-homocysteine.

<400> SEQUENCE: 26

Asp Xaa Ala Ala Ala Tyr His Leu Gly Glu Leu Val Trp Xaa Thr Lys
1               5                   10                  15

Lys

<210> SEQ ID NO 27
<211> LENGTH: 18
<212> TYPE: PRT
<213> ORGANISM: Artificial Sequence
<220> FEATURE:
<223> OTHER INFORMATION: Synthetic: Cyclic_peptide_25
<220> FEATURE:
<221> NAME/KEY: MISC_FEATURE
<223> OTHER INFORMATION: Xaa2 and Xaa15 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (15)..(15)
<223> OTHER INFORMATION: Xaa15 is an amino acid residue derived from
      L-homocysteine.

<400> SEQUENCE: 27

Asp Xaa Ala Ala Ala Ala Tyr His Leu Gly Glu Leu Val Trp Xaa Thr
1               5                   10                  15

Lys Lys

<210> SEQ ID NO 28
<211> LENGTH: 15
<212> TYPE: PRT
<213> ORGANISM: Artificial Sequence
<220> FEATURE:
<223> OTHER INFORMATION: Synthetic: Cyclic_peptide_26
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
```

```
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 28

Asp Xaa Ser Tyr His Leu Gly Glu Leu Val Trp Xaa Thr Lys Lys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic: Cyclic_peptide_27
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 29

Asp Xaa Thr Tyr His Leu Gly Glu Leu Val Trp Xaa Thr Lys Lys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic: Cyclic_peptide_28
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 30

Asp Xaa Ala Phe His Leu Gly Glu Leu Val Trp Xaa Thr Lys Lys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic: Cyclic_peptide_29
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
```

```
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 31

Asp Xaa Ala His His Leu Gly Glu Leu Val Trp Xaa Thr Lys Lys
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic: Cyclic_peptide_30
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 32

Asp Xaa Ala Val His Leu Gly Glu Leu Val Trp Xaa Thr Lys Lys
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic: Cyclic_peptide_31
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 33

Asp Xaa Ala Met His Leu Gly Glu Leu Val Trp Xaa Thr Lys Lys
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic: Cyclic_peptide_32
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
```

```
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 34

Asp Xaa Ala Tyr Tyr Leu Gly Glu Leu Val Trp Xaa Thr Lys Lys
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic: Cyclic_peptide_33
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 35

Asp Xaa Ala Tyr Trp Leu Gly Glu Leu Val Trp Xaa Thr Lys Lys
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic: Cyclic_peptide_34
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 36

Asp Xaa Ala Tyr His Met Gly Glu Leu Val Trp Xaa Thr Lys Lys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic: Cyclic_peptide_35
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
```

```
<222> LOCATION: (12)..(12)
<223> OTHER INFORMATION: Xaa12 is an amino acid residue derived from
      L-homocysteine.

<400> SEQUENCE: 37

Asp Xaa Ala Tyr His Phe Gly Glu Leu Val Trp Xaa Thr Lys Lys
1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic: Cyclic_peptide_36
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 38

Asp Xaa Ala Tyr His His Gly Glu Leu Val Trp Xaa Thr Lys Lys
1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic: Cyclic_peptide_37
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 39

Asp Xaa Ala Tyr His Val Gly Glu Leu Val Trp Xaa Thr Lys Lys
1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic: Cyclic_peptide_38
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
```

-continued

```
<223> OTHER INFORMATION: Xaa12 is an amino acid residue derived from
      L-homocysteine.

<400> SEQUENCE: 40

Asp Xaa Ala Tyr His Ile Gly Glu Leu Val Trp Xaa Thr Lys Lys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic: Cyclic_peptide_39
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 41

Asp Xaa Ala Tyr His Asn Gly Glu Leu Val Trp Xaa Thr Lys Lys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic: Cyclic_peptide_40
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 42

Asp Xaa Ala Tyr His Trp Gly Glu Leu Val Trp Xaa Thr Lys Lys
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic: Cyclic_peptide_41
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
```

-continued

L-homocysteine.

<400> SEQUENCE: 43

Asp Xaa Ala Tyr His Leu Asp Glu Leu Val Trp Xaa Thr Lys Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic: Cyclic_peptide_42
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 44

Asp Xaa Ala Tyr His Leu Glu Glu Leu Val Trp Xaa Thr Lys Lys
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic: Cyclic_peptide_43
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 45

Asp Xaa Ala Tyr His Leu Gly Asp Leu Val Trp Xaa Thr Lys Lys
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic: Cyclic_peptide_44
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 46

Asp Xaa Ala Tyr His Leu Gly Lys Leu Val Trp Xaa Thr Lys Lys
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic: Cyclic_peptide_45
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 47

Asp Xaa Ala Tyr His Leu Gly Arg Leu Val Trp Xaa Thr Lys Lys
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic: Cyclic_peptide_46
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 48

Asp Xaa Ala Tyr His Leu Gly His Leu Val Trp Xaa Thr Lys Lys
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic: Cyclic_peptide_47
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

```
<400> SEQUENCE: 49

Asp Xaa Ala Tyr His Leu Gly Met Leu Val Trp Xaa Thr Lys Lys
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic: Cyclic_peptide_48
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.
<220> FEATURE:
<221> NAME/KEY: MISC_FEATURE
<222> LOCATION: (12)..(12)
<223> OTHER INFORMATION: Xaa2 is an amino acid residue induced from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue induced from
      L-homocysteine.

<400> SEQUENCE: 50

Asp Xaa Ala Tyr His Leu Gly Asn Leu Val Trp Xaa Thr Lys Lys
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic: Cyclic_peptide_49
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 51

Asp Xaa Ala Tyr His Leu Gly Glu Ile Val Trp Xaa Thr Lys Lys
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic: Cyclic_peptide_50
<220> FEATURE:
<221> NAME/KEY: MISC_FEATURE
```

```
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 52

Asp Xaa Ala Tyr His Leu Gly Glu Met Val Trp Xaa Thr Lys Lys
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic: Cyclic_peptide_51
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 53

Asp Xaa Ala Tyr His Leu Gly Glu Lys Val Trp Xaa Thr Lys Lys
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic: Cyclic_peptide_52
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.
<220> FEATURE:
<221> NAME/KEY: MISC_FEATURE
<222> LOCATION: (12)..(12)
<223> OTHER INFORMATION: Xaa2 is an amino acid residue induced from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue induced from
      L-homocysteine.

<400> SEQUENCE: 54
```

-continued

Asp Xaa Ala Tyr His Leu Gly Glu Arg Val Trp Xaa Thr Lys Lys
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic: Cyclic_peptide_53
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 55

Asp Xaa Ala Tyr His Leu Gly Glu Leu Ile Trp Xaa Thr Lys Lys
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic: Cyclic_peptide_54
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 56

Asp Xaa Ser Tyr His Leu Gly Glu Leu Val Trp Xaa Thr Lys Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic: Cyclic_peptide_55
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<223> OTHER INFORMATION: Xaa2 and Xaa12 are bridged by a disulfide
      bond..
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 57

Asp Xaa Thr Tyr His Leu Gly Glu Leu Val Trp Xaa Thr Lys Lys
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic: Cyclic_peptide_56
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 58

Asp Xaa Ala Trp His Leu Gly Glu Leu Val Trp Xaa Thr Lys Lys
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic: Cyclic_peptide_57
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 59

Asp Xaa Ala Phe His Leu Gly Glu Leu Val Trp Xaa Thr Lys Lys
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic: Cyclic_peptide_58
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 60

Asp Xaa Ala His His Leu Gly Glu Leu Val Trp Xaa Thr Lys Lys
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic: Cyclic_peptide_59
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 and Xaa12 are amino acid residues derived
      from L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 61

Asp Xaa Ala Tyr Tyr Leu Gly Glu Leu Val Trp Xaa Thr Lys Lys
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic: Cyclic_peptide_60
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 62

Asp Xaa Ala Tyr His Met Gly Glu Leu Val Trp Xaa Thr Lys Lys
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic: Cyclic_peptide_61
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 63

Asp Xaa Ala Tyr His Phe Gly Glu Leu Val Trp Xaa Thr Lys Lys
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic: Cyclic_peptide_62
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 64

Asp Xaa Ala Tyr His His Gly Glu Leu Val Trp Xaa Thr Lys Lys
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic: Cyclic_peptide_63
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 65

Asp Xaa Ala Tyr His Leu Gly Asp Leu Val Trp Xaa Thr Lys Lys
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic: Cyclic_peptide_64
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 66

```
Asp Xaa Ala Tyr His Leu Gly Met Leu Val Trp Xaa Thr Lys Lys
1               5                   10                  15
```

<210> SEQ ID NO 67
<211> LENGTH: 15
<212> TYPE: PRT
<213> ORGANISM: Artificial Sequence
<220> FEATURE:
<223> OTHER INFORMATION: Synthetic: Cyclic_peptide_65
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 67

```
Asp Xaa Ala Tyr His Leu Gly His Leu Val Trp Xaa Thr Lys Lys
1               5                   10                  15
```

<210> SEQ ID NO 68
<211> LENGTH: 15
<212> TYPE: PRT
<213> ORGANISM: Artificial Sequence
<220> FEATURE:
<223> OTHER INFORMATION: Synthetic: Cyclic_peptide_66
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 68

```
Asp Xaa Ala Tyr His Leu Gly Asn Leu Val Trp Xaa Thr Lys Lys
1               5                   10                  15
```

<210> SEQ ID NO 69
<211> LENGTH: 15
<212> TYPE: PRT
<213> ORGANISM: Artificial Sequence
<220> FEATURE:
<223> OTHER INFORMATION: Synthetic: Cyclic_peptide_67
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 69

```
Asp Xaa Ala Tyr His Leu Gly Glu Ile Val Trp Xaa Thr Lys Lys
```

<210> SEQ ID NO 70
<211> LENGTH: 15
<212> TYPE: PRT
<213> ORGANISM: Artificial Sequence
<220> FEATURE:
<223> OTHER INFORMATION: Synthetic: Cyclic_peptide_68
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 70

Asp Xaa Ala Tyr His Leu Gly Glu Met Val Trp Xaa Thr Lys Lys
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic: Cyclic_peptide_69
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 71

Asp Xaa Ala Tyr His Leu Gly Glu Lys Val Trp Xaa Thr Lys Lys
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic: Cyclic_peptide_70
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa2 and Xaa12 are amino acid residues induced
      from L-homocysteine.
<220> FEATURE:
<221> NAME/KEY: MISC_FEATURE

```
<222> LOCATION: (12)..(12)
<223> OTHER INFORMATION: Xaa12 is an amino acid residue derived from
      L-homocysteine.

<400> SEQUENCE: 72

Asp Xaa Ala Tyr His Leu Gly Glu Arg Val Trp Xaa Thr Lys Lys
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic: Cyclic_peptide_71
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 is an amino acid residue derived from
      L-homocysteine.
<220> FEATURE:
<221> NAME/KEY: MISC_FEATURE
<222> LOCATION: (12)..(12)
<223> OTHER INFORMATION: Xaa12 is an amino acid residue derived from
      L-homocysteine.

<400> SEQUENCE: 73

Asp Xaa Ala Tyr His Leu Gly Glu Leu Ile Trp Xaa Thr Lys Lys
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic: Cyclic_peptide_72
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-penicillamine.

<400> SEQUENCE: 74

Asp Xaa Ala Tyr His Leu Gly Glu Leu Val Trp Xaa Thr Lys Lys
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic: Cyclic_peptide_73
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      L-penicillamine.
<220> FEATURE:
<221> NAME/KEY: MISC_FEATURE
<222> LOCATION: (12)..(12)
```

```
<223> OTHER INFORMATION: Xaa12 is an amino acid residue derived from
      N-epsilon-chloroacetyl-L-lysine.

<400> SEQUENCE: 75

Asp Xaa Ala Tyr His Leu Gly Glu Leu Val Trp Xaa Thr Lys Lys
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic: Cyclic_peptide_74
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-penicillamine.

<400> SEQUENCE: 76

Asp Xaa Ala Tyr His Arg Gly Glu Leu Val Trp Xaa Thr Lys Lys
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic: Cyclic_peptide_75
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-penicillamine.
<220> FEATURE:
<221> NAME/KEY: MISC_FEATURE
<222> LOCATION: (13)..(13)
<223> OTHER INFORMATION: Xaa13 is an amino acid residue derived from
      L-homoserine.

<400> SEQUENCE: 77

Asp Xaa Ala Tyr His Leu Gly Glu Leu Val Trp Xaa Xaa Lys Lys
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic: Cyclic_peptide_76
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
```

```
       (2S)-2-amino-3-[(2-chloroacetyl)amino]propanoic acid.
<220> FEATURE:
<221> NAME/KEY: MISC_FEATURE
<222> LOCATION: (12)..(12)
<223> OTHER INFORMATION: Xaa12 is an amino acid residue derived from
      L-cysteine.

<400> SEQUENCE: 78

Asp Xaa Ala Tyr His Leu Gly Glu Leu Val Trp Xaa Thr Lys Lys
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic: Cyclic_peptide_77
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      (2S)-2-amino-4-[(2-chloroacetyl)amino]butanoic acid.
<220> FEATURE:
<221> NAME/KEY: MISC_FEATURE
<222> LOCATION: (12)..(12)
<223> OTHER INFORMATION: Xaa12 is an amino acid residue derived from
      L-cysteine.

<400> SEQUENCE: 79

Asp Xaa Ala Tyr His Leu Gly Glu Leu Val Trp Xaa Thr Lys Lys
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic: Cyclic_peptide_78
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-delta-chloroacetyl-L-ornithine.
<220> FEATURE:
<221> NAME/KEY: MISC_FEATURE
<222> LOCATION: (12)..(12)
<223> OTHER INFORMATION: Xaa12 is an amino acid residue derived from
      L-cysteine.

<400> SEQUENCE: 80

Asp Xaa Ala Tyr His Leu Gly Glu Leu Val Trp Xaa Thr Lys Lys
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic: Cyclic_peptide_79
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
```

```
<220> FEATURE:
<221> NAME/KEY: MISC_FEATURE
<222> LOCATION: (12)..(12)
<223> OTHER INFORMATION: Xaa12 is an amino acid residue derived from
      L-cysteine.

<400> SEQUENCE: 81

Asp Xaa Ala Tyr His Leu Gly Glu Leu Val Trp Xaa Thr Lys Lys
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic: Cyclic_peptide_80
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      L-cysteine.
<220> FEATURE:
<221> NAME/KEY: MISC_FEATURE
<222> LOCATION: (12)..(12)
<223> OTHER INFORMATION: Xaa12 is an amino acid residue derived from
      (2S)-2-amino-3-[(2-chloroacetyl)amino]propanoic acid.

<400> SEQUENCE: 82

Asp Xaa Ala Tyr His Leu Gly Glu Leu Val Trp Xaa Thr Lys Lys
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic: Cyclic_peptide_81
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      L-cysteine.
<220> FEATURE:
<221> NAME/KEY: MISC_FEATURE
<222> LOCATION: (12)..(12)
<223> OTHER INFORMATION: Xaa12 is an amino acid residue derived from
      (2S)-2-amino-4-[(2-chloroacetyl)amino]butanoic acid.

<400> SEQUENCE: 83

Asp Xaa Ala Tyr His Leu Gly Glu Leu Val Trp Xaa Thr Lys Lys
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic: Cyclic peptide 87
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      L-cysteine.
<220> FEATURE:
```

```
<221> NAME/KEY: MISC_FEATURE
<222> LOCATION: (12)..(12)
<223> OTHER INFORMATION: Xaa12 is an amino acid residue derived from
      N-delta-chloroacetyl-L-ornithine.

<400> SEQUENCE: 84

Asp Xaa Ala Tyr His Leu Gly Glu Leu Val Trp Xaa Thr Lys Lys
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic: Cyclic_peptide_83
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      L-cysteine.
<220> FEATURE:
<221> NAME/KEY: MISC_FEATURE
<222> LOCATION: (12)..(12)
<223> OTHER INFORMATION: Xaa12 is an amino acid residue derived from
      N-epsilon-chloroacetyl-L-lysine.

<400> SEQUENCE: 85

Asp Xaa Ala Tyr His Leu Gly Glu Leu Val Trp Xaa Thr Lys Lys
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic: Cyclic_peptide_91
<220> FEATURE:
<221> NAME/KEY: MISC_FEATURE
<223> OTHER INFORMATION: Xaa2 and Xaa12 are bridged by an amide bond.
<220> FEATURE:
<221> NAME/KEY: MISC_FEATURE
<222> LOCATION: (2)..(2)
<223> OTHER INFORMATION: Xaa2 is an amino acid residue derived from
      L-glutamic acid.
<220> FEATURE:
<221> NAME/KEY: MISC_FEATURE
<222> LOCATION: (12)..(12)
<223> OTHER INFORMATION: Xaa12 is an amino acid residue derived from
      L-lysine.

<400> SEQUENCE: 86

Asp Xaa Ala Tyr His Arg Gly Glu Leu Val Trp Xaa Thr Lys Lys
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic: Cyclic_peptide_92
<220> FEATURE:
<221> NAME/KEY: MISC_FEATURE
<223> OTHER INFORMATION: Xaa2 and Xaa12 are bridged by a disulfide bond.
<220> FEATURE:
<221> NAME/KEY: MISC_FEATURE
<222> LOCATION: (2)..(2)
<223> OTHER INFORMATION: Xaa2 and Xaa12 are amino acid residues derived
      from L-cysteine.
<220> FEATURE:
<221> NAME/KEY: MISC_FEATURE
```

```
<222> LOCATION: (12)..(12)
<223> OTHER INFORMATION: Xaa2 and Xaa12 are amino acid residues derived
      from L-cysteine.

<400> SEQUENCE: 87

Asp Xaa Ala Tyr His Arg Gly Glu Leu Val Trp Xaa Thr Lys Lys
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic: Cyclic_peptide_93
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-penicillamine.

<400> SEQUENCE: 88

Asp Xaa Ser Tyr His Leu Gly Glu Leu Val Trp Xaa Thr Lys Lys
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic: Cyclic_peptide_94
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-cysteine.

<400> SEQUENCE: 89

Asp Xaa Ser Tyr His Leu Gly Glu Leu Val Trp Xaa Thr Lys Lys
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic: Cyclic_peptide_95
<220> FEATURE:
<221> NAME/KEY: MISC_FEATURE
<223> OTHER INFORMATION: Xaa2 and Xaa12 are bridged by a thioether bond.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
```

```
<223> OTHER INFORMATION: Xaa12 is an amino acid residue derived from
      L-cysteine.

<400> SEQUENCE: 90

Asp Xaa Ala Tyr His Arg Gly Glu Leu Val Trp Xaa Thr Lys Lys
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic: Cyclic_peptide_96
<220> FEATURE:
<221> NAME/KEY: MISC_FEATURE
<223> OTHER INFORMATION: Xaa2 and Xaa12 are bridged by a tioether bond.
<220> FEATURE:
<221> NAME/KEY: MISC_FEATURE
<222> LOCATION: (1)..(1)
<223> OTHER INFORMATION: Xaa1 is an amino acid residue derived from
      L-homoserine.
<220> FEATURE:
<221> NAME/KEY: MISC_FEATURE
<222> LOCATION: (2)..(2)
<223> OTHER INFORMATION: Xaa2 is an amino acid residue derived from
      N-epsilon-chloroacetyl-L-lysine.
<220> FEATURE:
<221> NAME/KEY: MISC_FEATURE
<222> LOCATION: (12)..(12)
<223> OTHER INFORMATION: Xaa12 is an amino acid residue derived from
      L-cysteine.

<400> SEQUENCE: 91

Xaa Xaa Ala Tyr His Arg Gly Glu Leu Val Trp Xaa Thr Lys Lys
1               5                   10                  15

<210> SEQ ID NO 92
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: At least one, and up to three Xaa, maybe
      present. Xaa can be any naturally occurring amino acid.
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: At least one, and up to three Xaa, maybe
      present. Xaa can be any naturally occurring amino acid.

<400> SEQUENCE: 92

Xaa Xaa Xaa Cys Xaa Xaa His Arg Gly Xaa Leu Val Trp Cys Xaa Xaa
1               5                   10                  15

Xaa

<210> SEQ ID NO 93
<211> LENGTH: 20
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid

<400> SEQUENCE: 93

Xaa Xaa Xaa Xaa Cys Xaa Xaa Xaa Xaa Gly Glu Leu Val Trp Cys Xaa
1               5                   10                  15

Xaa Xaa Xaa Xaa
            20

<210> SEQ ID NO 94
<211> LENGTH: 9
<212> TYPE: PRT
<213> ORGANISM: Artificial Sequence
<220> FEATURE:
<223> OTHER INFORMATION: Synthetic peptide

<400> SEQUENCE: 94

Ala Trp His Leu Gly Glu Leu Val Trp
1               5

<210> SEQ ID NO 95
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N-terminal group
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: C-terminal group

<400> SEQUENCE: 95

Xaa Xaa Xaa Xaa Xaa Xaa Ala Tyr His Xaa Gly Glu Leu Val Trp Xaa
1               5                   10                  15

Xaa Xaa Xaa Xaa Xaa
            20
```